US007683033B2

(12) United States Patent
Cottrell et al.

(10) Patent No.: US 7,683,033 B2
(45) Date of Patent: Mar. 23, 2010

(54) INHIBITORS OF SERINE PROTEASES, PARTICULARLY HCV NS3-NS4A PROTEASE

(75) Inventors: Kevin M. Cottrell, Cambridge, MA (US); John J. Court, Littleton, MA (US); David D. Deininger, Arlington, MA (US); Luc J. Farmer, Foxboro, MA (US); Janos Pitlik, Westborough, MA (US); Robert B. Perni, Marlborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 11/051,977

(22) Filed: Feb. 4, 2005

(65) Prior Publication Data

US 2005/0215486 A1  Sep. 29, 2005

Related U.S. Application Data

(60) Provisional application No. 60/541,738, filed on Feb. 4, 2004.

(51) Int. Cl.
*A61K 38/07* (2006.01)
*A61K 39/42* (2006.01)
(52) U.S. Cl. .................... 514/18; 530/330; 424/149.1
(58) Field of Classification Search .................. None
See application file for complete search history.

(56) References Cited

U.S. PATENT DOCUMENTS

| | | | |
|---|---|---|---|
| 6,265,380 B1 | 7/2001 | Tung et al. | |
| 6,608,067 B1 | 8/2003 | Tung et al. | |
| 6,617,309 B2 | 9/2003 | Tung et al. | |
| 6,909,000 B2 | 6/2005 | Farmer et al. | |
| 7,109,172 B2 * | 9/2006 | Britt et al. | 514/18 |
| 7,208,600 B2 | 4/2007 | Cottrell et al. | |
| 7,241,796 B2 | 7/2007 | Farmer et al. | |
| 7,273,885 B2 * | 9/2007 | Pitlik et al. | 514/414 |
| 7,365,092 B2 * | 4/2008 | Cottrell et al. | 514/422 |
| 2003/0236242 A1 | 12/2003 | Perni et al. | |
| 2004/0077600 A1 | 4/2004 | Tung et al. | |
| 2004/0266731 A1 | 12/2004 | Tung et al. | |
| 2005/0080017 A1 | 4/2005 | Cottrell et al. | |
| 2005/0090450 A1 | 4/2005 | Farmer et al. | |
| 2005/0119189 A1 | 6/2005 | Cottrell et al. | |
| 2005/0137139 A1 | 6/2005 | Perni et al. | |
| 2005/0197299 A1 | 9/2005 | Babine et al. | |
| 2006/0211629 A1 | 9/2006 | Britt et al. | |
| 2007/0161789 A1 | 7/2007 | Cottrell et al. | |
| 2007/0179167 A1 | 8/2007 | Cottrell et al. | |
| 2007/0292933 A1 | 12/2007 | Pitlik et al. | |
| 2008/0045480 A1 | 2/2008 | Farmer et al. | |

FOREIGN PATENT DOCUMENTS

| | | |
|---|---|---|
| EP | 1 498 411 A1 | 1/2005 |
| EP | 1008592 | 2/2006 |
| WO | WO 99/17775 | 4/1999 |
| WO | WO 00/16767 | 3/2000 |
| WO | WO-00/16767 * | 3/2000 |
| WO | WO 01/40262 * | 6/2001 |
| WO | WO 02/18369 A2 | 3/2002 |
| WO | WO 03/006490 A1 | 1/2003 |
| WO | WO 03/062265 A2 | 7/2003 |
| WO | WO 03/087092 A2 | 10/2003 |
| WO | WO 03/091202 A1 | 11/2003 |
| WO | WO 2004/072243 A2 | 8/2004 |
| WO | WO 2004/093798 A2 | 11/2004 |
| WO | WO 2004/113365 A2 | 12/2004 |

OTHER PUBLICATIONS

Isaac O. Donkor et al., Design, Synthesis, Molecular Modeling Studies, and Calpain Inhibitory Activity of Novel a-Ketoamides Incorporating Polar Residues at the PY-Position, J. Med. Chem. 2004, 47, 72-79.

* cited by examiner

*Primary Examiner*—Andrew D Kosar
*Assistant Examiner*—Satyanarayana R Gudibande
(74) *Attorney, Agent, or Firm*—Susan C. Kelly

(57) ABSTRACT

The present invention relates to compounds of formula I:

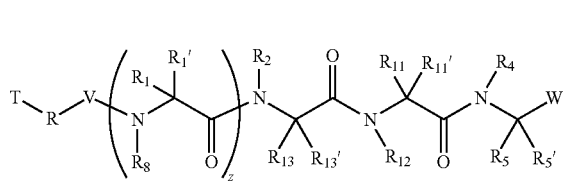

or a pharmaceutically acceptable salt or mixtures thereof that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection and to processes for preparing the compounds. The invention also relates to methods of treating an HCV infection in a patient by administering a composition comprising a compound of this invention. The invention further relates to processes for preparing these compounds.

5 Claims, No Drawings

INHIBITORS OF SERINE PROTEASES, PARTICULARLY HCV NS3-NS4A PROTEASE

CROSS REFERENCE TO RELATED APPLICATIONS

The present application claims the benefit, under 35 U.S.C. §119, of U.S. Provisional patent application No. 60/541,738, filed Feb. 4, 2004, entitled "Inhibitors of Serine Proteases, Particularly HCV NS3-NS4A Protease", the entire contents of which is hereby incorporated by reference.

TECHNICAL FIELD OF THE INVENTION

The present invention relates to compounds that inhibit serine protease activity, particularly the activity of hepatitis C virus NS3-NS4A protease. As such, they act by interfering with the life cycle of the hepatitis C virus and are also useful as antiviral agents. The invention further relates to compositions comprising these compounds either for ex vivo use or for administration to a patient suffering from HCV infection. The invention also relates to methods of treating an HCV infection in a patient by administering a composition comprising a compound of this invention.

BACKGROUND OF THE INVENTION

Infection by hepatitis C virus ("HCV") is a compelling human medical problem. HCV is recognized as the causative agent for most cases of non-A, non-B hepatitis, with an estimated human sero-prevalence of 3% globally [A. Alberti et al., "Natural History of Hepatitis C," J. Hepatology, 31., (Suppl. 1), pp. 17-24 (1999)]. Nearly four million individuals may be infected in the United States alone [M. J. Alter et al., "The Epidemiology of Viral Hepatitis in the United States, Gastroenterol. Clin. North Am., 23, pp. 437-455 (1994); M. J. Alter "Hepatitis C Virus Infection in the United States," J. Hepatology, 31., (Suppl. 1), pp. 88-91 (1999)].

Upon first exposure to HCV only about 20% of infected individuals develop acute clinical hepatitis while others appear to resolve the infection spontaneously. In almost 70% of instances, however, the virus establishes a chronic infection that persists for decades [S. Iwarson, "The Natural Course of Chronic Hepatitis," FEMS Microbiology Reviews, 14, pp. 201-204 (1994); D. Lavanchy, "Global Surveillance and Control of Hepatitis C," J. Viral Hepatitis, 6, pp. 35-47 (1999)]. This usually results in recurrent and progressively worsening liver inflammation, which often leads to more severe disease states such as cirrhosis and hepatocellular carcinoma [M. C. Kew, "Hepatitis C and Hepatocellular Carcinoma", FEMS Microbiology Reviews, 14, pp. 211-220 (1994); I. Saito et. al., "Hepatitis C Virus Infection is Associated with the Development of Hepatocellular Carcinoma," Proc. Natl. Acad. Sci. USA, 87, pp. 6547-6549 (1990)]. Unfortunately, there are no broadly effective treatments for the debilitating progression of chronic HCV.

The HCV genome encodes a polyprotein of 3010-3033 amino acids [Q. L. Choo, et. al., "Genetic Organization and Diversity of the Hepatitis C Virus." Proc. Natl. Acad. Sci. USA, 88, pp. 2451-2455 (1991); N. Kato et al., "Molecular Cloning of the Human Hepatitis C Virus Genome From Japanese Patients with Non-A, Non-B Hepatitis," Proc. Natl. Acad. Sci. USA, 87, pp. 9524-9528 (1990); A. Takamizawa et. al., "Structure and Organization of the Hepatitis C Virus Genome Isolated From Human Carriers," J. Virol., 65, pp. 1105-1113 (1991)]. The HCV nonstructural (NS) proteins are presumed to provide the essential catalytic machinery for viral replication. The NS proteins are derived by proteolytic cleavage of the polyprotein [R. Bartenschlager et. al., "Nonstructural Protein 3 of the Hepatitis C Virus Encodes a Serine-Type Proteinase Required for Cleavage at the NS3/4 and NS4/5 Junctions," J. Virol., 67, pp. 3835-3844 (1993); A. Grakoui et. al., "Characterization of the Hepatitis C Virus-Encoded Serine Proteinase: Determination of Proteinase-Dependent Polyprotein Cleavage Sites," J. Virol., 67, pp. 2832-2843 (1993); A. Grakoui et. al., "Expression and Identification of Hepatitis C Virus Polyprotein Cleavage Products," J. Virol., 67, pp. 1385-1395 (1993); L. Tomei et. al., "NS3 is a serine protease required for processing of hepatitis C virus polyprotein", J. Virol., 67, pp. 4017-4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", Proc. Natl. Acad. Sci. USA, 87, pp. 8898-8902 (1990)]. The first 181 amino acids of NS3 (residues 1027-1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", J. Virol., 68, pp. 8147-8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing. HIV protease inhibitors, which inhibit viral protein processing, are potent antiviral agents in man indicating that interrupting this stage of the viral life cycle results in therapeutically active agents. Consequently HCV NS3 serine protease is also an attractive target for drug discovery.

There are not currently any satisfactory anti-HCV agents or treatments. Until recently, the only established therapy for HCV disease was interferon treatment. Until recently, the only established therapy for HCV disease was interferon treatment. However, interferons have significant side effects [M. A. Wlaker et al., "Hepatitis C Virus: An Overview of Current Approaches and Progress," DDT, 4, pp. 518-29 (1999); D. Moradpour et al., "Current and Evolving Therapies for Hepatitis C," Eur. J. Gastroenterol. Hepatol., 11, pp. 1199-1202 (1999); H. L. A. Janssen et al. "Suicide Associated with Alfa-Interferon Therapy for Chronic Viral Hepatitis," J. Hepatol., 21, pp. 241-243 (1994); P. F. Renault et al., "Side Effects of Alpha Interferon," Seminars in Liver Disease, 9, pp. 273-277. (1989)] and induce long term remission in only a fraction (~25%) of cases [O. Weiland, "Interferon Therapy in Chronic Hepatitis C Virus Infection", FEMS Microbiol. Rev., 14, pp. 279-288 (1994)]. Recent introductions of the pegylated forms of interferon (PEG-INTRON® and PEGASYS®) and the combination therapy of ribavirin and pegylated interferon (REBETROL®) have resulted in only modest improvements in remission rates and only partial reductions in side effects. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention addresses these needs by providing a compound of formula I:

I or a pharmaceutically acceptable salt or mixtures thereof, wherein the variables are as defined herein.

The present invention also provides a compound of formula I-1:

I-1 or a pharmaceutically acceptable salt or mixtures thereof, wherein the variables are as defined herein.

The invention also relates to compositions that comprise the above compounds and the use thereof. Such compositions may be used to pre-treat invasive devices to be inserted into a patient, to treat biological samples, such as blood, prior to administration to a patient, and for direct administration to a patient. In each case the composition will be used to inhibit HCV replication and to lessen the risk of or the severity of HCV infection.

The invention also relates to processes for preparing the compounds of formula I.

DETAILED DESCRIPTION OF THE INVENTION

The present invention provides a compound of formula I:

I or a pharmaceutically acceptable salt or mixtures thereof, wherein:
z is 0 or 1;
V is —C(O)—, —S(O)—, —C(R')$_2$— or —S(O)$_2$—;
R is —C(O)—, —S(O)—, —S(O)$_2$—, —N(R$_8$)—, —O—, or a bond;

T is:
(C6-C10)-aryl,
(C6-C10)-aryl-(C1-C12)aliphatic,
(C3-C10)-cycloalkyl or -cycloalkenyl,
[(C3-C10)-cycloalkyl or -cycloalkenyl]-(C1-C12)-aliphatic,
(C3-C10)-heterocyclyl,
(C3-C10)-heterocyclyl-(C1-C12)-aliphatic,
(C5-C10)heteroaryl, or
(C5-C10)heteroaryl-(C1-C12)-aliphatic;
  wherein up to 3 aliphatic carbon atoms in T may be optionally replaced with —S—, —S(O)—, —S(O)$_2$—, —O—, —N—, or —N(H)—, in a chemically stable arrangement;
  wherein each T may be optionally substituted with up to 3 J substituents;
  wherein J is halogen, —OR', —OC(O)N(R')$_2$, —NO$_2$, —CN, —CF$_3$, —OCF$_3$, —R', oxo, thioxo, 1,2-methylenedioxy, 1,2-ethylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'), wherein;
two R' groups together with the nitrogen to which they are bound form a 3- to a 20-membered mono-, an 8- to 20-membered bi- or tri-cyclic heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and SO$_2$;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J$_2$;
  each R' is independently selected from:
    hydrogen-,
    (C1-C12)-aliphatic-,
    (C3-C10)-cycloalkyl or -cycloalkenyl-,
    [(C3-C10)-cycloalkyl or -cycloalkenyl]-(C1-C12)-aliphatic-,
    (C6-C10)-aryl-,
    (C6-C10)-aryl-(C1-C12)aliphatic-,
    (C3-C10)-heterocyclyl-,
    (C6-C10)-heterocyclyl-(C1-C12)aliphatic-,
    (C5-C10)-heteroaryl-, or (C5-C10)-heteroaryl-(C1-C12)-aliphatic-,
  wherein R' is optionally substituted with up to 3 substituents selected independently from J$_2$;
wherein J$_2$ is halogen, —OR', —OC(O)N(R')$_2$, —NO$_2$, —CN, —CF$_3$, —OCF$_3$, —R', oxo, thioxo, 1,2-methylenedioxy, —N(R')$_2$, —SR', —SOR', —SO$_2$R', —SO$_2$N(R')$_2$, —SO$_3$R', —C(O)R', —C(O)C(O)R', —C(O)CH$_2$C(O)R', —C(S)R', —C(O)OR', —OC(O)R', —C(O)N(R')$_2$, —OC(O)N(R')$_2$, —C(S)N(R')$_2$, —(CH$_2$)$_{0-2}$NHC(O)R', —N(R')N(R')COR', —N(R')N(R')C(O)OR', —N(R')N(R')CON(R')$_2$, —N(R')SO$_2$R', —N(R')SO$_2$N(R')$_2$, —N(R')C(O)OR', —N(R')C(O)R', —N(R')C(S)R', —N(R')C(O)N(R')$_2$, —N(R')C(S)N(R')$_2$, —N(COR')COR', —N(OR')R', —C(=NH)N(R')$_2$, —C(O)N(OR')R', —C(=NOR')R', —OP(O)(OR')$_2$, —P(O)(R')$_2$, —P(O)(OR')$_2$, or —P(O)(H)(OR'); or T is:

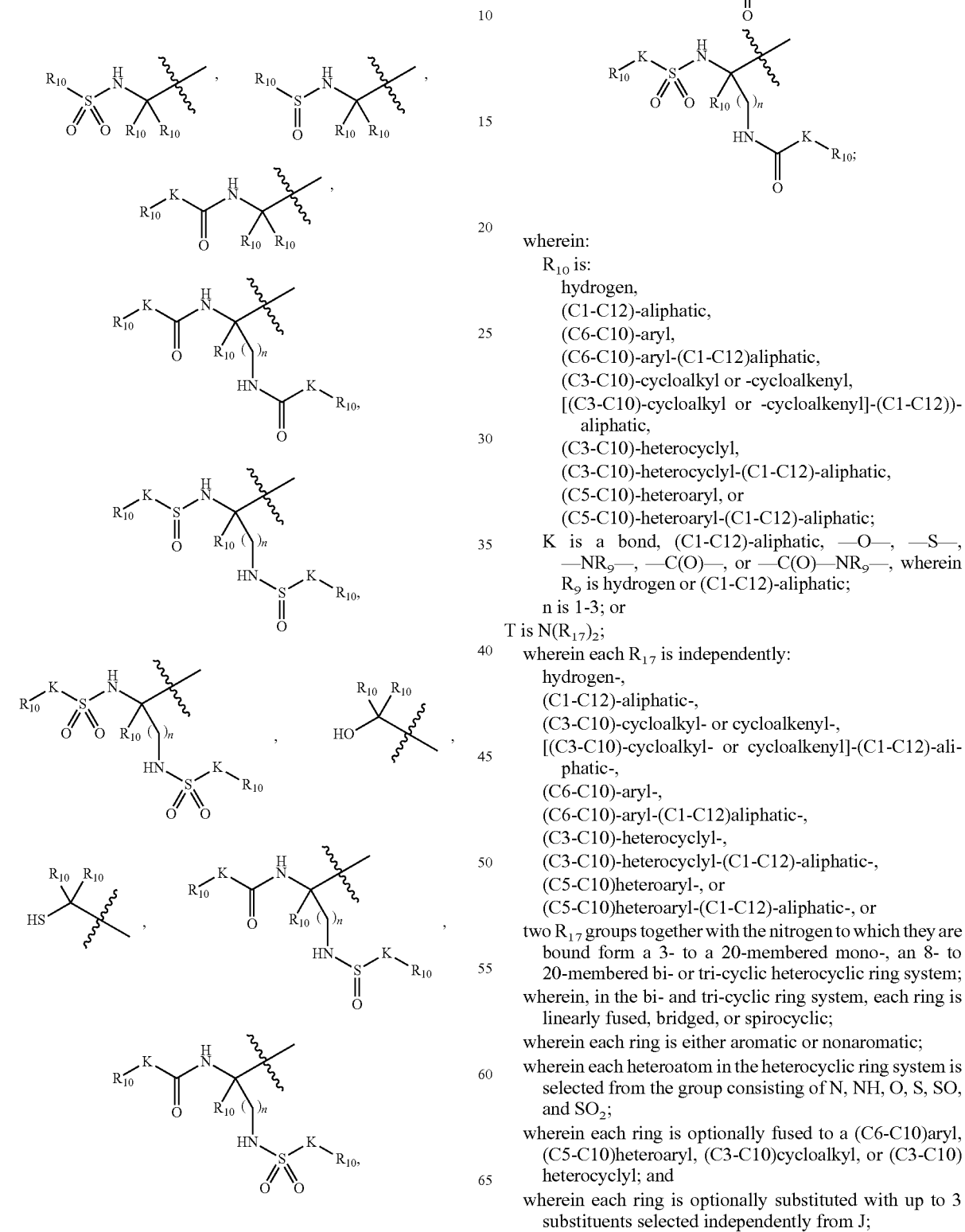

wherein:

R$_{10}$ is:
  hydrogen,
  (C1-C12)-aliphatic,
  (C6-C10)-aryl,
  (C6-C10)-aryl-(C1-C12)aliphatic,
  (C3-C10)-cycloalkyl or -cycloalkenyl,
  [(C3-C10)-cycloalkyl or -cycloalkenyl]-(C1-C12))-aliphatic,
  (C3-C10)-heterocyclyl,
  (C3-C10)-heterocyclyl-(C1-C12)-aliphatic,
  (C5-C10)-heteroaryl, or
  (C5-C10)-heteroaryl-(C1-C12)-aliphatic;

K is a bond, (C1-C12)-aliphatic, —O—, —S—, —NR$_9$—, —C(O)—, or —C(O)—NR$_9$—, wherein R$_9$ is hydrogen or (C1-C12)-aliphatic;

n is 1-3; or

T is N(R$_{17}$)$_2$;

wherein each R$_{17}$ is independently:
  hydrogen-,
  (C1-C12)-aliphatic-,
  (C3-C10)-cycloalkyl- or cycloalkenyl-,
  [(C3-C10)-cycloalkyl- or cycloalkenyl]-(C1-C12)-aliphatic-,
  (C6-C10)-aryl-,
  (C6-C10)-aryl-(C1-C12)aliphatic-,
  (C3-C10)-heterocyclyl-,
  (C3-C10)-heterocyclyl-(C1-C12)-aliphatic-,
  (C5-C10)heteroaryl-, or
  (C5-C10)heteroaryl-(C1-C12)-aliphatic-, or two R$_{17}$ groups together with the nitrogen to which they are bound form a 3- to a 20-membered mono-, an 8- to 20-membered bi- or tri-cyclic heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and SO$_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 3 substituents selected independently from J;

W is:

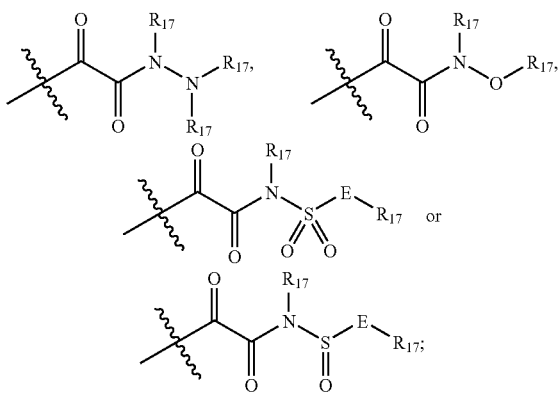

wherein:
E is selected from $N(R_{17})$ or a bond;
two $R_{17}$ groups together with the nitrogen to which they are bound form a 3- to a 20-membered mono- or an 8- to 20-membered bi- or tri-cyclic heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J;
$R_5$ and $R_{5'}$ are independently:
hydrogen
(C1-C12)-aliphatic,
(C6-C10)-aryl, or
(C5-C10)-heteroaryl,
wherein any hydrogen in the (C1-C12)-aliphatic is optionally replaced with halogen;
wherein any terminal carbon atom is optionally substituted with sulfhydryl or hydroxy; and
wherein up to two aliphatic carbon atoms may be replaced by a heteroatom selected from N, NH, O, S, SO, or $SO_2$;
wherein any ring is optionally substituted with up to 3 substituents selected independently from $J_2$; and
wherein each heteroatom in the heteroaryl ring system is selected from the group consisting of N, NH, O, S, SO, and $SO_2$; or
$R_5$ and $R_{5'}$ together with the atom to which they are bound optionally form a 3- to 6-membered ring having up to 2 heteroatoms selected from N, NH, O, S, SO, or $SO_2$; wherein the ring is optionally substituted with up to 2 substituents selected independently from J;
$R_1$ (if present), $R_{1'}$ (if present), $R_{11}$, $R_{11'}$, $R_{13}$, and $R_{13'}$ are independently:
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each of $R_1$ (if present), $R_{1'}$ (if present), $R_{11}$, $R_{11'}$, $R_{13}$, and $R_{13'}$ is independently and optionally substituted with up to 3 substituents independently selected from J;
wherein any ring is optionally fused to a (C6-C10)aryl, (C5-C10)heteroaryl, (C3-C10)cycloalkyl, or (C3-C10)heterocyclyl;
wherein up to 3 aliphatic carbon atoms in each of $R_1$ (if present), $R_{1'}$ (if present), $R_{11}$, $R_{11'}$, $R_{13}$, and $R_{13'}$ may be replaced by a heteroatom selected from O, N, NH, S, SO, or $SO_2$ in a chemically stable arrangement; or
$R_1$ and $R_{1'}$ (both if present) together with the atom to which they are bound optionally form a 3- to 6-membered ring having up to 2 heteroatoms selected from N, NH, O, S, SO, or $SO_2$; wherein the ring system is optionally substituted with up to 2 substituents selected independently from J; or
$R_{11}$ and $R_{11'}$ together with the atom to which they are bound optionally form a 3- to 6-membered ring having up to 2 heteroatoms selected from N, NH, O, S, SO, or $SO_2$; wherein the ring is optionally substituted with up to 2 substituents selected independently from J; or
$R_{13}$ and $R_{13'}$ together with the atom to which they are bound is a 3- to 6-membered ring having up to 2 heteroatoms selected from N, NH, O, S, SO, or $SO_2$; wherein the ring is optionally substituted with up to 2 substituents selected independently from J;
$R_2$, $R_4$, $R_8$ (if present), and $R_{12}$ are independently
hydrogen-,
(C1-C12)-aliphatic-,
(C3-C10)-cycloalkyl or -cycloalkenyl-,
[(C3-C10)-cycloalkyl or -cycloalkenyl]-(C1-C12)-aliphatic-,
(C6-C10)-aryl-,
(C6-C10)-aryl-(C1-C12)aliphatic-,
(C3-C10)-heterocyclyl-,
(C6-C10)-heterocyclyl-(C1-C12)aliphatic,
(C5-C10)-heteroaryl-, or
(C5-C10)-heteroaryl-(C1-C12)-aliphatic-,
wherein each $R_2$, $R_4$, $R_8$ (if present), and $R_{12}$ is independently and optionally substituted with up to 3 substituents independently selected from J;
wherein up to two aliphatic carbon atoms in $R_2$, $R_4$, $R_8$ (if present), and $R_{12}$ may be replaced by a heteroatom selected from O, N, NH, S, SO, or $SO_2$; or
$R_{11}$ and $R_{12}$ together with the atoms to which they are bound form a 3- to a 20-membered mono-, an 8- to 20-membered bi- or tri-cyclic carbocyclic or heterocyclic ring system;
wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J; or
$R_{12}$ and $R_{13}$ together with the atoms to which they are bound form a 4- to a 20-membered mono-, an 8- to 20-membered bi- or tri-cyclic carbocyclic or heterocyclic ring system;
wherein, in the bi- and tri-cyclic ring system, each ring is linearly fused, bridged, or spirocyclic;
wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 3 substituents selected independently from J; or $R_{11}$ and $R_{13}$ together with the atoms to which they are bound form a 5- to a 20-membered mono-, an 8- to 20-membered bi- or tri-cyclic carbocyclic or heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 3 substituents selected independently from J; or $R_{11}$, $R_{12}$, and $R_{13}$ together with the atoms to which they are bound form an 8- to a 20-membered bi- or tri-cyclic carbocyclic or heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 3 substituents selected independently from J; or $R_{13'}$ and $R_2$ together with the atoms to which they are bound form a 3- to a 20-membered mono-, an 8- to 20-membered bi- or tri-cyclic carbocyclic or heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 3 substituents selected independently from J; or $R_5$ and $R_{13}$ together with the atoms to which they are bound form a 18- to a 23-membered mono-, a 19- to 24-membered bi-, or a 20- to 25-membered tri-cyclic carbocyclic or heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 6 substituents selected independently from J; or $R_1$ (if present) and $R_{12}$ together with the atoms to which they are bound form a 18- to a 23-membered mono-, a 19- to 24-membered bi-, or a 20- to 25-membered tri-cyclic carbocyclic or heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10) heterocyclyl; and wherein each ring is optionally substituted with up to 6 substituents selected independently from J.

The present invention also provides a compound of formula I-1:

I-1 or a pharmaceutically acceptable salt or mixtures thereof, wherein, W, V, R, T, $R_1$, $R_{1'}$, $R_2$, $R_4$, $R_5$, $R_{5'}$, $R_8$, $R_{11}$, $R_{11'}$, $R_{12}$, $R_{13}$ and $R_{13'}$ are as defined above for compounds of formula I.

Definitions

The term "aryl" as used herein means a monocyclic or bicyclic carbocyclic aromatic ring system. Phenyl is an example of a monocyclic aromatic ring system. Bicyclic aromatic ring systems include systems wherein both rings are aromatic, e.g., naphthyl, and systems wherein only one of the two rings is aromatic, e.g., tetralin. It is understood that as used herein, the term "(C6-C10)-aryl-" includes any one of a C6, C7, C8, C9, and C10 monocyclic or bicyclic carbocyclic aromatic ring system.

The term "heterocyclyl" as used herein means a monocyclic or bicyclic non-aromatic ring system having 1 to 3 heteroatom or heteroatom groups in each ring selected from O, N, NH, S, SO, or $SO_2$ in a chemically stable arrangement. In a bicyclic non-aromatic ring system embodiment of "heterocyclyl" one or both rings may contain said heteroatom or heteroatom groups. It is understood that as used herein, the term "(C5-C10)-heterocyclyl-" includes any one of a 5, 6, 7, 8, 9, and 10 atom monocyclic or bicyclic non-aromatic ring system having 1 to 3 heteroatoms or heteroatom groups in each ring selected from O, N, NH, and S in a chemically stable arrangement.

The term "heteroaryl" as used herein means a monocyclic or bicyclic aromatic ring system having 1 to 3 heteroatom or heteroatom groups in each ring selected from O, N, NH or S in a chemically stable arrangement. In such a bicyclic aromatic ring system embodiment of "heteroaryl":

one or both rings may be aromatic; and one or both rings may contain said heteroatom or heteroatom groups. It is understood that as used herein, the term "(C5-C10)-heteroaryl-" includes any one of a 5, 6, 7, 8, 9, and 10 atom monocyclic or bicyclic aromatic ring system having 1 to 3 heteroatoms or heteroatom groups in each ring selected from O, N, NH, and S in a chemically stable arrangement.

Heterocyclic rings include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "aliphatic" as used herein means a straight chained or branched alkyl, alkenyl or alkynyl. It is understood that as used herein, the term "(C1-C12)-aliphatic-" includes any one of a C1, C2, C3, C4, C5, C6, C7, C8, C9, C10, C11, and C12 straight or branched alkyl chain of carbon atoms. It is also understood that alkenyl or alkynyl embodiments need at least two carbon atoms in the aliphatic chain. The term "cycloalkyl or cycloalkenyl" refers to a monocyclic or fused or bridged bicyclic carbocyclic ring system that is not aromatic. Cycloalkenyl rings have one or more units of unsaturation. It is also understood that as used herein, the term "(C3-C10)-cycloalkyl- or -cycloalkenyl-" includes any one of a C3, C4, C5, C6, C7, C8, C9, and C10 monocyclic or fused or bridged bicyclic carbocyclic ring. Cycloalkyl groups include cyclopropyl, cyclobutyl, cyclopentyl, cyclohexyl, cyclohexenyl, cycloheptyl, cycloheptenyl, nornbornyl, adamantyl and decalin-yl.

As used herein, the carbon atom designations may have the indicated integer and any intervening integer. For example, the number of carbon atoms in a (C1-C4)-alkyl group is 1, 2, 3, or 4. It should be understood that these designation refer to the total number of atoms in the appropriate group. For example, in a (C3-C10)-heterocyclyl the total number of carbon atoms and heteroatoms is 3 (as in aziridine), 4, 5, 6 (as in morpholine), 7, 8, 9, or 10.

The phrase "chemically stable arrangement" as used herein refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

EMBODIMENTS

In one form of any embodiment of the present invention, compounds of formula IIIA, IIIB, IIIC, and IIID are provided, wherein P1, P2, P3, and P4 designate the residues of a serine protease inhibitor as known to those skilled in the art, E is selected from $N(R_{17})$ or a bond, and V, R, T, and $R_{17}$, are as defined in any of the embodiments herein.

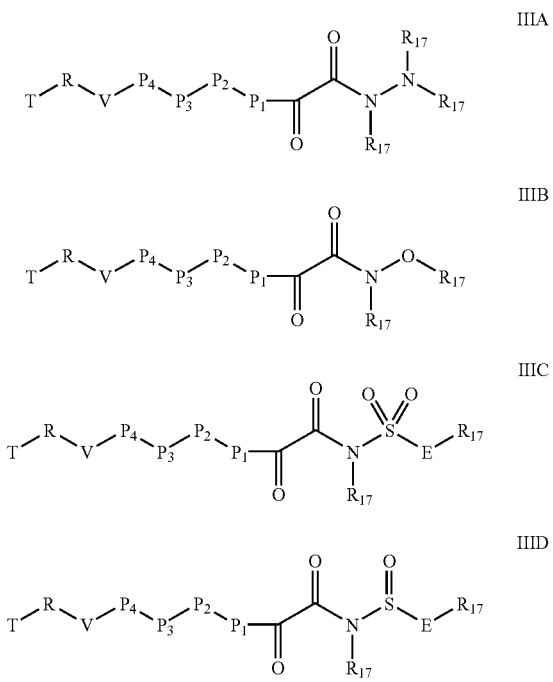

All compounds, therefore, having: 1) structural elements of a serine protease inhibitor; and 2) the diketohydrazide moiety (IIIA), or the diketohydroxamate moiety (IIIB), or the diketosulfonamide moiety (IIIC) or the diketosulfoxamide moiety (IIID) are considered part of this invention. Compounds having the structural elements of a serine protease inhibitor include, but are not limited to, the compounds of the following publications: WO 97/43310, US20020016294, WO 01/81325, WO 02/08198, WO 01/77113, WO 02/08187, WO 02/08256, WO 02/08244, WO 03/006490, WO 01/74768, WO 99/50230, WO 98/17679, WO 02/48157, US20020177725, WO 02/060926, US20030008828, WO 02/48116, WO 01/64678, WO 01/07407, WO 98/46630, WO 00/59929, WO 99/07733, WO 00/09588, US20020016442, WO 00/09543, WO 99/07734, U.S. Pat. No. 6,018,020, WO 98/22496, U.S. Pat. No. 5,866,684, WO 02/079234, WO 00/31129, WO 99/38888, WO 99/64442, and WO 02/18369, which are incorporated herein by reference.

Thus, any compound of the above publications may be modified to include the diketohydrazide moiety (IIIA), the diketohydroxamate moiety (IIIB), the diketosulfonamide moiety (IIIC) or the diketosulfoxamide moiety (IIID) moiety, or derivatives thereof. Any such compound is part of this invention. For example, compound A in WO 02/18369 (p. 41):

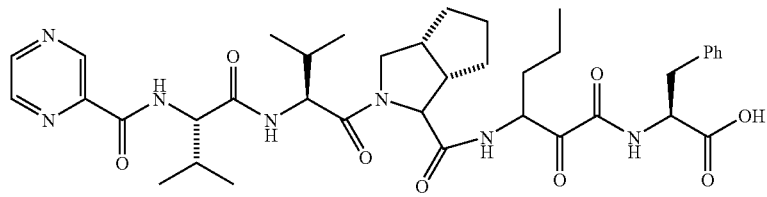

may be modified to provide the following compound of this invention:

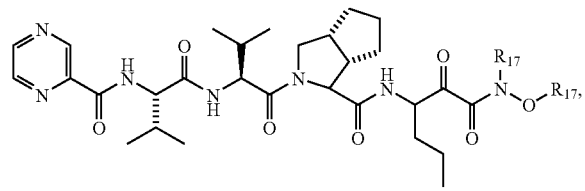

wherein $R_{17}$ is as defined in any of the embodiments herein.

In other forms of any embodiment of the present invention, compounds of formula IIIA-1, IIIB-1, IIIC-1, and IIID-1 are provided, wherein P1, P2, and P3 designate the residues of a serine protease inhibitor as known to those skilled in the art, E is selected from $N(R_{17})$ or a bond, and V, R, T, and $R_{17}$, are as defined in any of the embodiments herein.

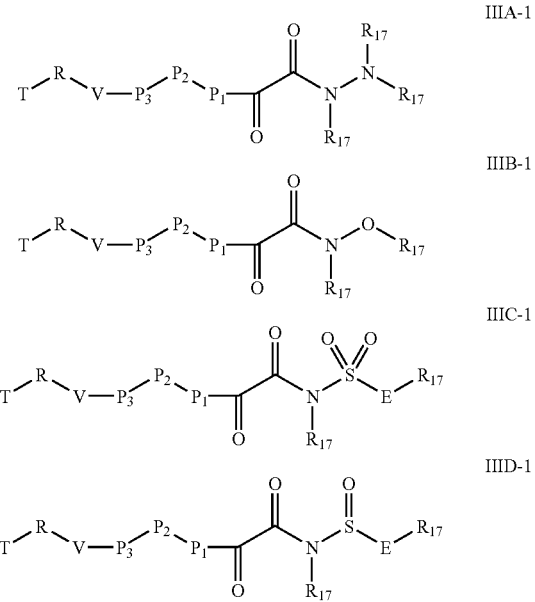

In other forms of any embodiment of this invention, $R_{11}$ is H; and
$R_{12}$ is
(C1-C6)-aliphatic,
(C3-C10)-cycloalkyl,
[(C3-C10)-cycloalkyl]-(C1-C12)-alkyl,
(C6-C10)-aryl,
(C6-C10)-aryl-(C1-C6)alkyl,
(C3-C10)-heterocyclyl,
(C6-C10)-heterocyclyl-(C1-C6)alkyl,
(C5-C10)-heteroaryl, or
(C5-C10)-heteroaryl-(C1-C6)-alkyl.

In other forms of any embodiment of this invention, $R_{12}$ is isobutyl, cyclohexyl, cyclohexylmethyl, benzyl, or phenylethyl.

In other forms of any embodiment of this invention, $R_{11}$ is:
(C1-C6)-aliphatic,
(C3-C10)-cycloalkyl,
[(C3-C10)-cycloalkyl]-(C1-C12)-alkyl,
(C6-C10)-aryl,
(C6-C10)-aryl-(C1-C6)alkyl;
(C3-C10)-heterocyclyl,
(C6-C10)-heterocyclyl-(C1-C6)alkyl,
(C5-C10)-heteroaryl, or
(C5-C10)-heteroaryl-(C1-C6)-alkyl; and
$R_{12}$ is H.

In other forms of any embodiment of this invention, $R_{11}$, and $R_{12}$ are H.

In other forms of any embodiment of this invention, the

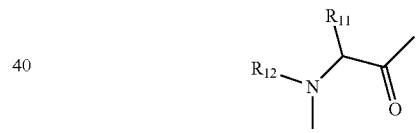

radical is:

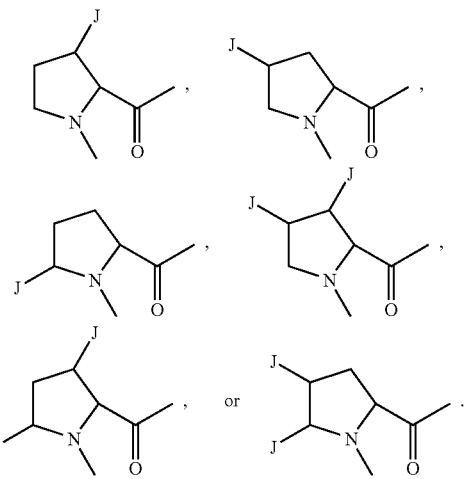

In other forms of any embodiment of this invention, the
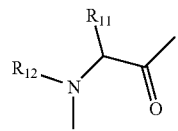
radical is:
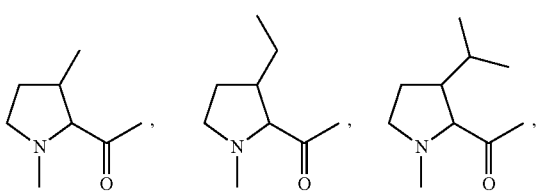
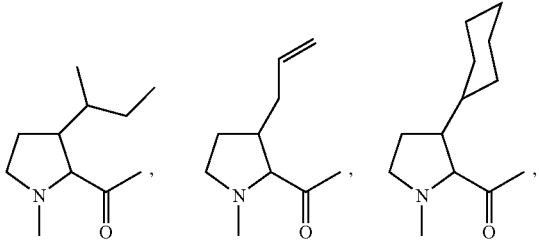
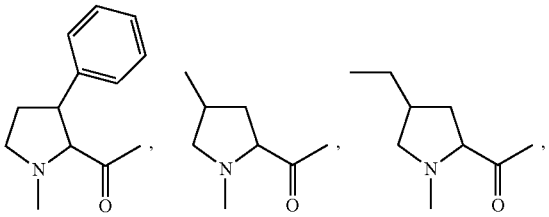
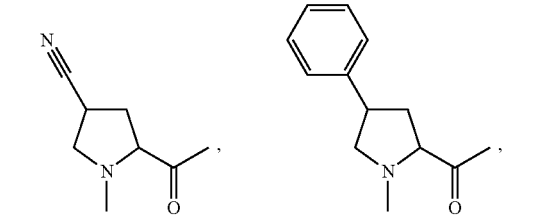
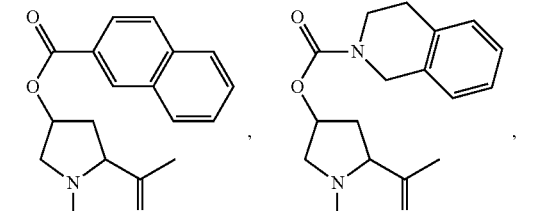
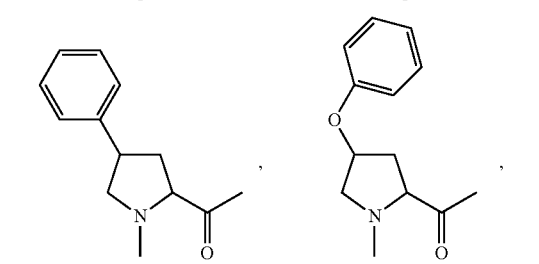
-continued
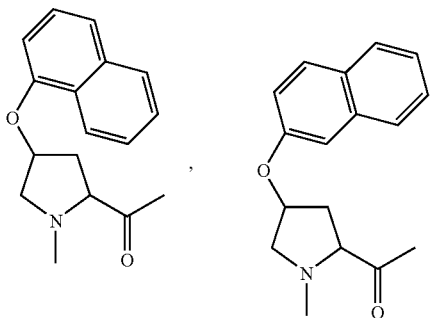
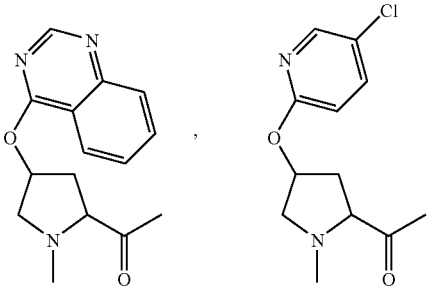
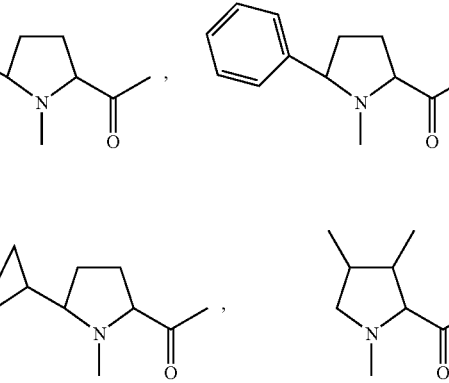
In other forms of any embodiment of this invention, the
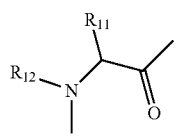

radical is:
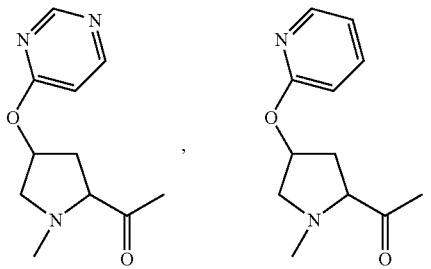
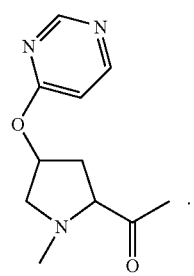
In other forms of any embodiment of this invention, the
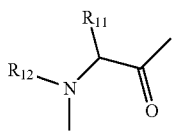
radical is:
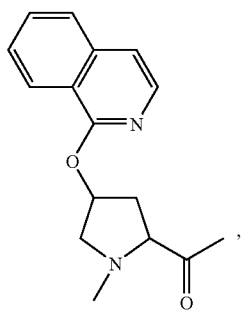 , 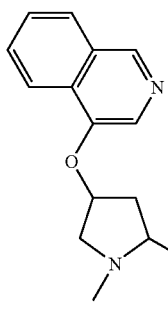 ,
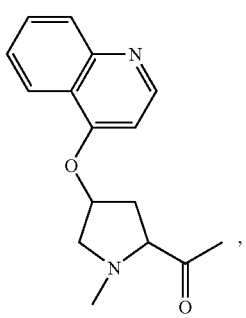 , 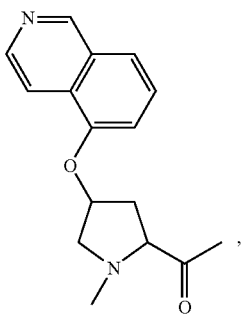 ,
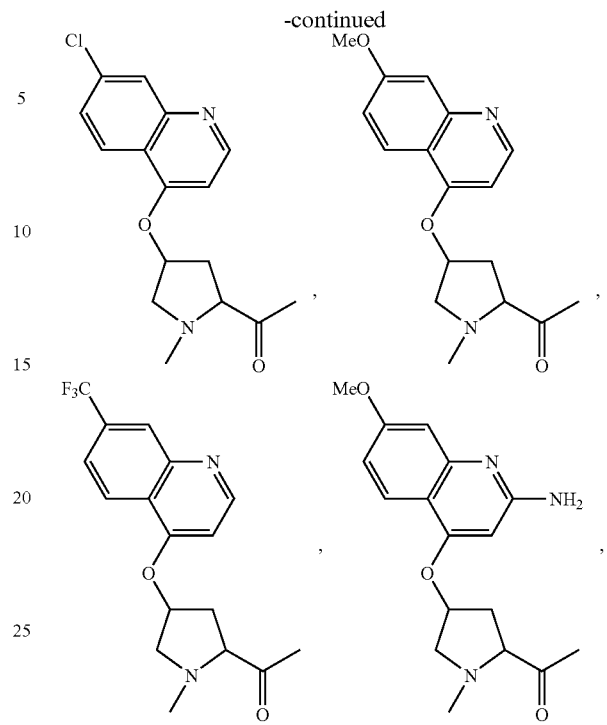
-continued
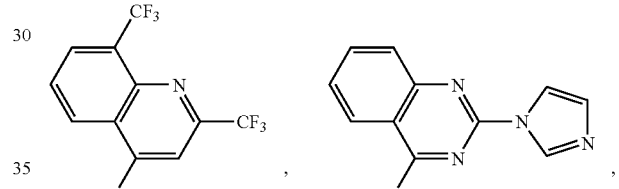
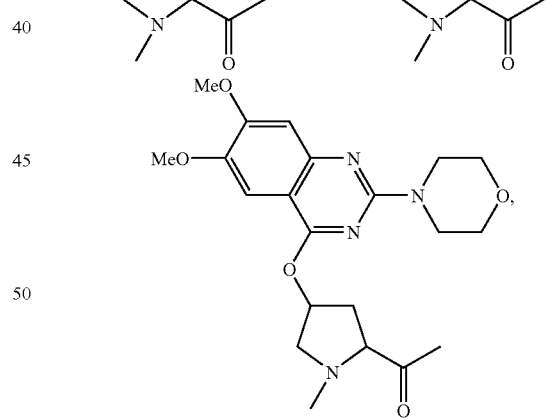
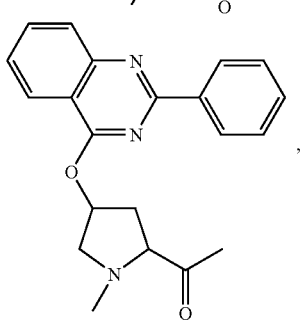

-continued
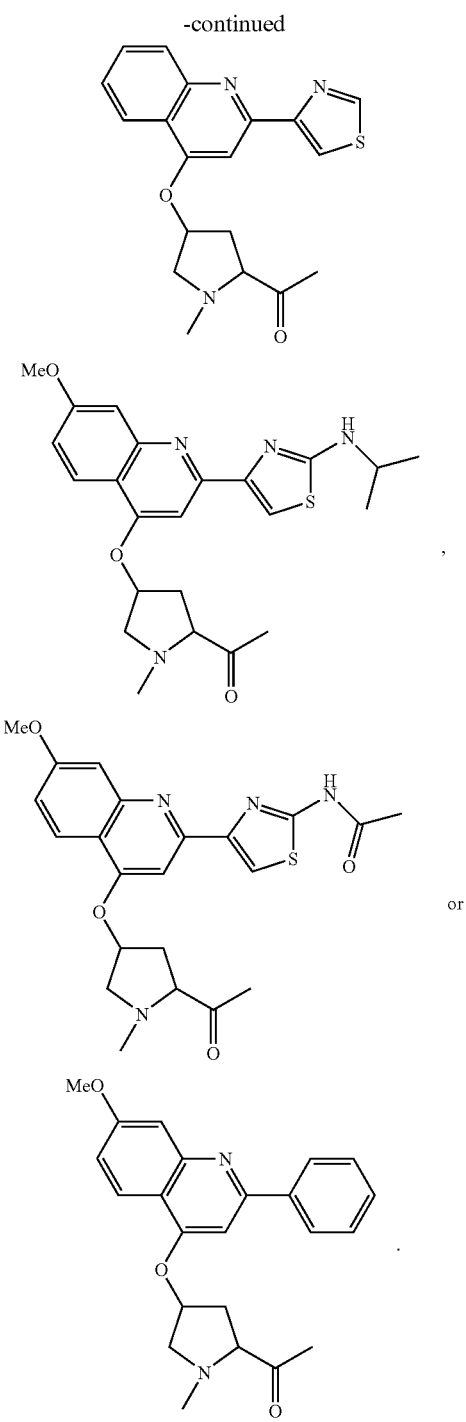
In other forms of any embodiment of this invention, the
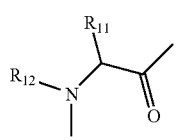
radical is:
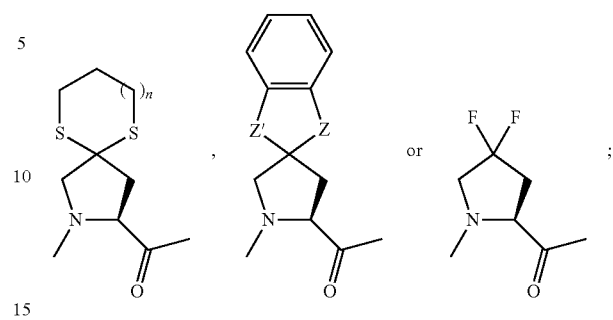
wherein n is 0 or 1 and Z and Z' are S or O.
In other forms of any embodiment of this invention, the
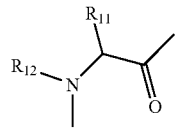
radical is:
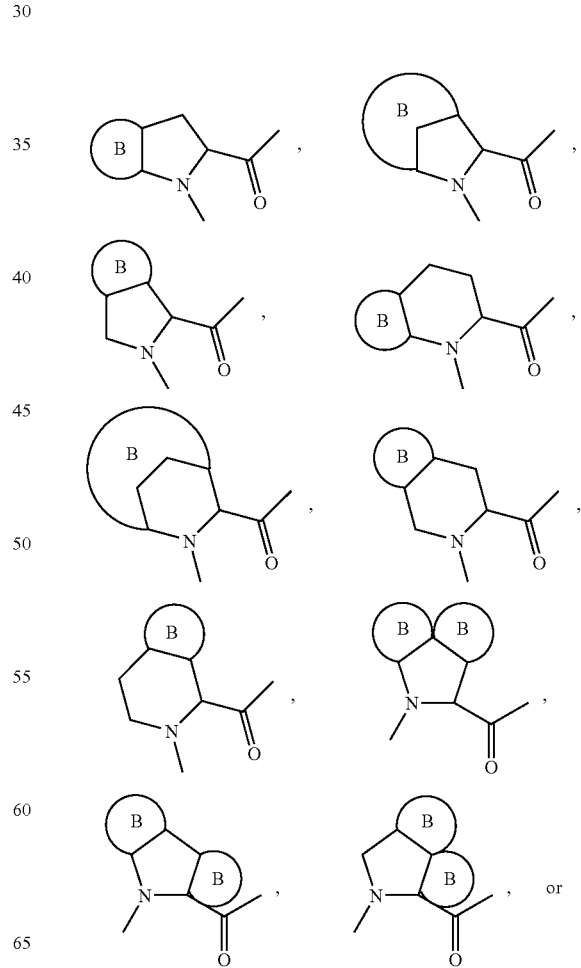

-continued

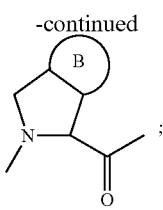

wherein each B independently forms a 3- to a 20-membered carbocyclic or heterocyclic ring system;
wherein each ring B is either aromatic or nonaromatic;
wherein each heteroatom in the heterocyclic ring system is N, NH, O, S, SO, or $SO_2$;
wherein, in the bi- and tri-cyclic ring system, each ring is linearly fused, bridged, or spirocyclic;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J.

In other forms of any embodiment of this invention, the

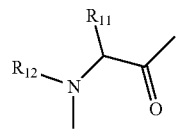

radical is:

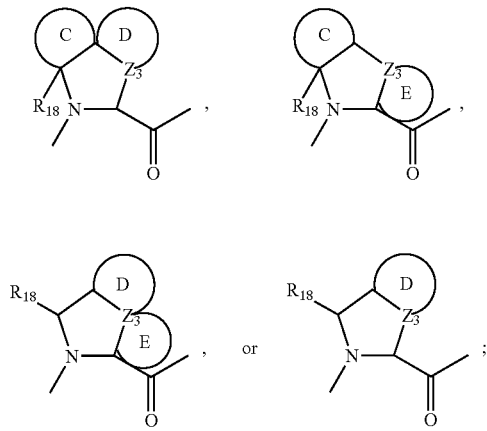

wherein each ring C, D, and E are as defined above for ring B and $Z_3$ is a carbon atom, —$CHR_{18}$—N—, —HN—$CR_{18}$— or —$CHR_{18}$—$CHR_{18}$—, —O—$CHR_{18}$—, —S—$CHR_{18}$—, —SO—$CHR_{18}$—, —$SO_2$—$CHR_{18}$—, or —N—. In another embodiment, $R_{18}$ is (C1-C12)-aliphatic, (C6-C10)-aryl, (C6-C10)aryl-(C1-C12)-aliphatic, or (C3-C10)-cycloalkyl. In another embodiment $R_{18}$ is (C1-C6)-alkyl or (C3-C7)-cycloalkyl.

In other forms of any embodiment of this invention, in the

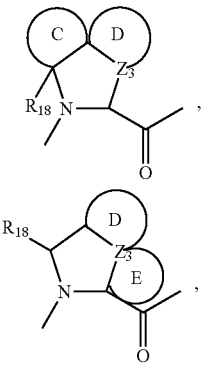
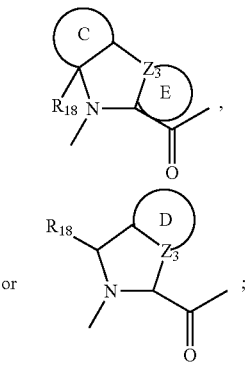

radical, ring C is:

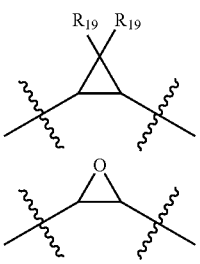
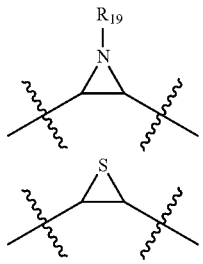

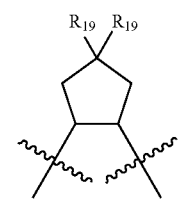
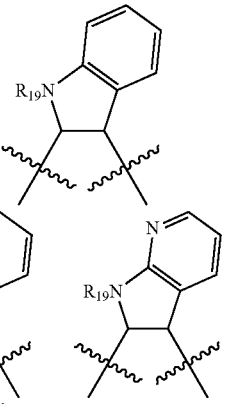

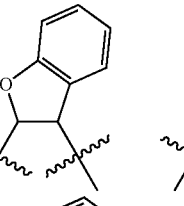
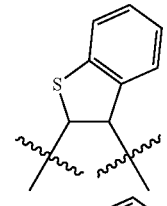

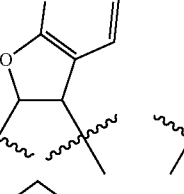
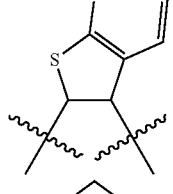

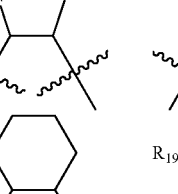
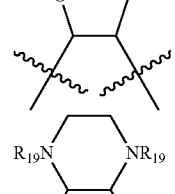

-continued
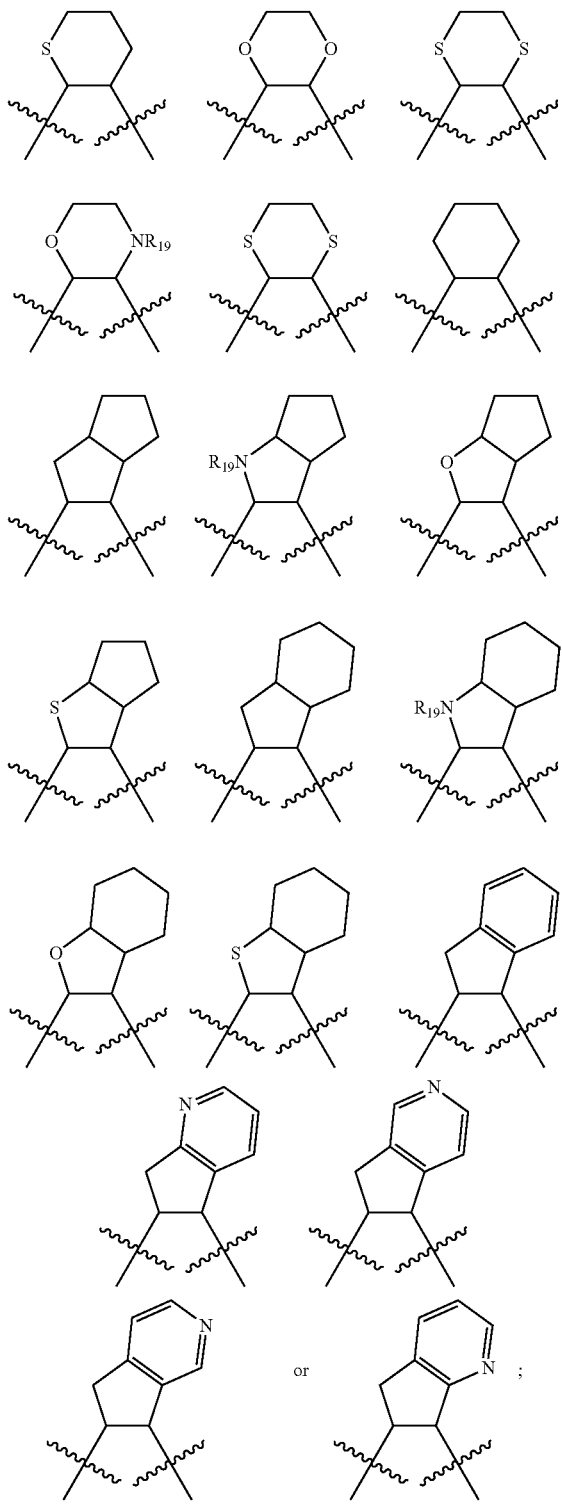
wherein R$_{19}$ is:
(C1-C12)-aliphatic-,
(C3-C10)-cycloalkyl or -cycloalkenyl-,
(C6-C10)-aryl-, or
(C6-C10)-aryl-(C1-C12)aliphatic-.
In other forms of any embodiment of this invention, in the
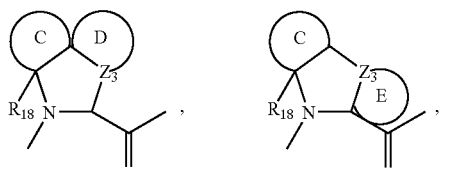
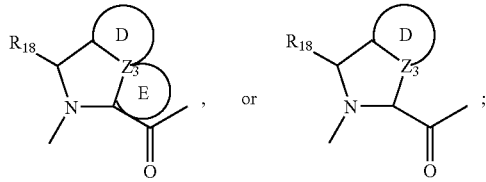
radical, ring C is:
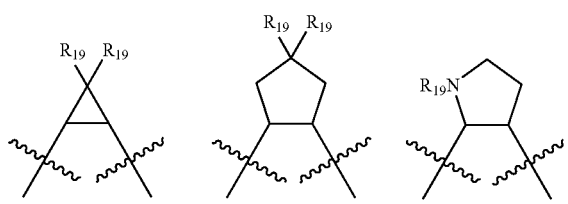
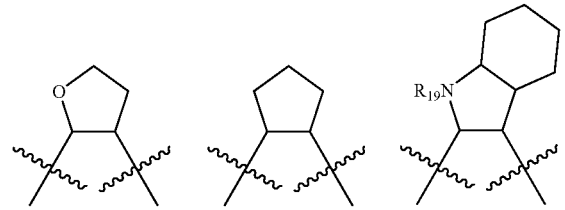
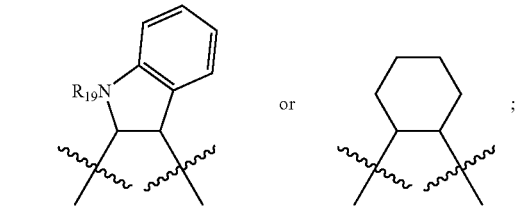
wherein R$_{19}$ is:
(C1-C12)-aliphatic-,
(C3-C10)-cycloalkyl or -cycloalkenyl-,
(C6-C10)-aryl-, or
(C6-C10)-aryl-(C1-C12)aliphatic-.
In other forms of any embodiment of this invention, in the
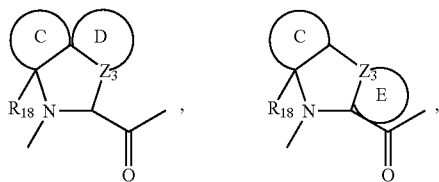

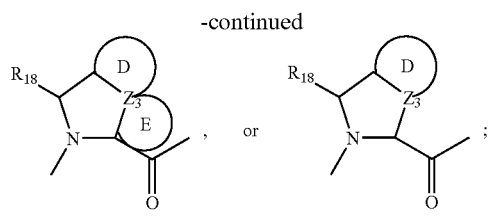
radical, ring D is selected from:
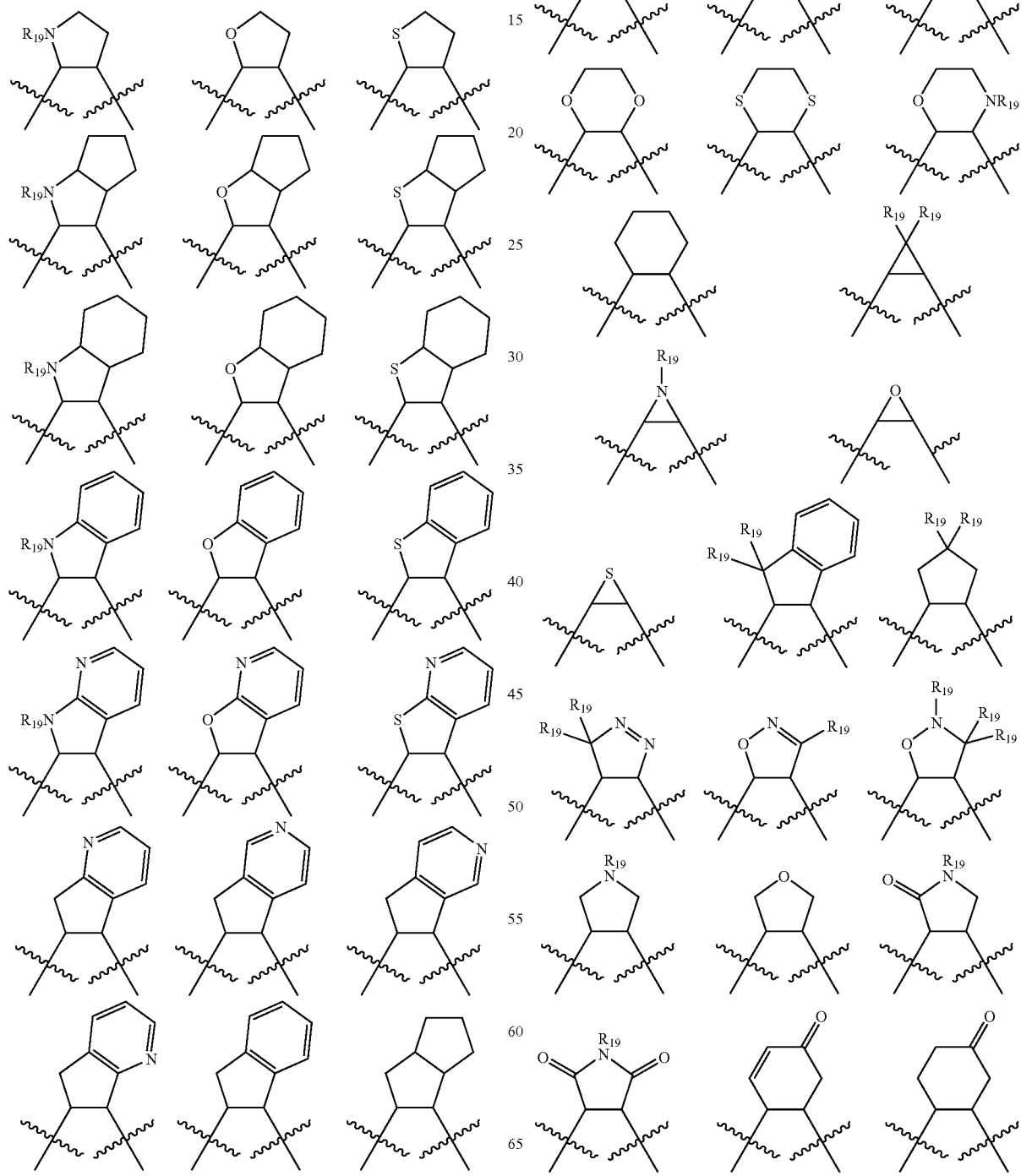

-continued

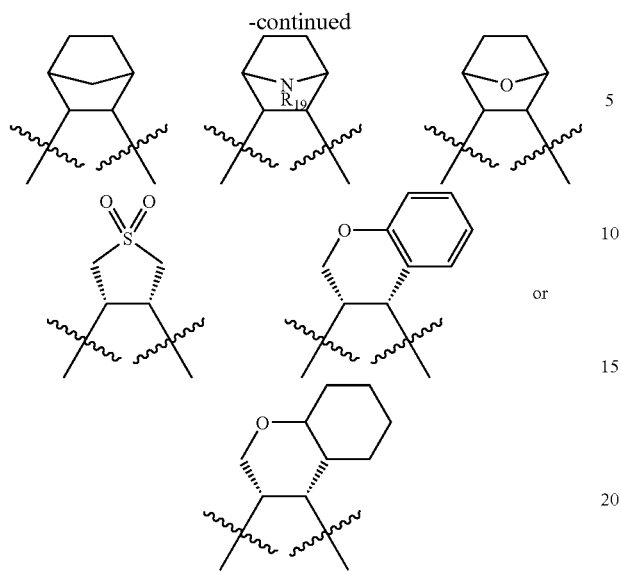

wherein R$_{19}$ is:
(C1-C12)-aliphatic-,
(C3-C10)-cycloalkyl or -cycloalkenyl-,
(C6-C10)-aryl-, or
(C6-C10)-aryl-(C1-C12)aliphatic-.

In other forms of any embodiment of this invention, in the radical, ring D is selected from:

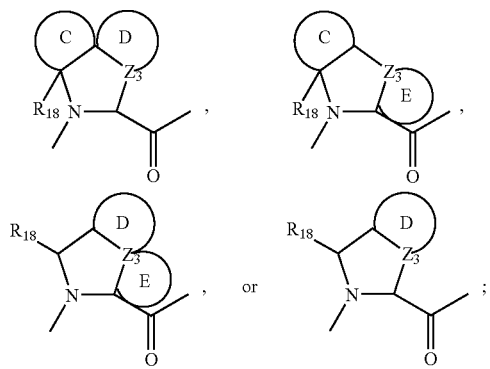

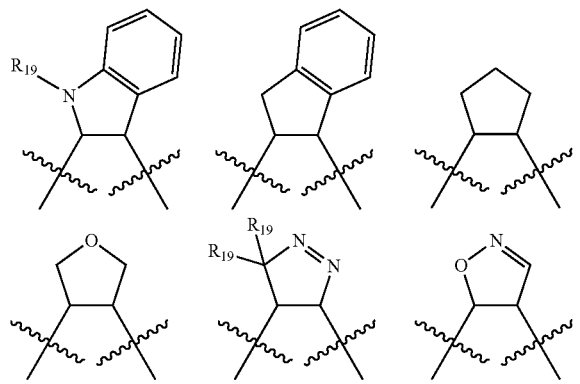

-continued

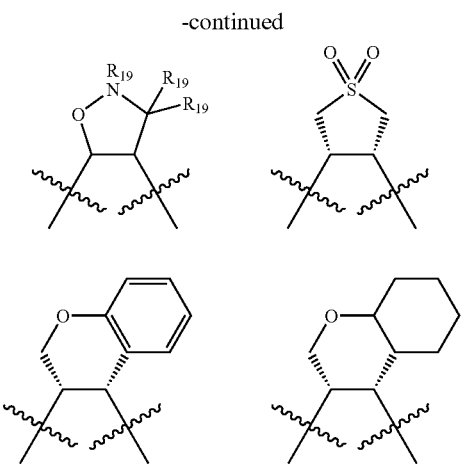

wherein R$_{19}$ is:
(C1-C12)-aliphatic-,
(C3-C10)-cycloalkyl or -cycloalkenyl-,
(C6-C10)-aryl-, or
(C6-C10)-aryl-(C1-C12)aliphatic-.

In other forms of any embodiment of this invention, rings A and B, together with the ring connected thereto include:

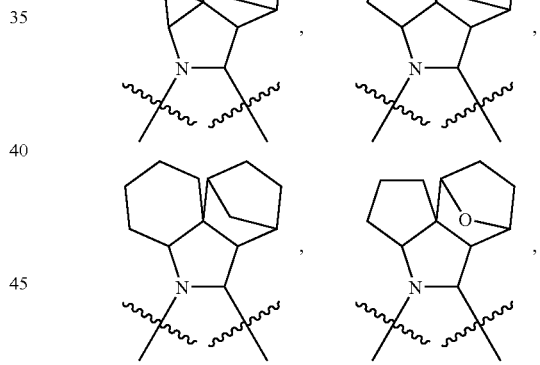

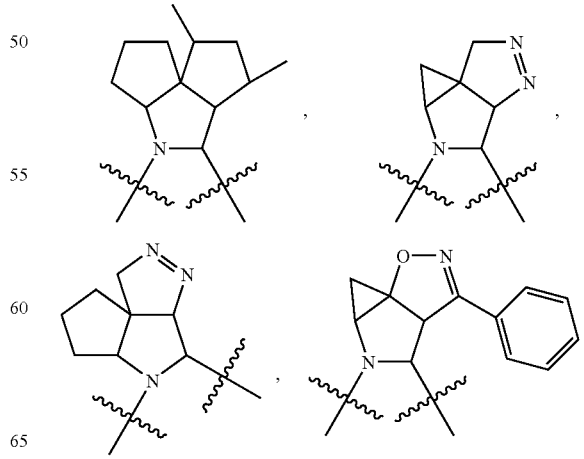

-continued
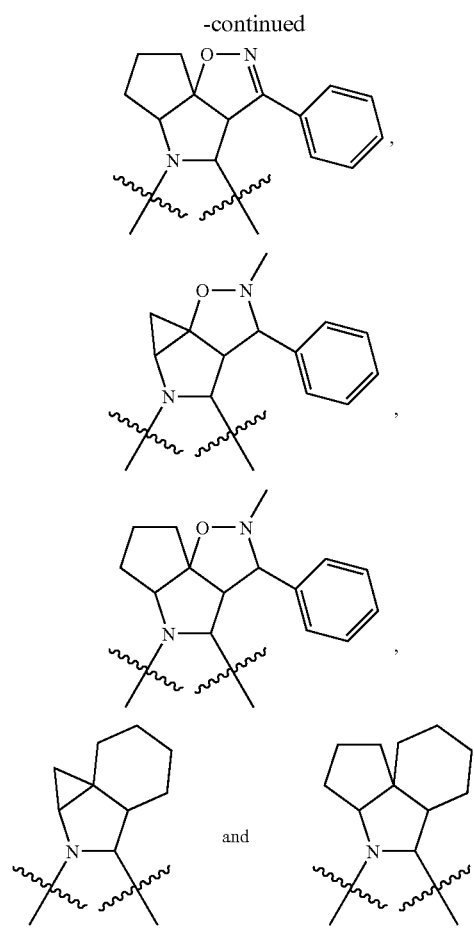
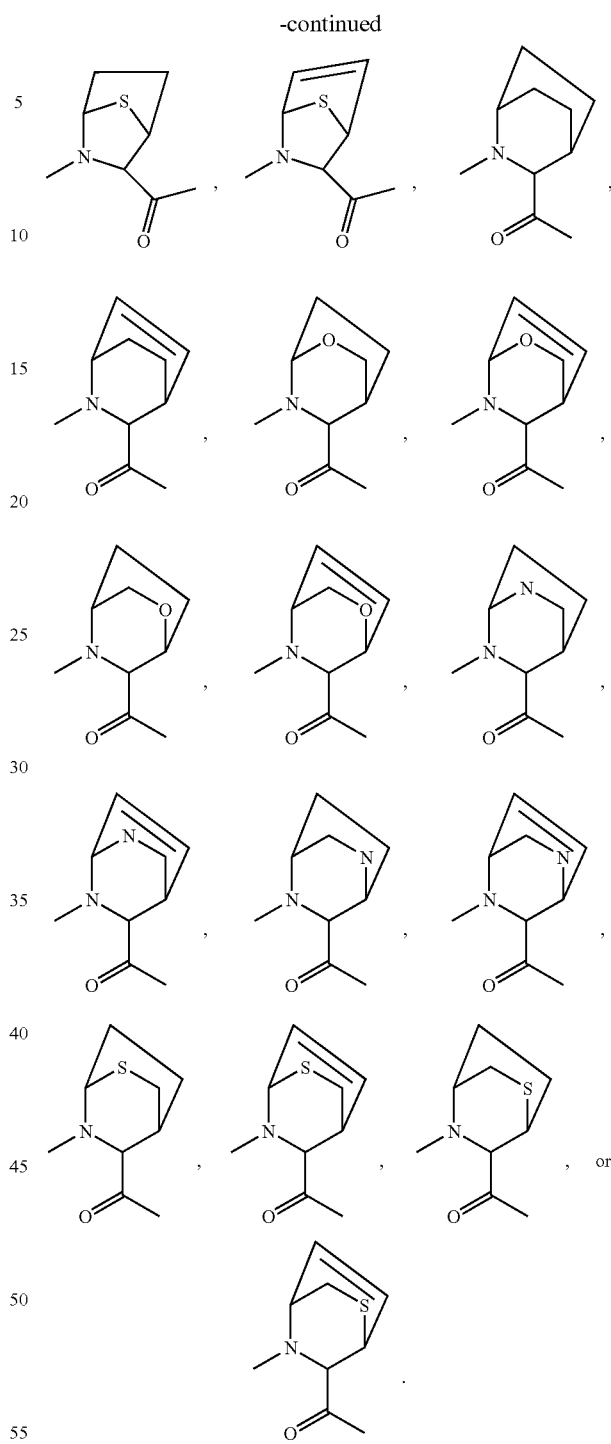
In other forms of any embodiment of this invention, the
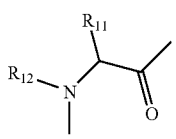
radical is:
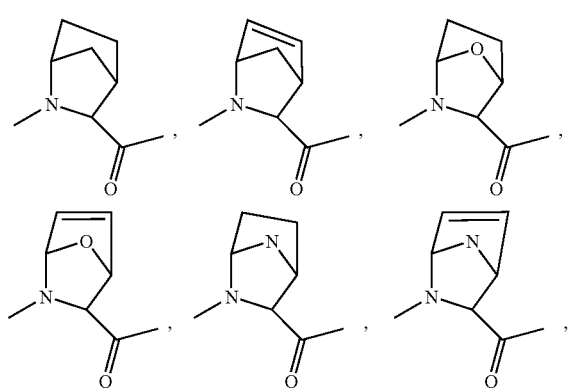
In other forms of any embodiment of this invention, the
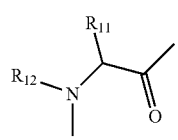

radical is:
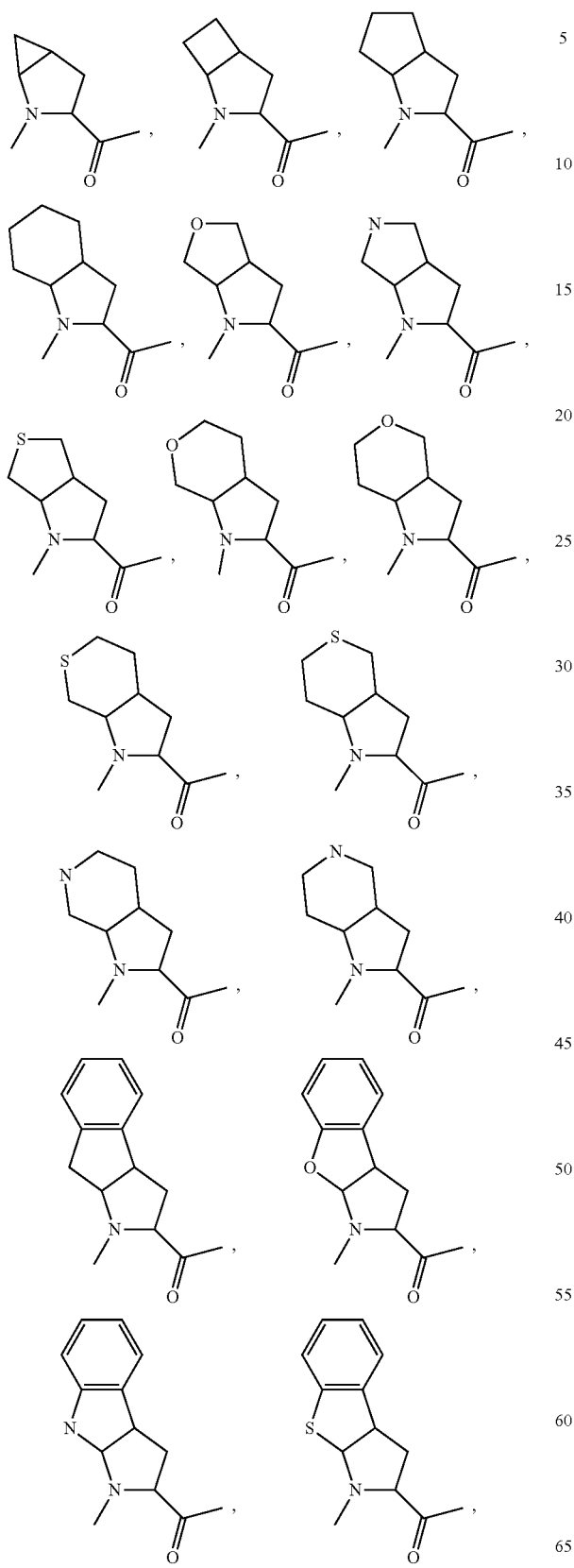
-continued
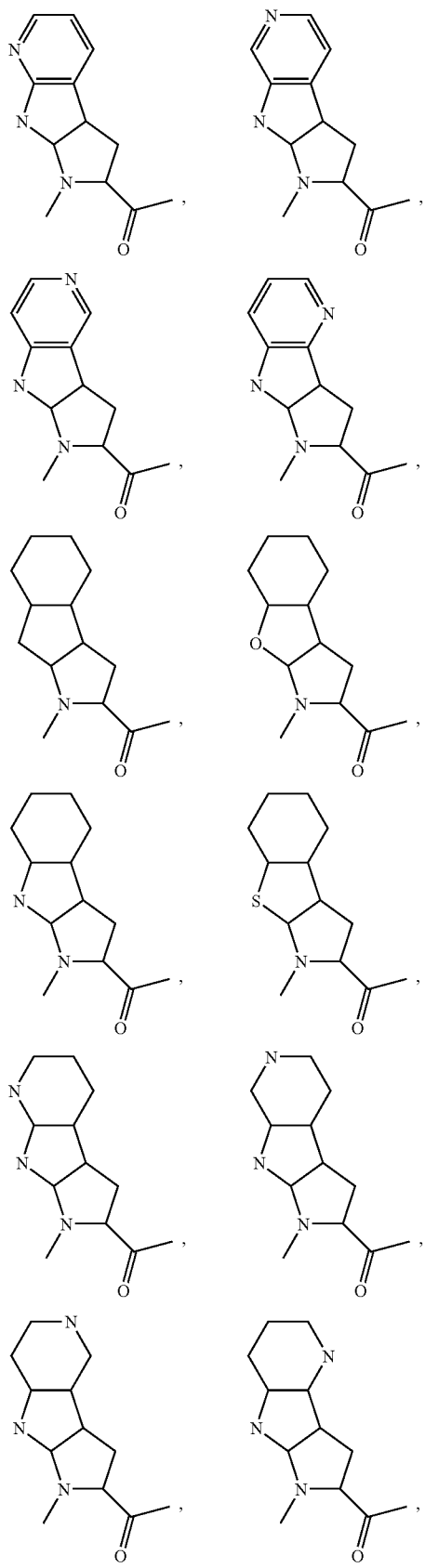

-continued
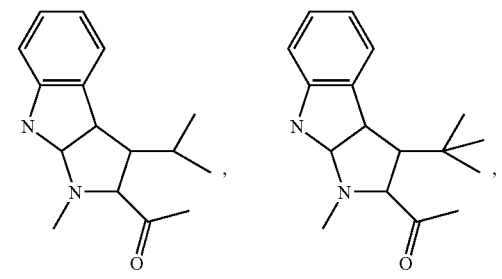
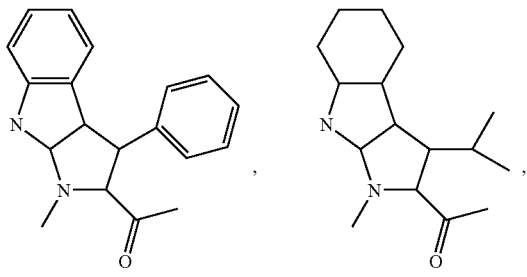
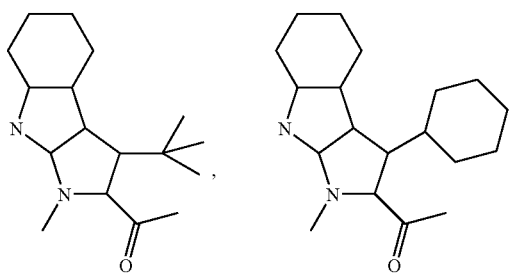
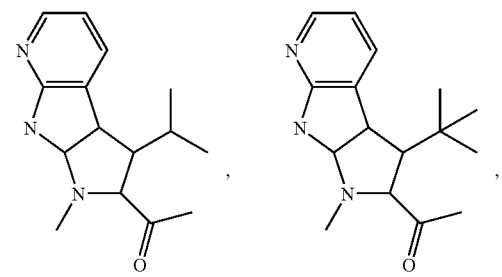
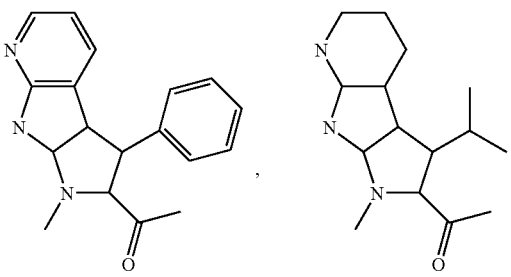
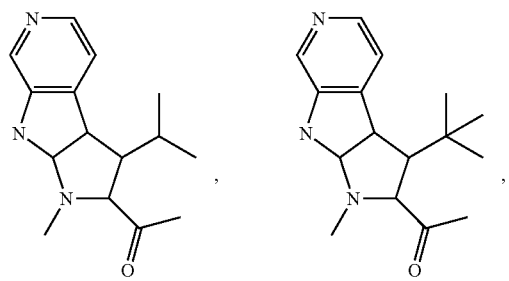
-continued
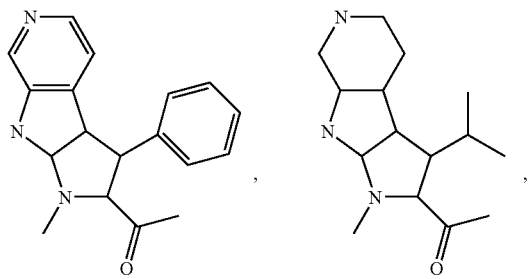
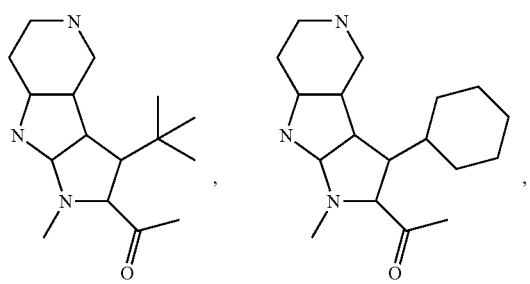
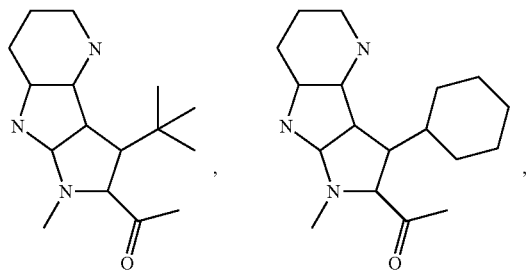
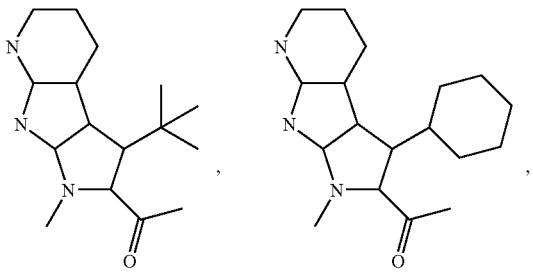
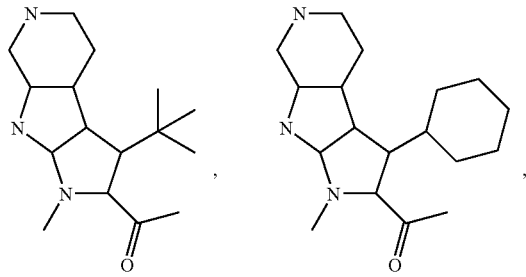
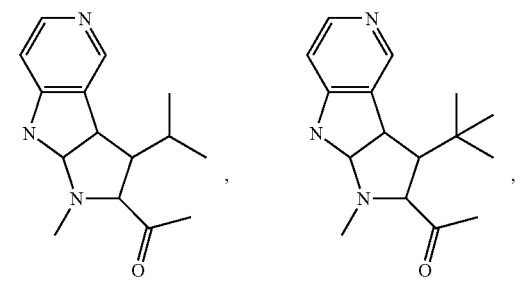

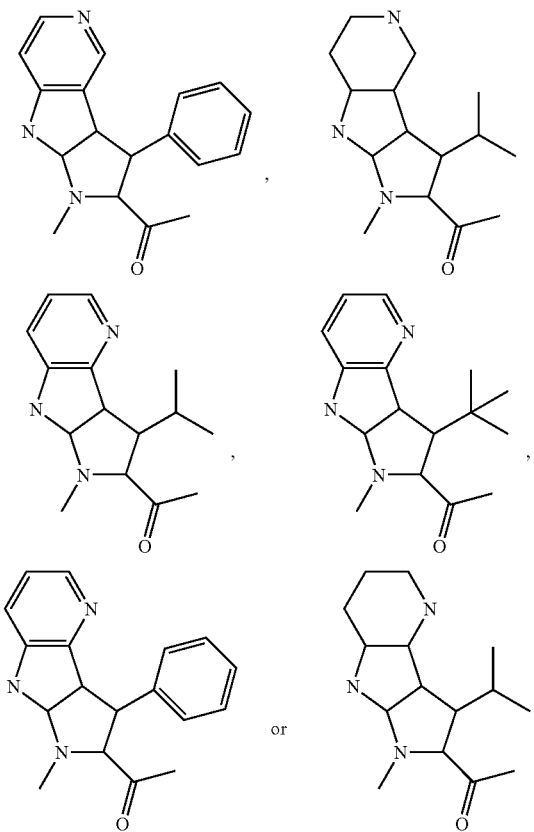
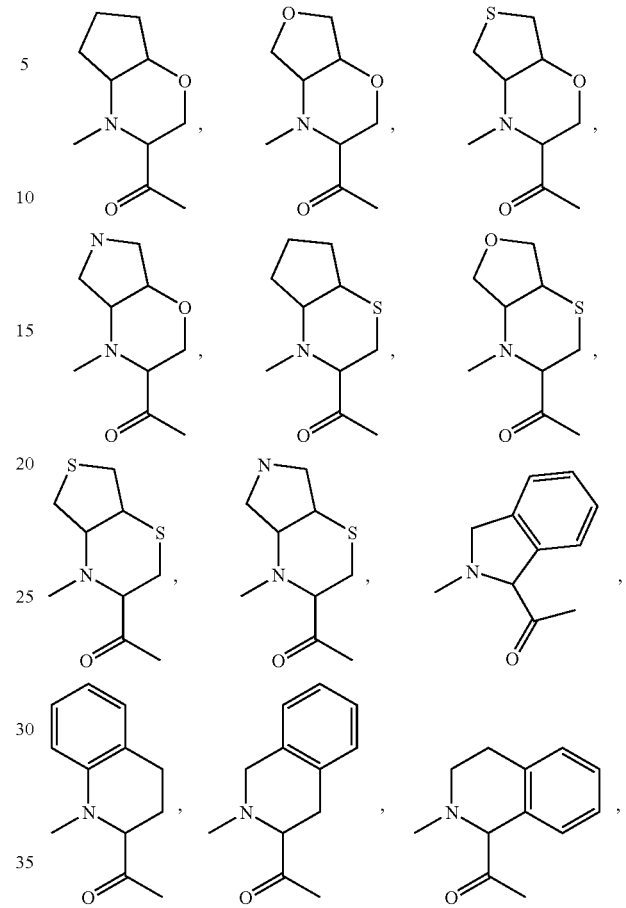
In other forms of any embodiment of this invention, the
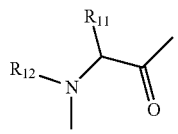
radical is:
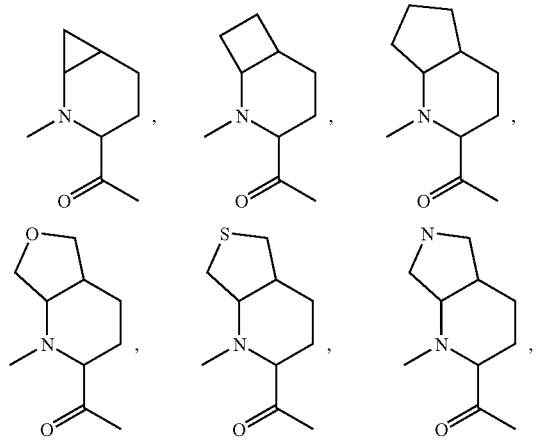
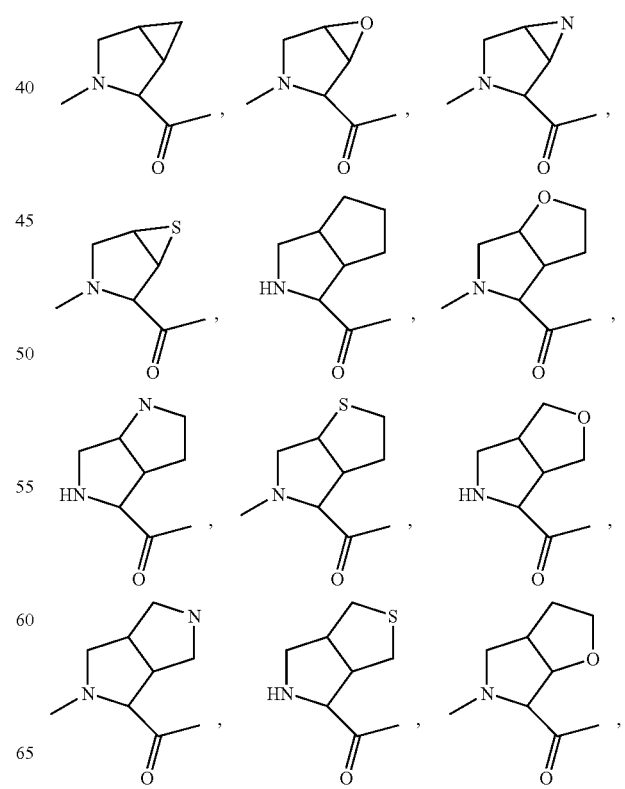

-continued
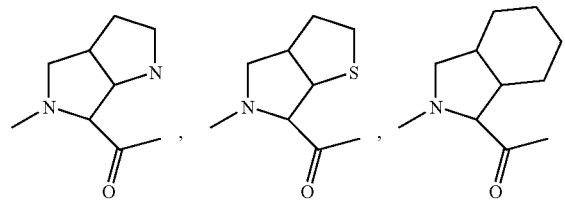
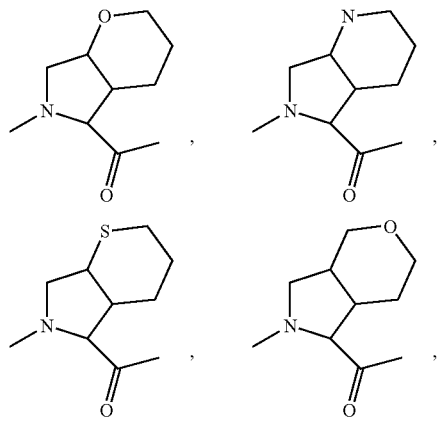
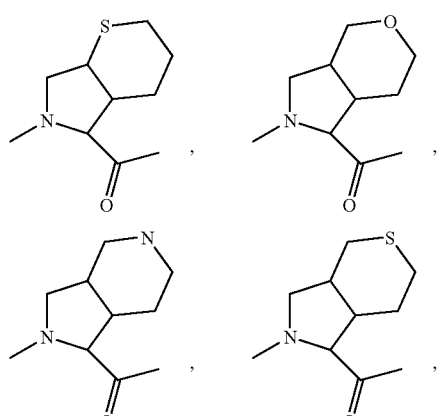
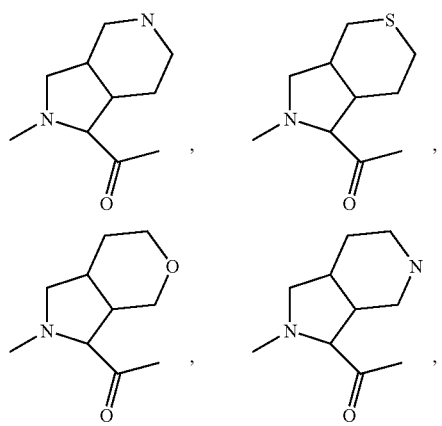
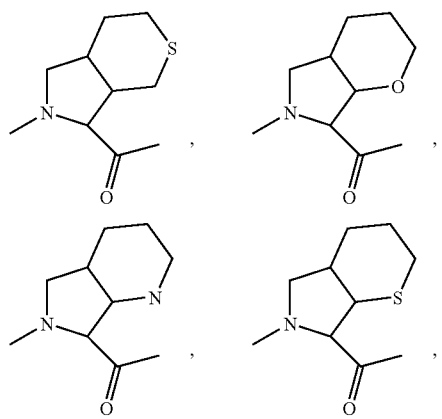
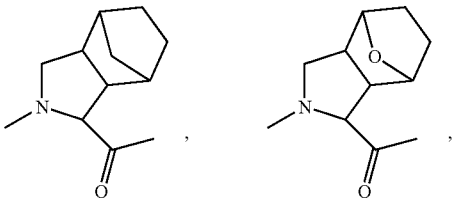
-continued
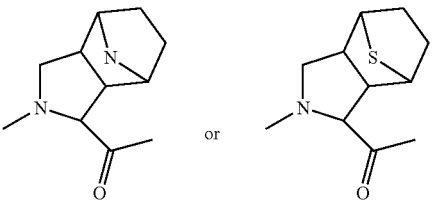 or .
In other forms of any embodiment of this invention, the
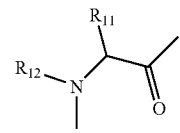
radical is:
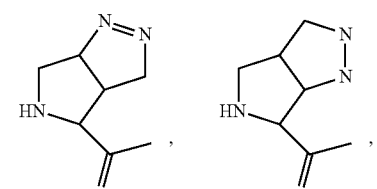
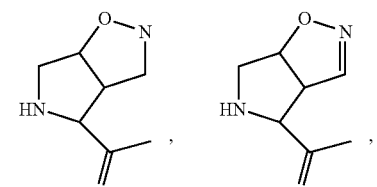
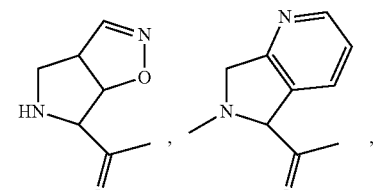
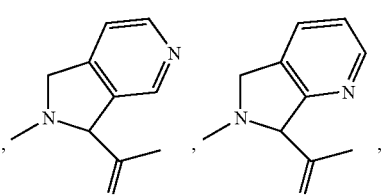
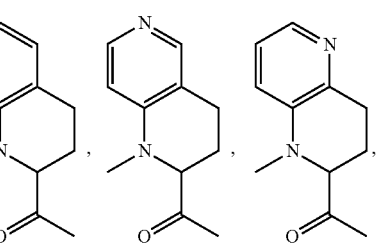

-continued
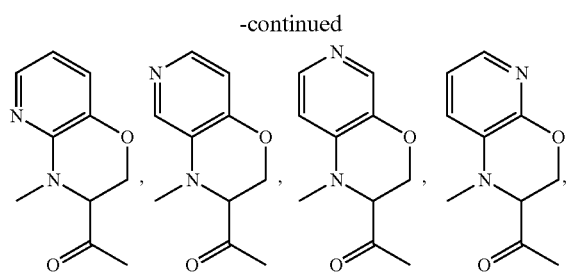
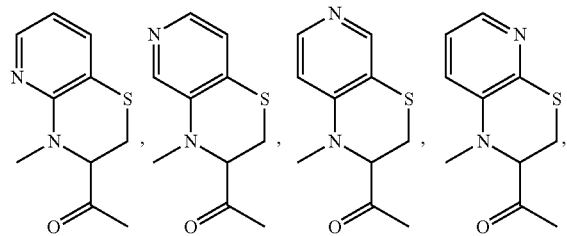
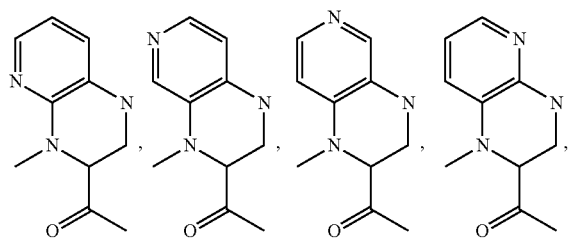
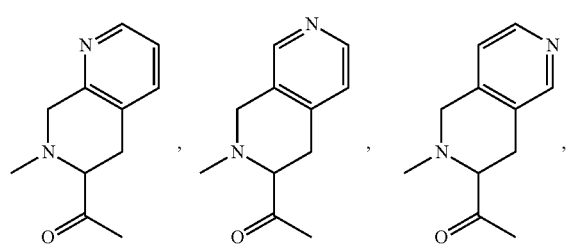
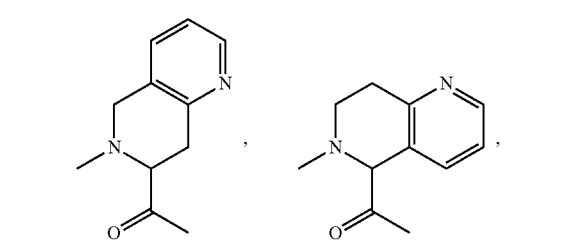
In other forms of any embodiment of this invention, the
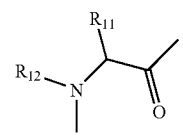
radical is:
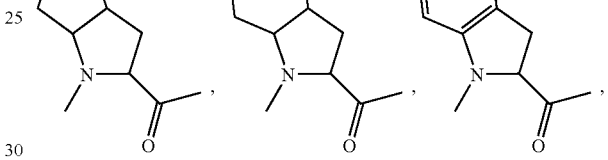
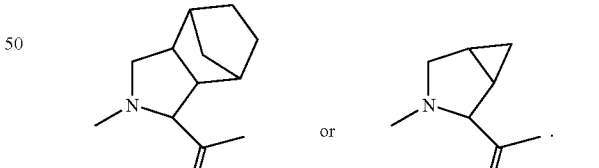
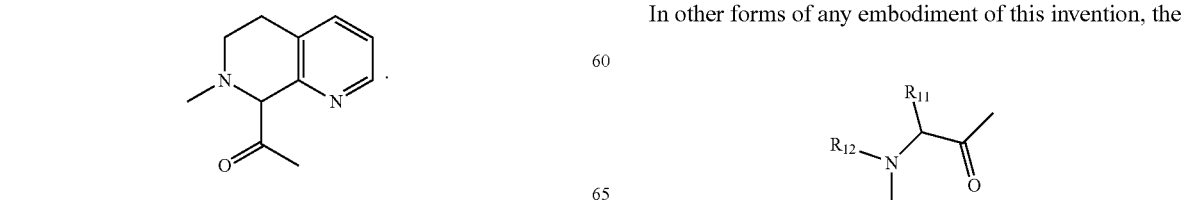
In other forms of any embodiment of this invention, the
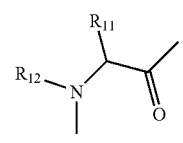

radical is:

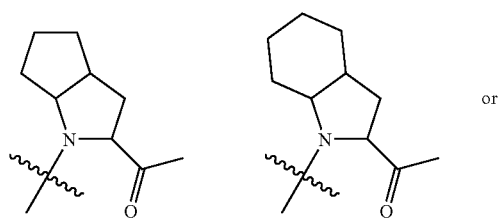 or 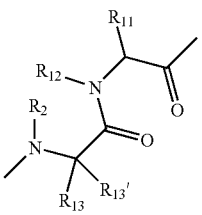

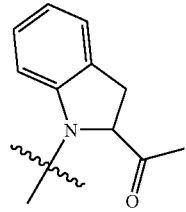

In other forms of any embodiment of this invention, the

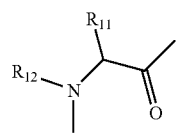

radical is:

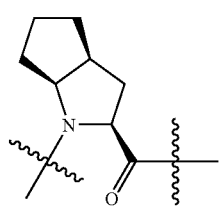 or 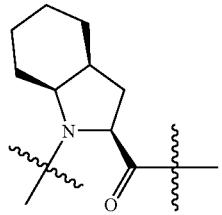

In other forms of any embodiment of this invention, the

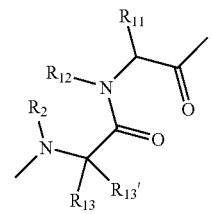 radical is: 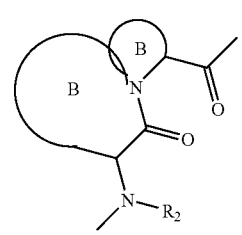 ;

wherein each B independently forms a 3- to a 20-membered carbocyclic or heterocyclic ring system;
wherein each ring B is either aromatic or nonaromatic;
wherein each heteroatom in the heterocyclic ring system is N, NH, O, S, SO, or $SO_2$;
wherein each ring is optionally fused to a (C6-C10)aryl, (C5-C10)heteroaryl, (C3-C10)cycloalkyl, or (C3-C10)heterocyclyl; and
wherein each ring is optionally substituted with up to 3 substituents selected independently from J.

In other forms of any embodiment of this invention, the

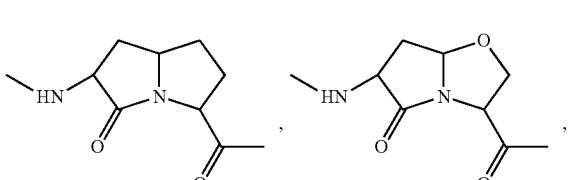

radical is:

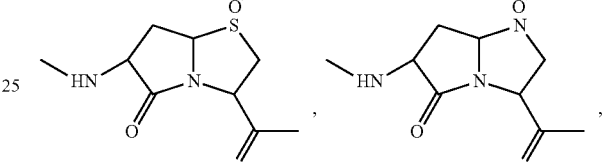,

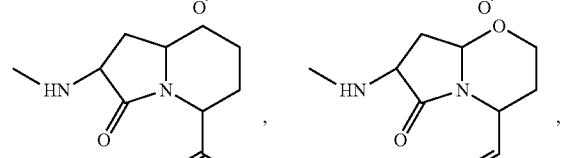,

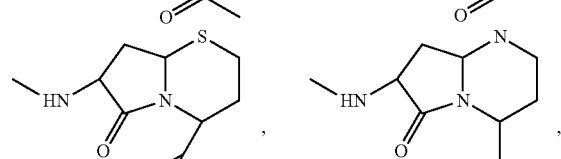,

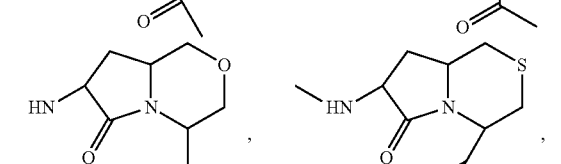,

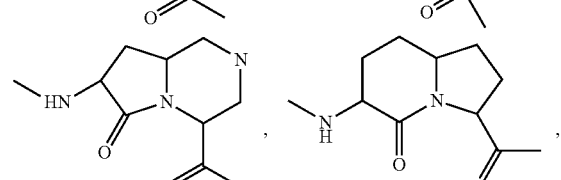,

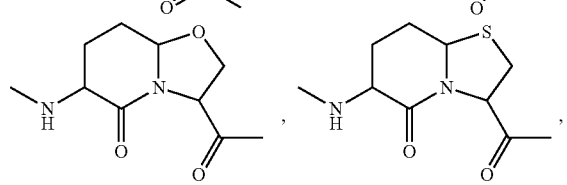,

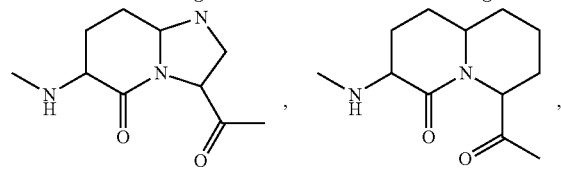,

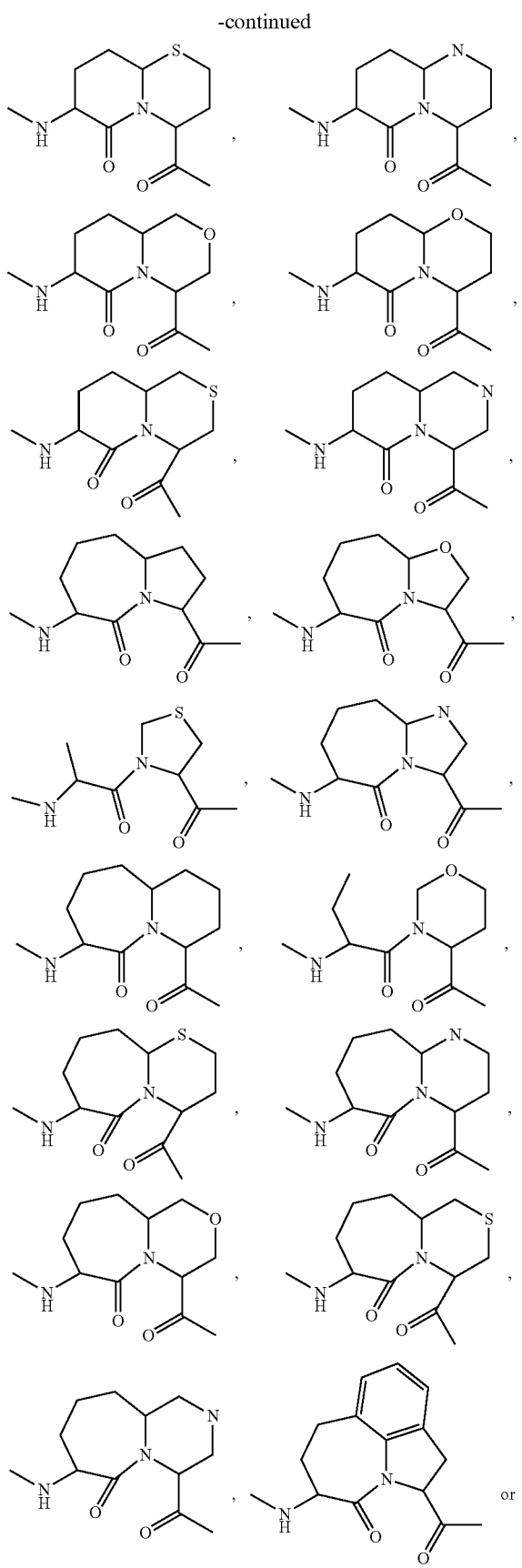
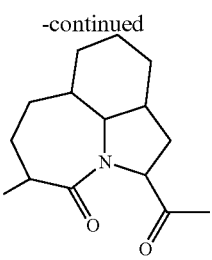
In other forms of any embodiment of this invention, the
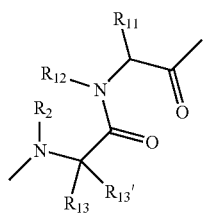
radical is:
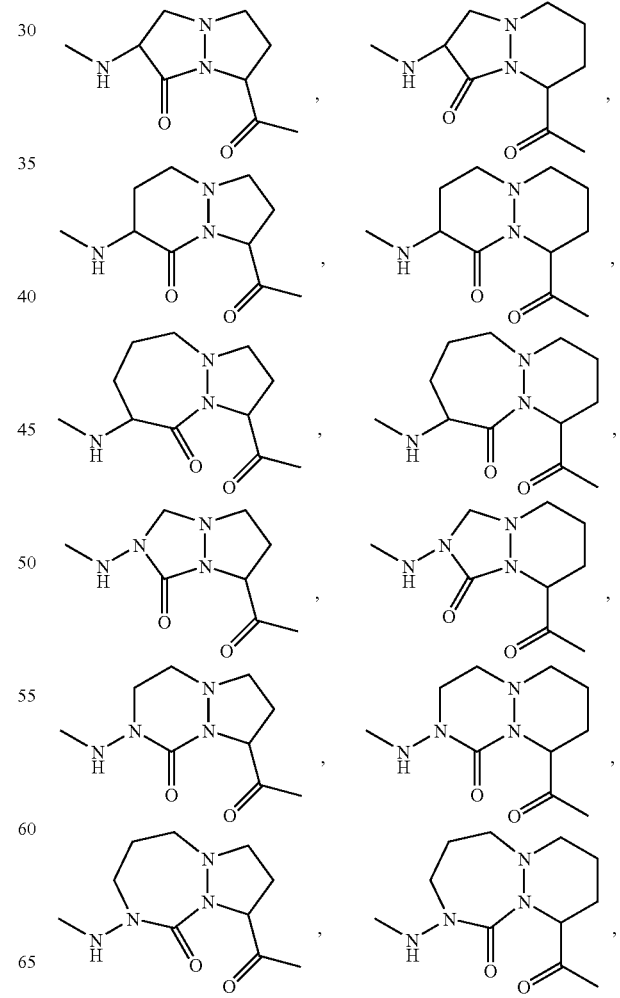

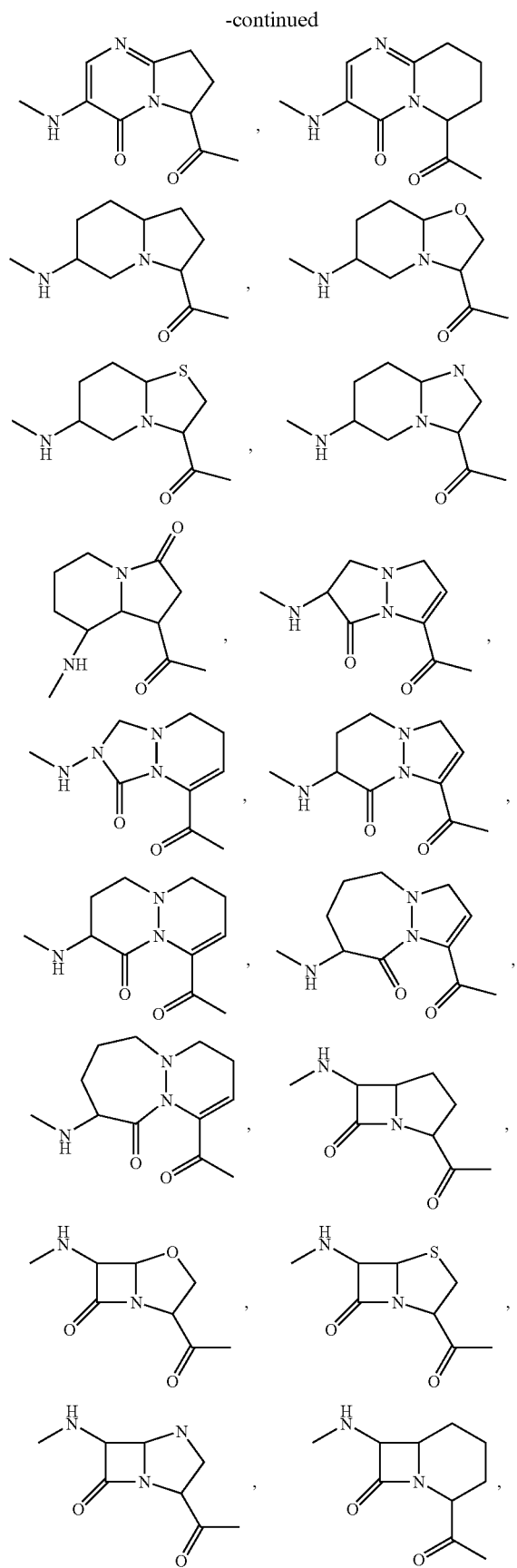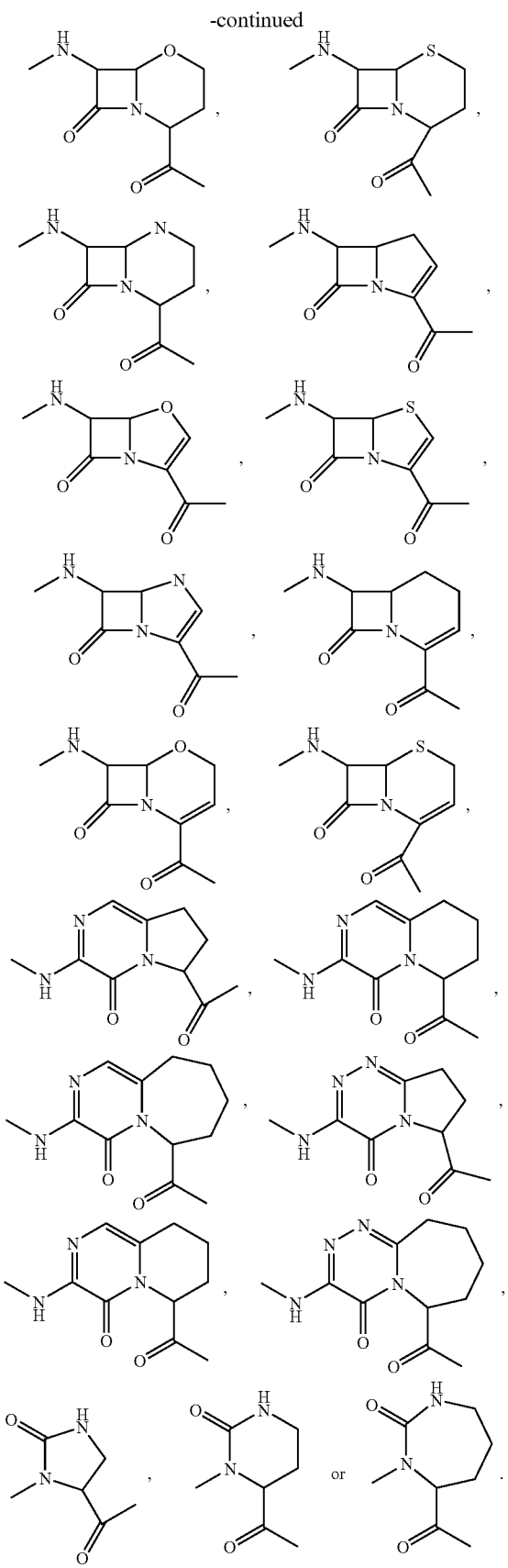

In other forms of any embodiment of this invention, the

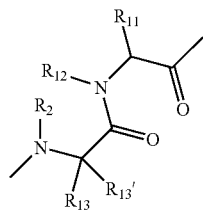

radical is:

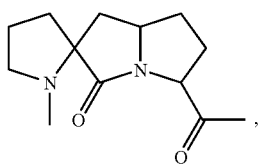 , 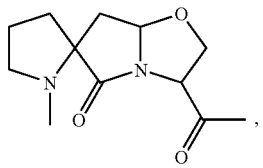 ,

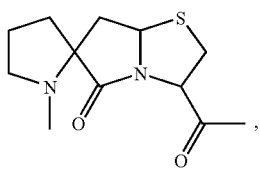 , 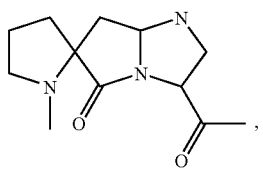 ,

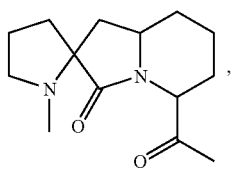 , 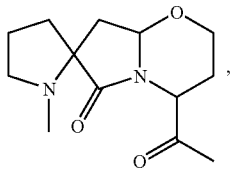 ,

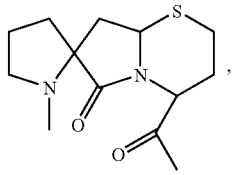 , 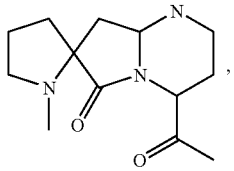 ,

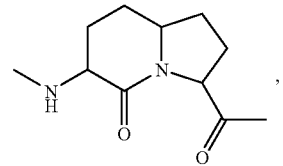 , 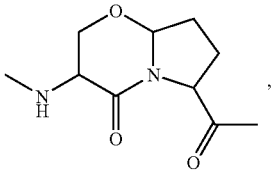 ,

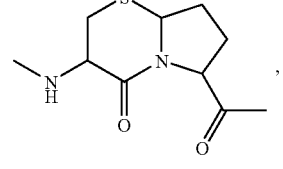 , 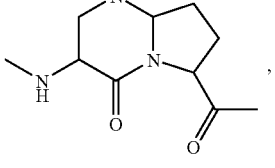 ,

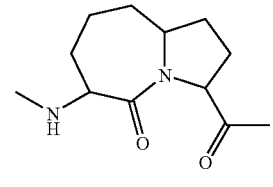 , 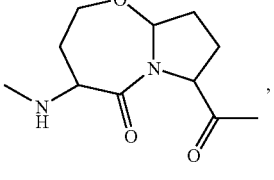 ,

-continued

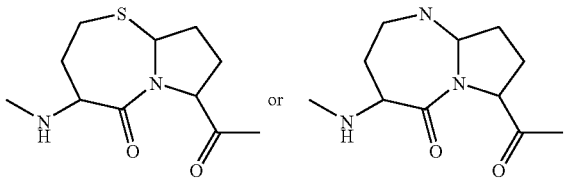

In other forms of any embodiment of this invention, the

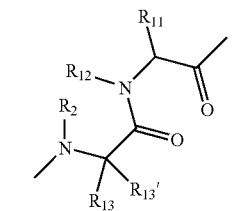

radical is:

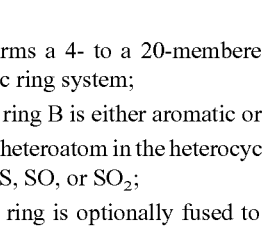

wherein B forms a 4- to a 20-membered carbocyclic or heterocyclic ring system;

wherein each ring B is either aromatic or nonaromatic;

wherein each heteroatom in the heterocyclic ring system is N, NH, O, S, SO, or $SO_2$;

wherein each ring is optionally fused to a (C6-C10)aryl, (C5-C10)heteroaryl, (C3-C10)cycloalkyl, or (C3-C10) heterocyclyl;

wherein, in the carbocyclic or heterocyclic ring system, each ring is linearly fused, bridged, or spirocyclic; and wherein each ring is optionally substituted with up to 3 substituents selected independently from J.

In other forms of any embodiment of this invention, the

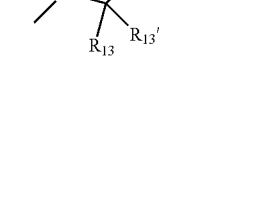

radical is:

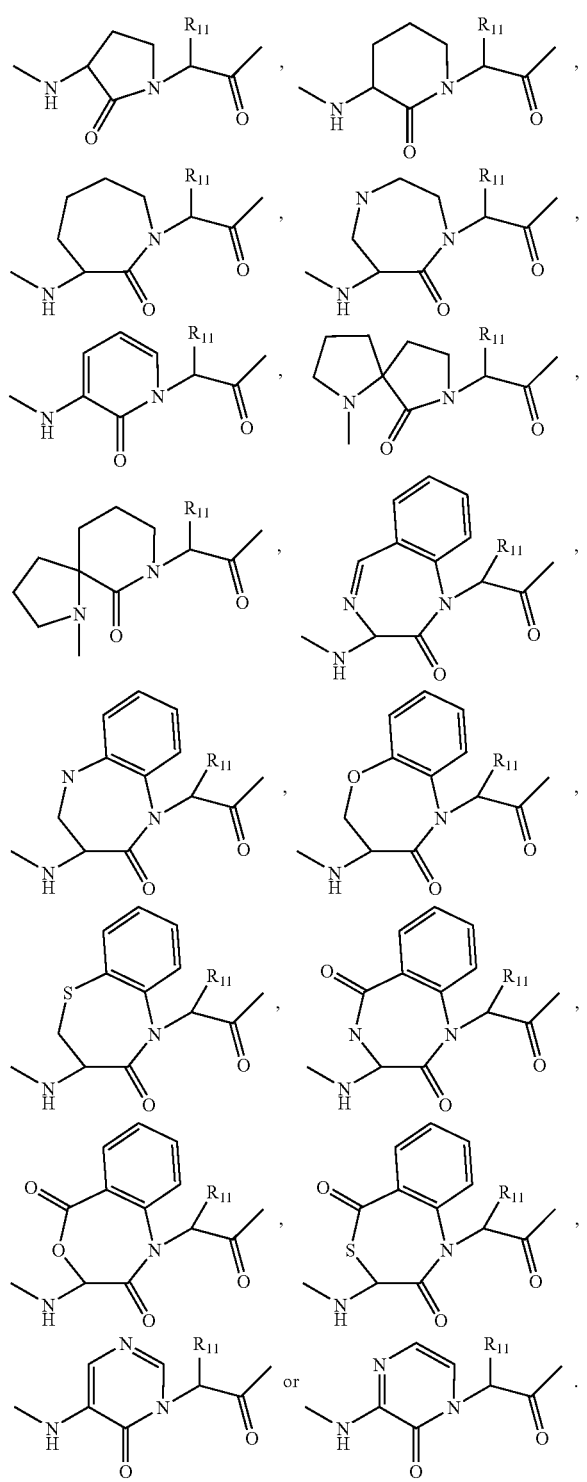

In the above radicals it is understood that the $R_{11}$ variable is H.

In other forms of any embodiment of this invention, $R_{11}$ and $R_{12}$ together with the atoms to which they are bound form a 6- to 10-membered mono- or bicyclic carbocyclic or heterocyclic ring system;

wherein each heteroatom in the heterocyclic ring system is selected from the group consisting of NH, O, S, SO, and $SO_2$; and wherein said ring has up to 3 substituents selected independently from J.

Any of the ring systems may be substituted as set forth herein. In other forms of any embodiment of this invention, the ring substituents are oxo, fluoro, difluoro (particularly vicininal difluoro), and hydroxy. In other forms of any embodiment of this invention, the following ring systems:

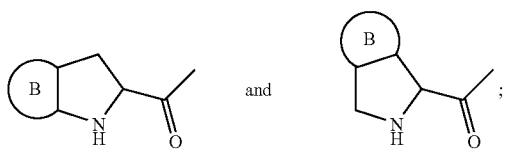

are optionally substituted with oxo, fluoro, difluoro (particularly vicininal difluoro), and hydroxy; wherein ring B is a 5-membered carbocyclic ring, optionally having one unsaturated bond.

In other forms of any embodiment of this invention, heteroatoms are selected from the group consisting of N, NH, O, SO, and $SO_2$.

In other forms of any embodiment of this invention, $R_{5'}$ is H and $R_5$ is (C1-C6)-aliphatic optionally substituted with 1 to 3 fluoro groups or 1 —SH group, or $R_5$ is (C6-C10)-aryl.

In other forms of any embodiment of this invention, the (C1-C6)-aliphatic issubstituted with 1 to 3 fluoro groups.

In other forms of any embodiment of this invention, $R_5$ and $R_{5'}$ are independently hydrogen or:

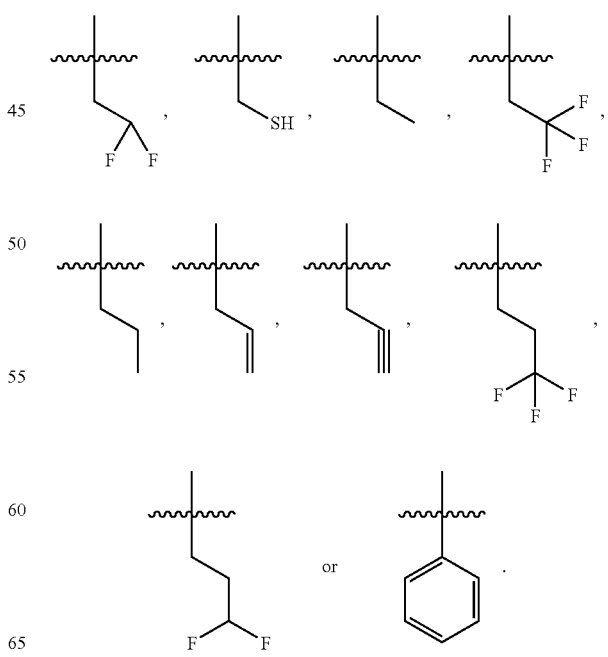

In other forms of any embodiment of this invention, $R_{5'}$ is H and $R_5$ is:

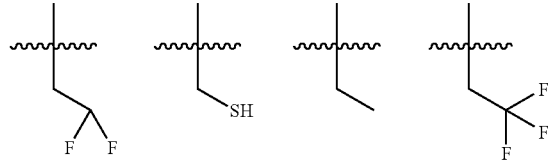

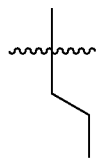

In other forms of any embodiment of this invention, $R_5$ and $R_{5'}$ is:

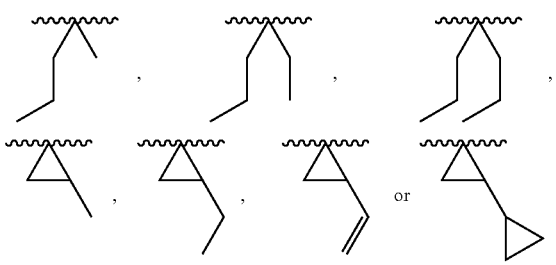

In other forms of any embodiment of this invention, $R_{13'}$ is hydrogen and
$R_{13}$ is:
 (C1-C6)-aliphatic,
 (C3-C10)-cycloalkyl,
 [(C3-C10)-cycloalkyl]-(C1-C12)-alkyl,
 (C6-C10)-aryl,
 (C6-C10)-aryl-(C1-C6)alkyl,
 (C3-C10)-heterocyclyl,
 (C6-C10)-heterocyclyl-(C1-C6)alkyl,
 (C5-C10)-heteroaryl, or
 (C5-C10)-heteroaryl-(C1-C6)-alkyl;
 wherein $R_{13}$ is optionally substituted with up to 3 substituents independently selected from J; and
 wherein up to 3 aliphatic carbon atoms in $R_{13}$ may be replaced by a heteroatom selected from O, NH, S, SO, or $SO_2$ in a chemically stable arrangement.

In other forms of any embodiment of this invention, $R_{13'}$ is hydrogen and $R_{13}$ is:

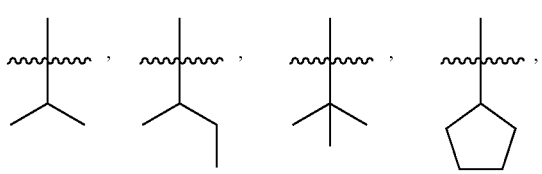

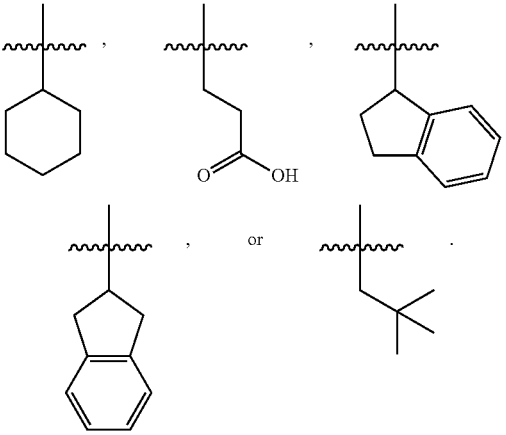

In other forms of any embodiment of this invention, $R_1$, if present, is:
 (C1-C6)-aliphatic,
 (C3-C10)-cycloalkyl,
 [(C3-C10)-cycloalkyl]-(C1-C12)-alkyl,
 (C6-C10)-aryl,
 (C6-C10)-aryl-(C1-C6)alkyl,
 (C3-C10)-heterocyclyl,
 (C6-C10)-heterocyclyl-(C1-C6)alkyl,
 (C5-C10)-heteroaryl, or
 (C5-C10)-heteroaryl-(C1-C6)-alkyl;
 wherein $R_1$ is optionally substituted with up to 3 substituents independently selected from J; and
 wherein up to 3 aliphatic carbon atoms in $R_1$ may be replaced by a heteroatom selected from O, NH, S, SO, or $SO_2$ in a chemically stable arrangement.

In other forms of any embodiment of this invention, $R_{1'}$, if present, is hydrogen and $R_1$, if present, is:

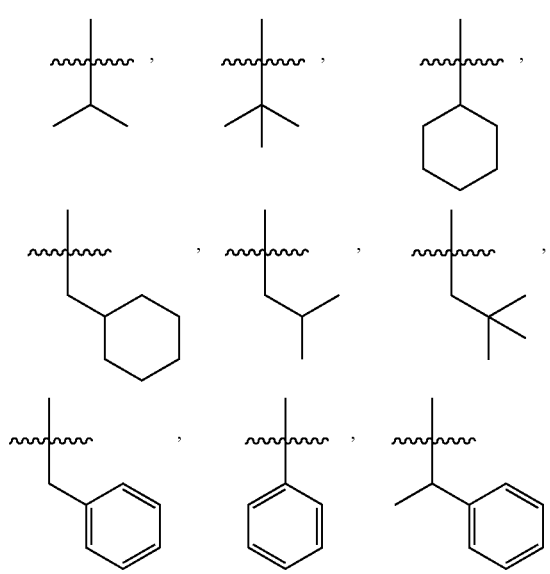

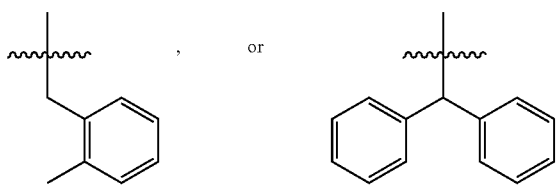

In other forms of any embodiment of this invention, T is selected from: (C6-C10)-aryl, (C6-C10)-aryl-(C1-C12)aliphatic, (C3-C10)-cycloalkyl or -cycloalkenyl, [(C3-C10)-cycloalkyl or -cycloalkenyl]-(C1-C12)-aliphatic, (C3-C10)-heterocyclyl, (C3-C10)-heterocyclyl-(C1-C12)-aliphatic, (C5-C10)heteroaryl, or (C5-C10)heteroaryl-(C1-C12)-aliphatic, wherein each T is optionally substituted with up to 3 J substituents.

In other forms of any embodiment of this invention, T is (C5-C10)heteroaryl, wherein T is optionally substituted with up to 3 J substituents.

In other forms of any embodiment of this invention, T is:

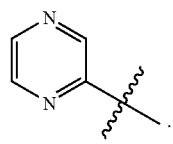

In other forms of any embodiment of this invention, T is:

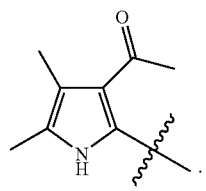

In other forms of any embodiment of this invention, T is:

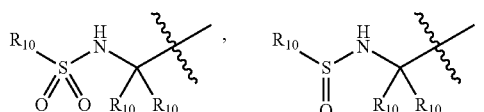

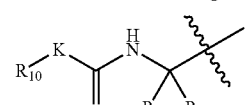

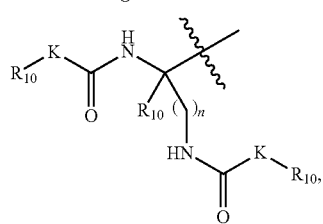

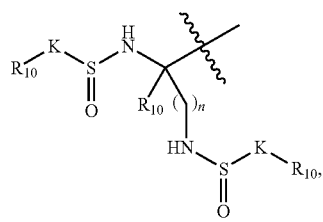

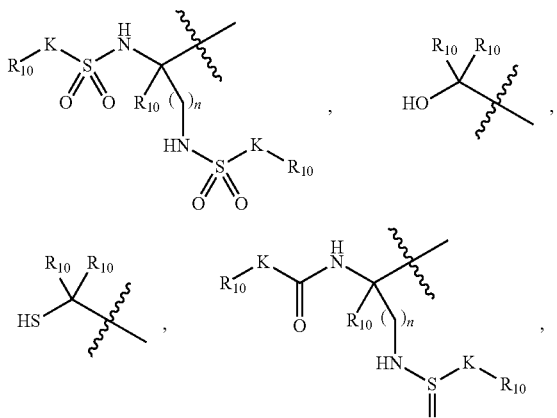

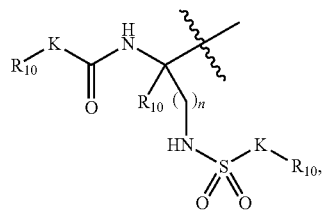

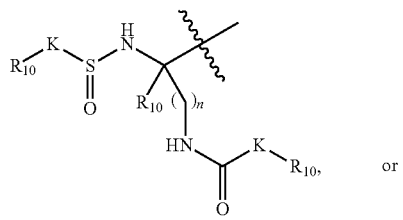

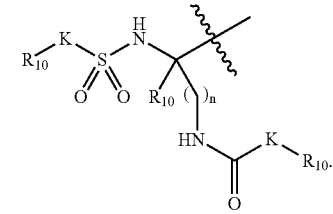

In other forms of any embodiment of this invention, T is:

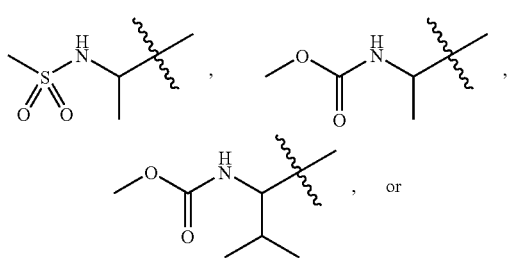

-continued
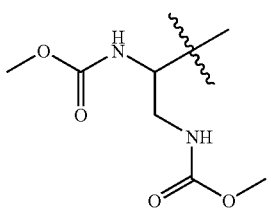
In other forms of any embodiment of this invention, T contains at least one hydrogen bond donor moiety selected from —NH$_2$, —NH—, —OH, and —SH.
In other forms of any embodiment of this invention, T is:
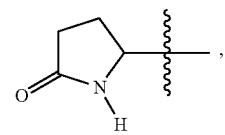 , 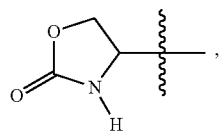 ,
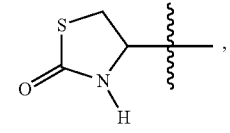 , 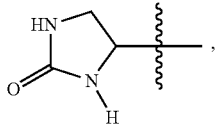 ,
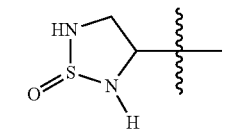 , 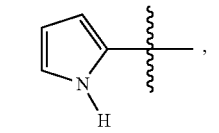 ,
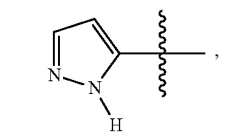 , 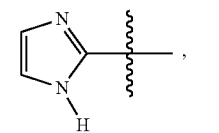 ,
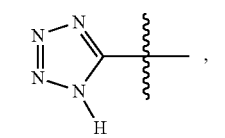 , 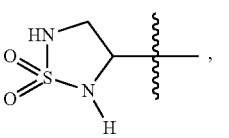 ,
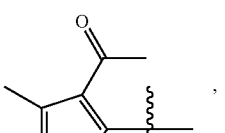 , 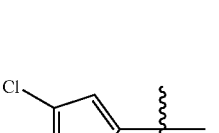 ,
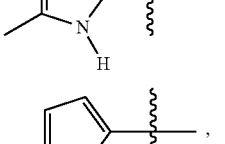 , 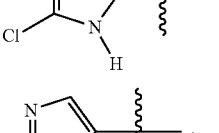 ,
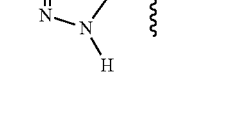 , 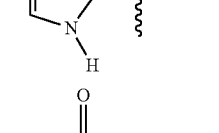 ,
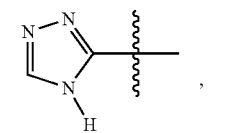 , 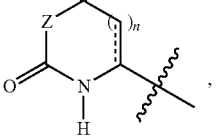 ,
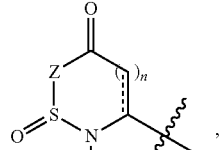 , 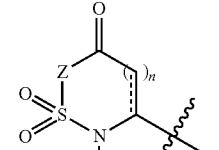 ,
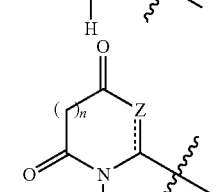 , 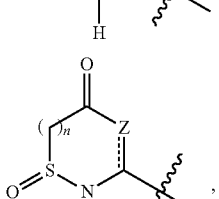 ,
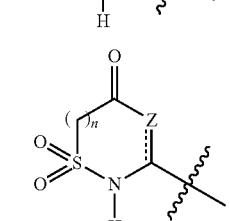 , 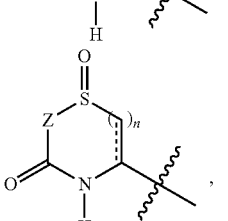 ,
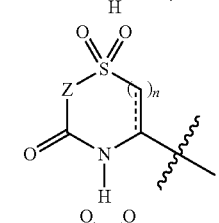 , 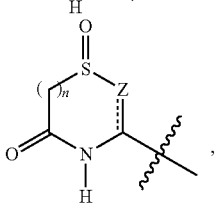 ,
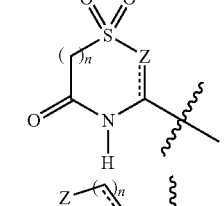 , 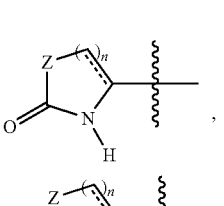 ,
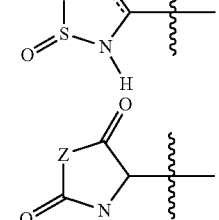 , 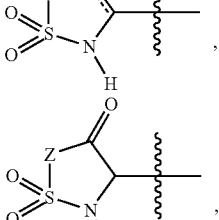 ,
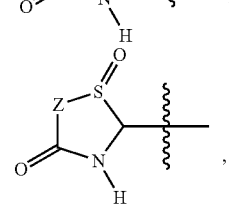 , 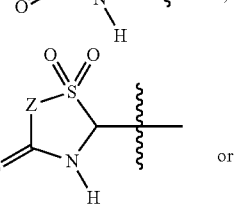 or
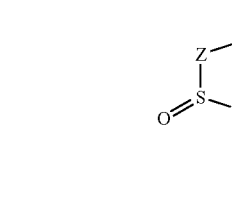 , 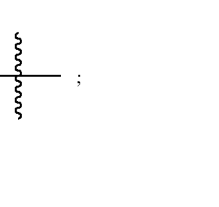 ;
wherein:
T is optionally substituted with up to 4 J substituents, wherein J is as defined herein;
Z is independently O, S, NR$_{10}$, C(R$_{10}$)$_2$;

n is independently 1 or 2; and
‒ ‒ ‒ ‒ ‒
is independently a single bond or a double bond.
In other forms of any embodiment of this invention, T is:
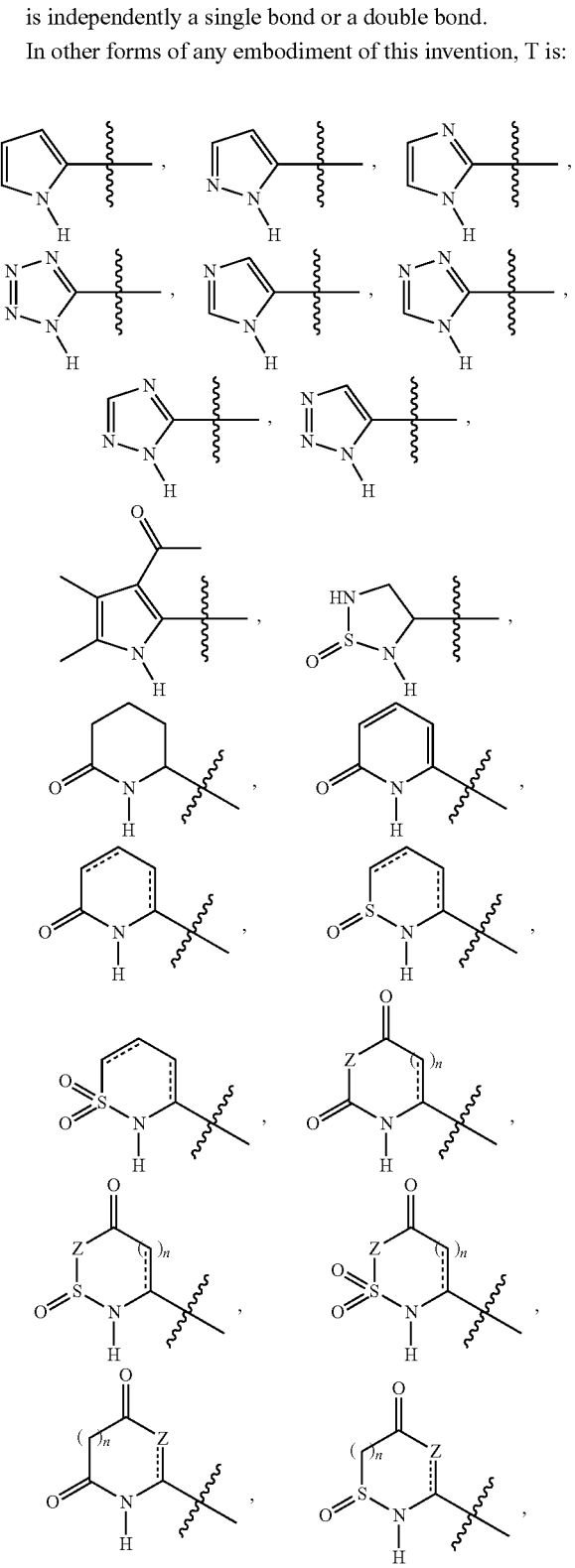
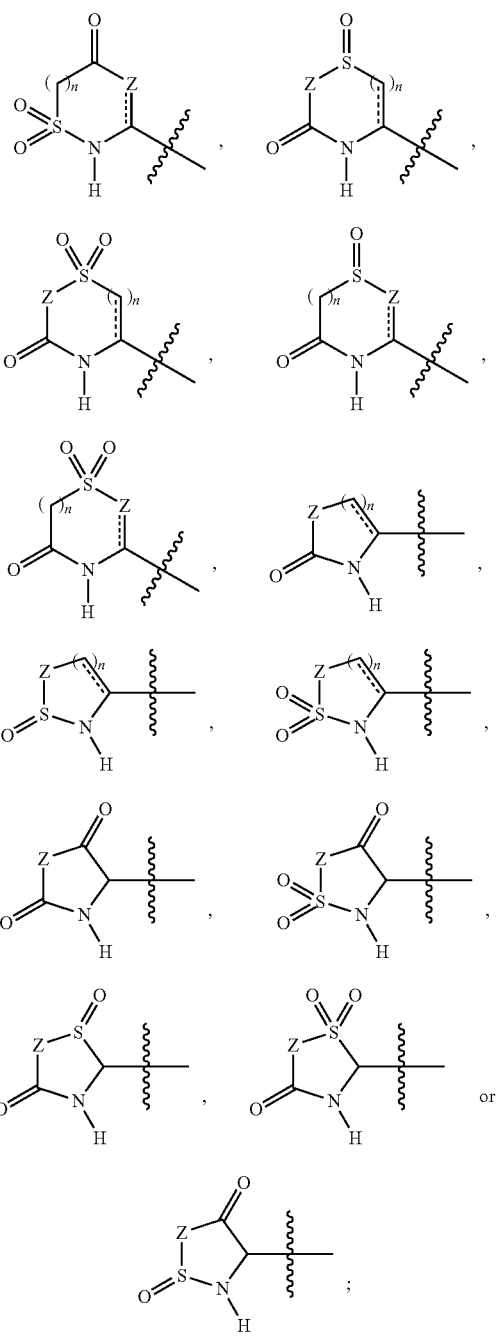
wherein:
T is optionally substituted with up to 4 J substituents, wherein J is as defined herein;
Z is independently O, S, $NR_{10}$, $C(R_{10})_2$, SO, $SO_2$;
n is independently 1 or 2; and
‒ ‒ ‒ ‒ ‒
is independently a single bond or a double bond.

In other forms of any embodiment of this invention, T is:

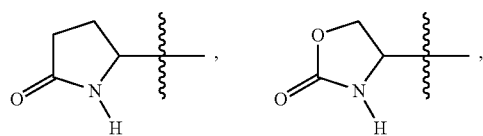

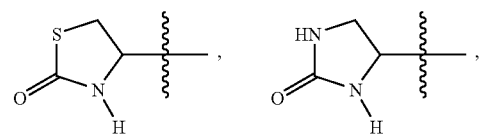

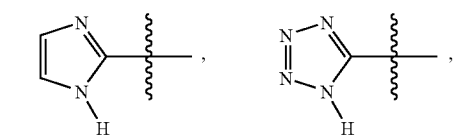

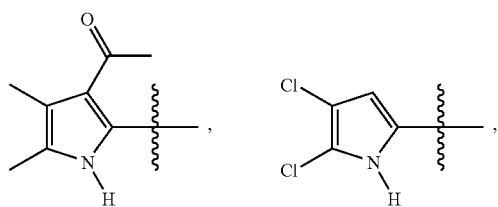

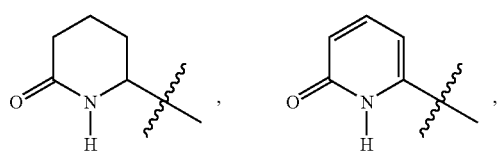

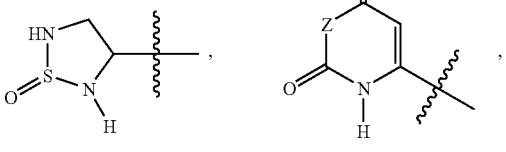

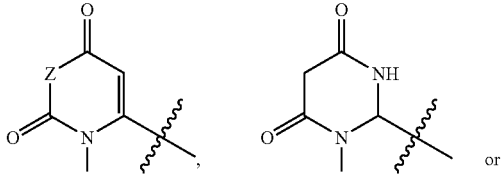

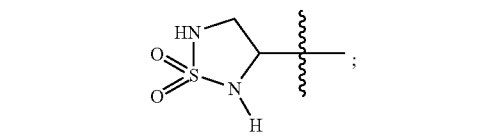

wherein:

T is optionally substituted with up to 4 J substituents, wherein J is as defined herein; and Z is independently O, S, $NR_{19}$, $C(R_{10})_2$, SO, $SO_2$.

In other forms of any embodiment of this invention, T is:

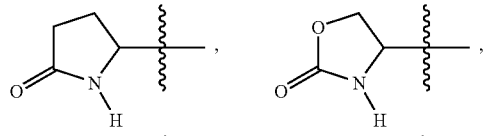

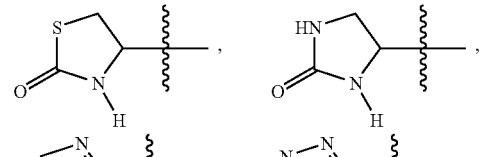

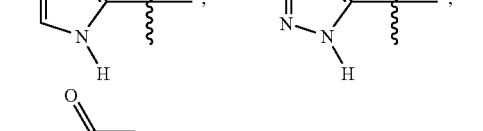

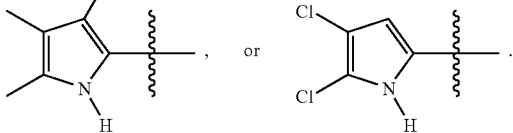

In other forms of any embodiment of this invention, V—R-T is selected from:

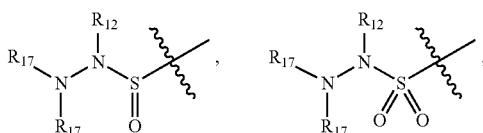

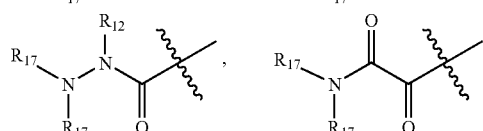

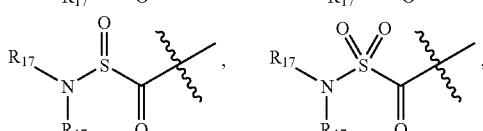

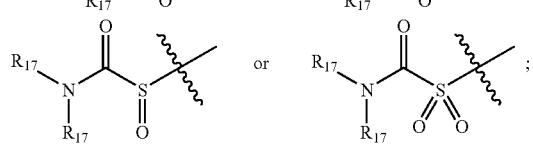

wherein $R_{12}$ and each $R_{17}$ are as defined herein.

In other forms of any embodiment of this invention, V—R-T is:

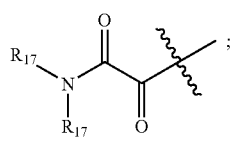

wherein:

one $R_{17}$ is hydrogen; and one $R_{17}$ is:

(C1-C12)-aliphatic-;
(C6-C10)-aryl-(C1-C12)aliphatic-, or
(C3-C10)-cycloalkyl or -cycloalkenyl-;

wherein up to 3 aliphatic carbon atoms in $R_{17}$ may be replaced by a heteroatom selected from O, N, NH, S, SO, or $SO_2$ in a chemically stable arrangement; and wherein $R_{17}$ is optionally substituted with up to 3 substituents independently selected from J.

In other forms of any embodiment of this invention, V—R-T is:

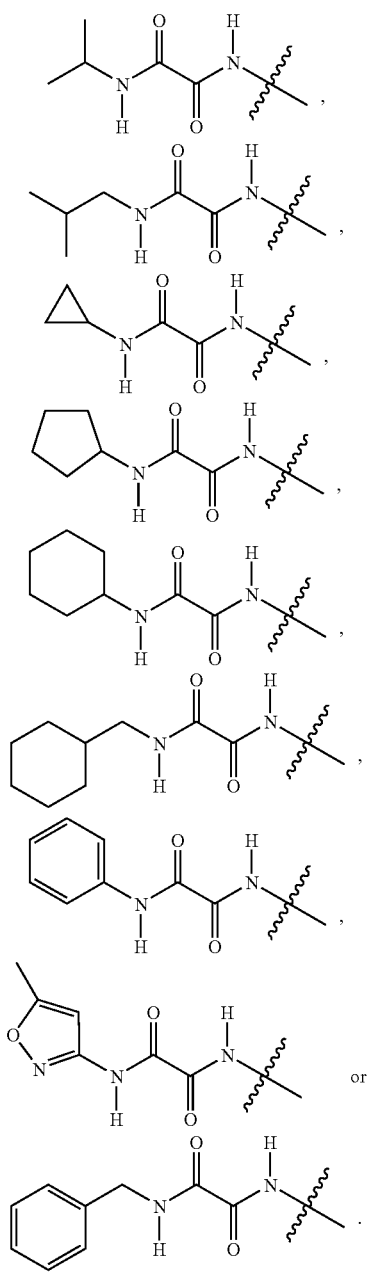

In other forms of any embodiment of this invention, $R_2$ and $R_4$ are each independently H or (C1-C3)-alkyl and $R_8$, if present, is H or (C1-C3)-alkyl.

In other forms of any embodiment of this invention, $R_2$ and $R_4$ are each H, and $R_8$, if present, is H.

In other forms of any embodiment of this invention, $R_8$, if present, is hydrogen, V is —C(O)—, R is a bond and T is as defined in any of the embodiments herein.

In other forms of any embodiment of this invention, W is:

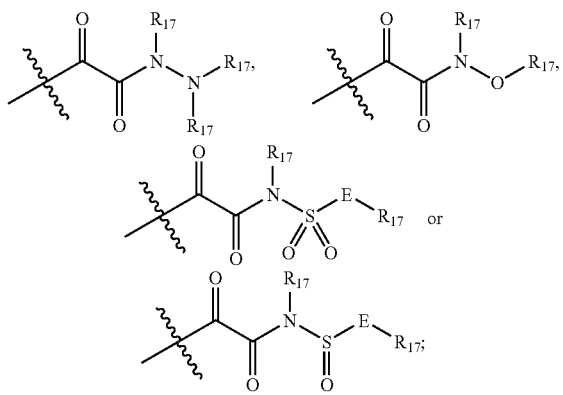

wherein:
E is selected from $N(R_{17})$ or a bond;
each $R_{17}$ is independently:
hydrogen-,
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-,
(C5-C10)heteroaryl-(C1-C12)-aliphatic-, or
two $R_{17}$ groups together with the nitrogen to which they are bound form a 3- to a 20-membered mono-, an 8- to 20-membered bi- or tri-cyclic heterocyclic ring system;

wherein, in the bi- and tri-cyclic ring system, each ring is linearly fused, bridged, or spirocyclic;
wherein each ring is either aromatic or nonaromatic;
wherein each heteroatom in the heterocyclic ring system is selected from the group consisting of N, NH, O, S, SO, and $SO_2$;
wherein each ring is optionally fused to a (C6-C10)aryl, (C5-C10)heteroaryl, (C3-C10)cycloalkyl, or (C3-C10)heterocyclyl; and
wherein said ring has up to 3 substituents selected independently from J.

In other forms of any embodiment of this invention, W is:

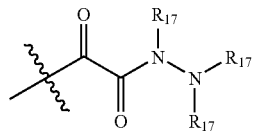

wherein
each $R_{17}$ is independently:
hydrogen-,
(C1-C12)-aliphatic-,
(C3-C10)-cycloalkyl- or cycloalkenyl-,

[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-,
(C5-C10)heteroaryl-(C1-C12)-aliphatic-, or
two $R_{17}$ groups together with the nitrogen to which they are bound form a 3- to a 20-membered mono-, an 8- to 20-membered bi- or tri-cyclic heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10)heterocyclyl; and wherein said ring has up to 3 substituents selected independently from J.

In other forms of any embodiment of this invention, W is:

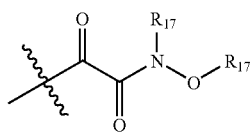

wherein
each $R_{17}$ is independently:
hydrogen-,
(C1-C12)-aliphatic-,
(C3-C10)-cycloalkyl- or cycloalkenyl-,
[(C3-C10)-cycloalkyl- or cycloalkenyl]-(C1-C12)-aliphatic-,
(C6-C10)-aryl-,
(C6-C10)-aryl-(C1-C12)aliphatic-,
(C3-C10)-heterocyclyl-,
(C3-C10)-heterocyclyl-(C1-C12)-aliphatic-,
(C5-C10)heteroaryl-,
(C5-C10)heteroaryl-(C1-C12)-aliphatic-, or
two $R_{17}$ groups together with the nitrogen to which they are bound form a 3- to a 20-membered mono-, an 8- to 20-membered bi- or tri-cyclic heterocyclic ring system;

wherein, in the bi- and tri-cyclic ring system, each ring is linearly fused, bridged, or spirocyclic;

wherein each ring is either aromatic or nonaromatic;

wherein each heteroatom in the heterocyclic ring system is selected from the group consisting of N, NH, O, S, SO, and $SO_2$;

wherein each ring is optionally fused to a (C6-C10)aryl, (C5-C10)heteroaryl, (C3-C10)cycloalkyl, or (C3-C10)heterocyclyl; and wherein said ring has up to 3 substituents selected independently from J.

In other forms of any embodiment of this invention, J is halogen —OR', —$NO_2$, —$CF_3$, —$OCF_3$, —R', oxo, 1,2-methylenedioxy, —N(R')$_2$, —SR', —SOR', —$SO_2$R', —C(O)R', —COOR'—CON(R')$_2$, —N(R')COR', —N(COR')COR', —CN, or —$SO_2$N(R')$_2$.

In other forms of any embodiment of this invention, $J_2$ is halogen, —OR', —$NO_2$, —$CF_3$, —$OCF_3$, —R', oxo, 1,2-methylenedioxy, —N(R')$_2$, —SR', 'SOR', —$SO_2$R', —C(O)R', —COOR'—CON(R')$_2$, —N(R')COR', —N(COR')COR', —CN, or —$SO_2$N(R')$_2$.

In other forms of any embodiment of this invention, in J and $J_2$ the halogen is chloro or fluoro. In other forms of any embodiment of this invention, the halogen is fluoro.

In other forms of any embodiment of this invention, $R_{1'}$, if present, is H.

In other forms of any embodiment of this invention, $R_{13'}$ is H.

In other forms of any embodiment of this invention, $R_{11'}$ is H.

In other forms of any embodiment of this invention, $R_{12}$ is H.

In other forms of any embodiment of this invention, a process for preparing a compound of this invention is provided. These processes are described in the schemes and examples.

In other forms of any embodiment of this invention, the compound is:

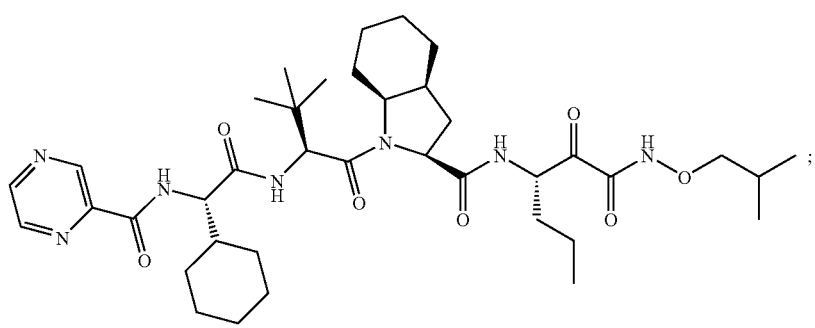

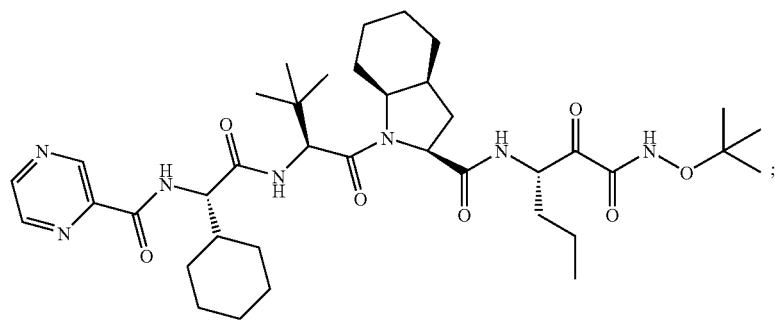
2
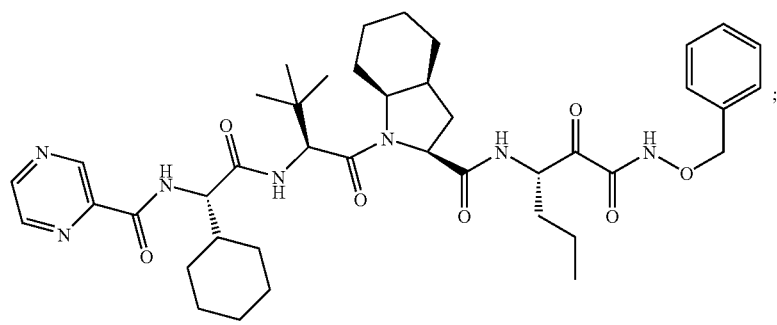
3
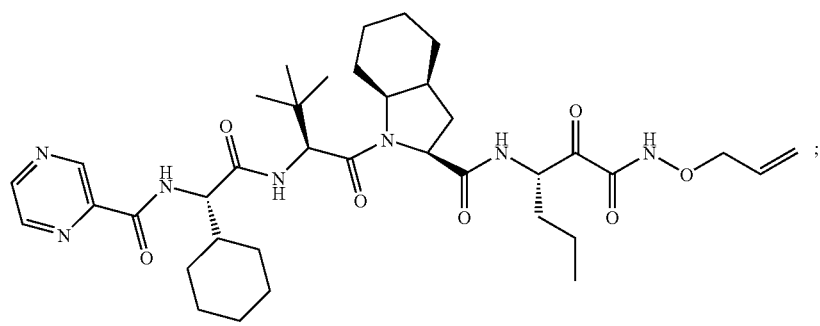
4
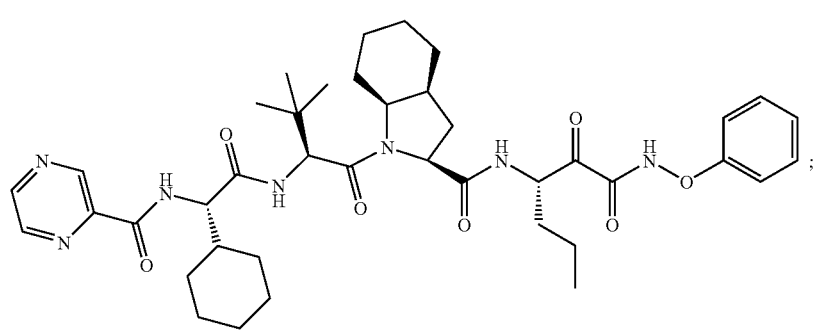
5
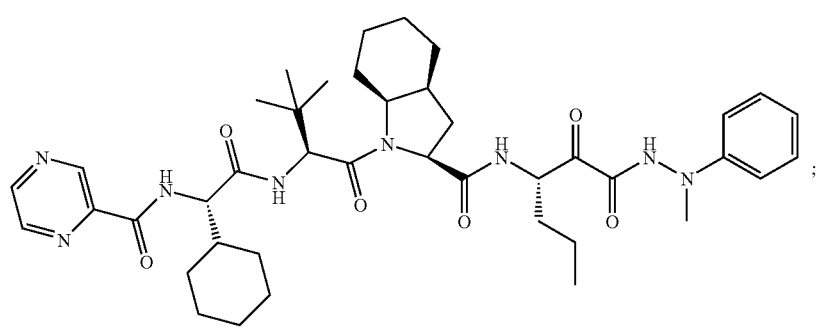
6

-continued

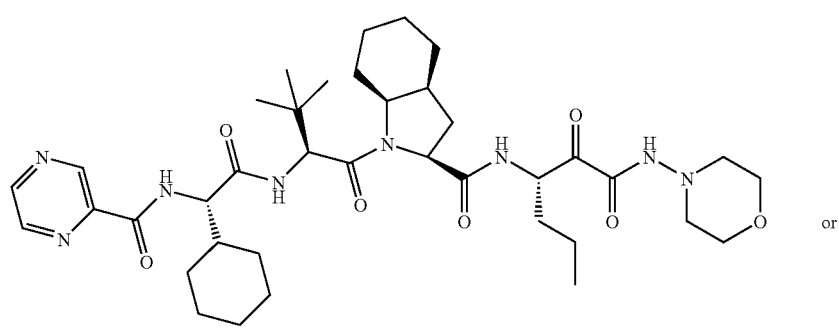

or

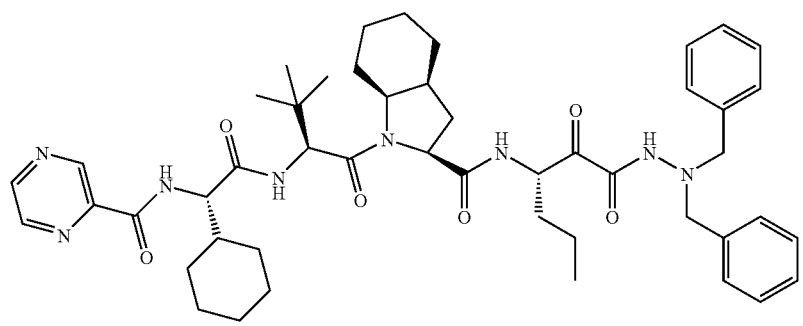

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration.

In another embodiment, the compounds of this invention have the structures and stereochemistry depicted in compounds 1-8.

It is understood that any of the embodiments recited above, including those embodiments in the above species, may be combined to produce another embodiment of this invention.

Abbreviations which are used in the schemes, preparations and the examples that follow are:
THF: tetrahydrofuran
DMF: N,N,-dimethylformamide
DMA: dimethylacetamide
EtOAc: ethyl acetate
AcOH: acetic acid
NMM: N-methylmorpholine
NMP: N-methylpyyrolidinone
EtOH: ethanol
t-BuOH: tert-butanol
Et$_2$O: diethyl ether
DMSO: dimethyl sulfoxide
DCCA: dichloroacetic acid
DIEA: diisopropylethylamine
MeCN: acetonitrile
TFA: trifluoroacetic acid
DBU: 1,8-diazabicyclo[5.4.0]undec-7-ene
DEAD: diethyl azodicarboxylate
HOBt: 1-hydroxybenzotriazole hydrate
HOAt: 1-hydroxy-7-azabenzotriazole
EDC: 1-(3-dimethylaminopropyl)-3-ethylcarbodiimide hydrochloride
Boc: tert-butyloxycarbonyl
Boc$_2$O: di-tert-butyldicarbonate
Cbz: benzyloxycarbonyl
Cbz-Cl: benzyl chloroformate
Fmoc: 9-fluorenyl methyloxycarbonyl
Chg: cyclohexylglycine
t-BG: tert-butylglycine
mCBPA: 3-chloroperoxybenzoic acid
IBX: o-iodoxybenzoic acid
DAST: (diethylamino)sulfur trifluoride
TEMPO: 2,2,6,6-tetramethyl-1-piperidinyloxy, free radical
PyBROP: tris(pyrrolidino)bromophosphonium hexafluorophosphate
TBTU or HATU: 2-(1H-benzotriazole-1-yl)-1,1,3,3-tetramethyluronium tetrafluoroborate
DMAP: 4-dimethylaminopyridine
AIBN: 2,2'-azobisisobutyronitrile
DMEM: Dulbecco's minimal essential media
PBS: phosphate-buffered saline
rt or RT: room temperature
ON: overnight
ND: not determined
MS: mass spectrometry
LC: liquid chromatography
Xaa: an amino acid either commercially available or synthetically prepared from commercially available intermediates and reagents.

General Synthetic Methodology:

The compounds of this invention may be prepared in general by methods known to those skilled in the art. Schemes 1-22 and schemes 19a-20a below illustrate synthetic routes to the compounds of the present invention. Other equivalent schemes, which will be readily apparent to the ordinary skilled organic chemist, may alternatively be used to synthesize various portions of the molecule as illustrated by the general scheme below, and the preparative examples that follow.

Scheme 1:

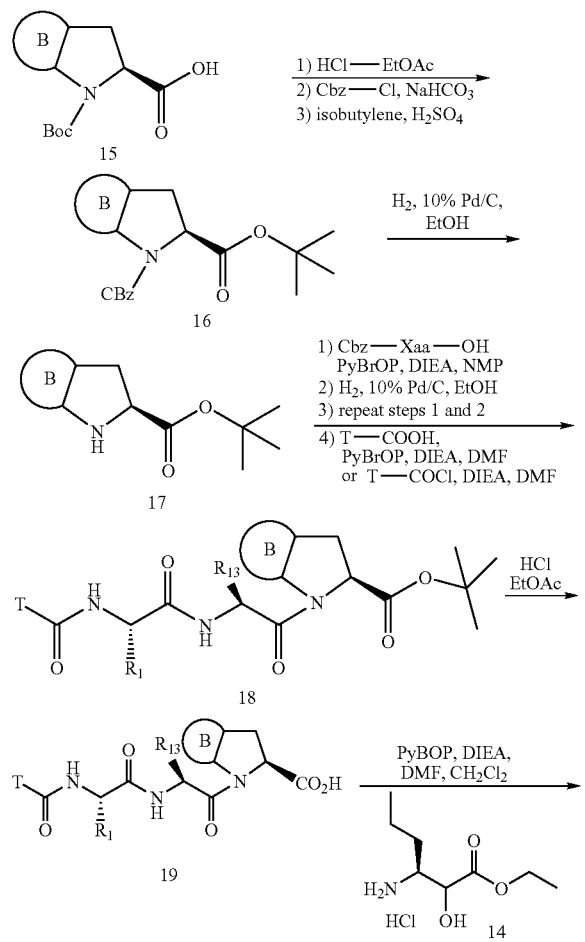

Scheme 1 above provides a synthetic route for the preparation of intermediate ester hydrochloride 14 from intermediate acid 9. Intermediate acid 9 was prepared according to the procedure described by Harbeson, S. et al., *J. Med. Chem.*, Vol. 37, No. 18, pp. 2918-2929 (1994).

Scheme 2:

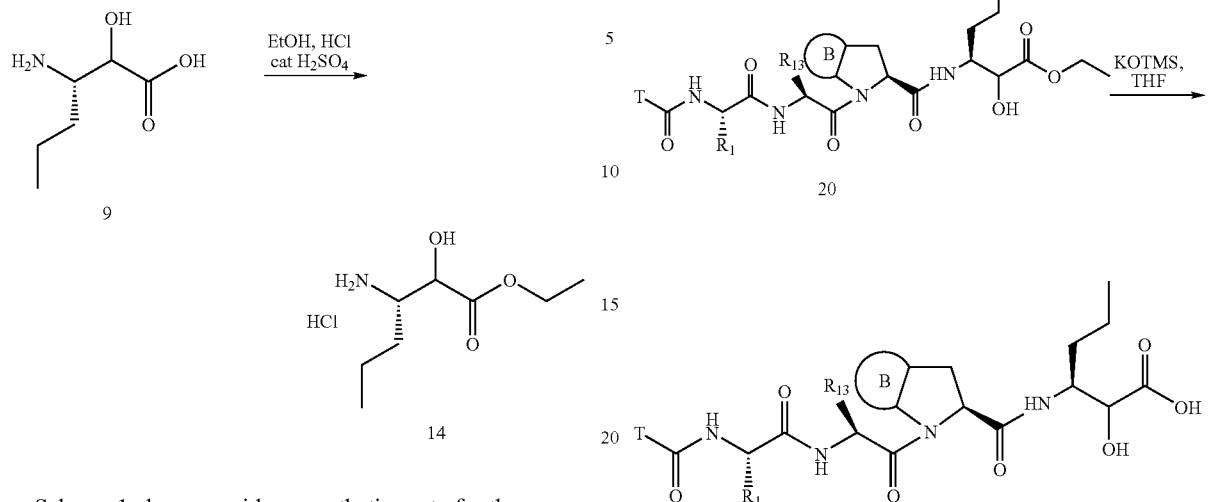

Scheme 2 above provides a synthetic route for the preparation of intermediate 21 (wherein V is —C(O)—, R is a bond, the —N($R_{12}$)CH($R_{11}$)C(O)— radical is a bicyclic proline derivative, and T, $R_1$, $R_{13}$, and ring B are as defined in any of the embodiments herein) from either commercially available amino esters, amino esters prepared according to any of the schemes herein, or amino esters prepared according to any of the issued patents or published patent applications incorporated herein by reference. It will also be appreciated by one of skill in the art that compounds of formula I, wherein z is zero, may be prepared according to scheme 1 wherein one less CBz-Xaa-OH group is coupled during preparation of the compound.

Scheme 3: Synthesis of Compounds of Formula I wherein W is C(O)C(O)NHN($R_{17}$)$_2$:

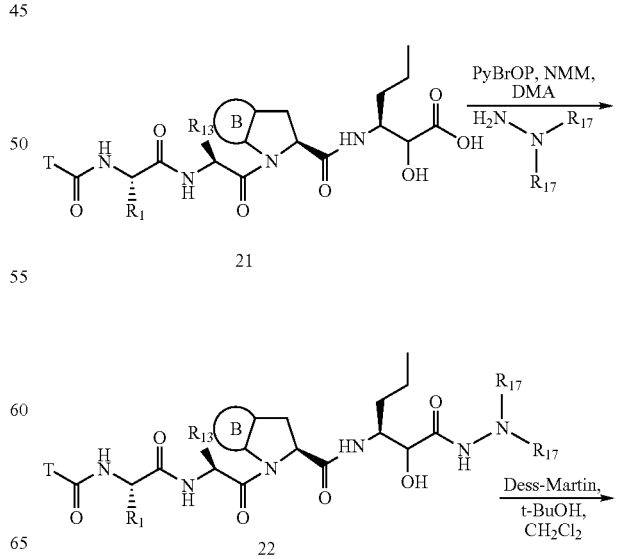

-continued

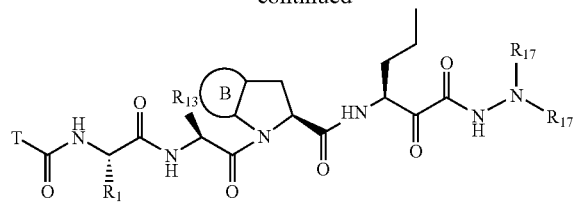

23

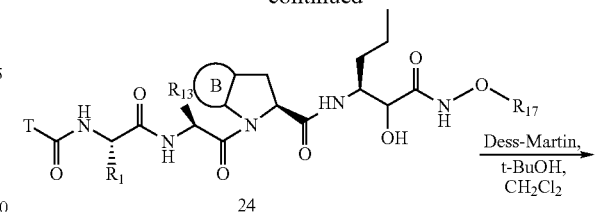

24

Schemes 1 and 2 in combination with scheme 3 above provide a general route for the preparation of compounds of formula I, wherein V is —C(O)—, R is a bond, the —N($R_{12}$)CH($R_{11}$)C(O)— radical is a bicyclic proline derivative, W is C(O C(O)NHN($R_{17}$)$_2$ and T, $R_1$, $R_{13}$, $R_{17}$, and ring B are as defined in any of the embodiments herein. Coupling procedures for converting intermediate 21 to amide 22 followed by oxidation with Dess Martin periodinane to final product 23 was accomplished according to the procedures detailed in the examples described herein. The preparation of other compounds of formula I wherein W is C(O)C(O)NHN($R_{17}$)$_2$ and P2 is other than a bicyclic proline may also accomplished by the general route provided in schemes 1 and 2 starting from the appropriately protected P2 amino ester. It will also be appreciated by one of skill in the art that compounds of formula I, wherein z is zero, may be prepared according to schemes 1 and 2 wherein one less CBz-Xaa-OH group is coupled during preparation of the compound.

Scheme 4: Synthesis of Compounds of Formula I wherein W is C(O)C(O)NHOR$_{17}$:

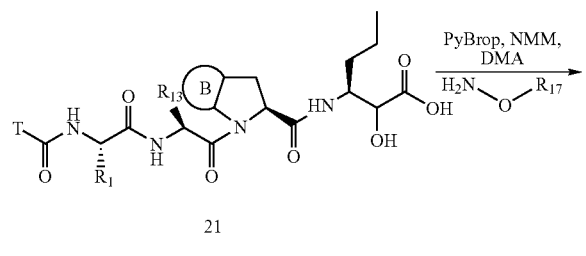

21

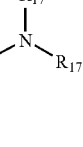

25

Schemes 1 and 2 in combination with scheme 4 above provide a general route for the preparation of compounds of formula I, from intermediate acid 21 and commercially available $R_{17}$ hydroxyl amine, wherein V is —C(O)—, R is a bond, the —N($R_{12}$)CH($R_{11}$)C(O)— radical is a bicyclic proline derivative, W is C(O)C(O)NHOR$_{17}$, and T, $R_1$, $R_{13}$, $R_{17}$, and ring B are as defined in any of the embodiments herein. Coupling procedures for converting intermediate 21 to amide 24 followed by oxidation with Dess Martin periodinane to final product 25 was accomplished according to the procedures detailed in the examples described herein. The preparation of other compounds of formula I wherein P2 is other than a bicyclic proline and W is C(O)C(O)NHOR$_{17}$ may also accomplished by the general routes provided in schemes 1, 2, and 4 starting from the appropriately protected P2 amino ester. It will also be appreciated by one of skill in the art that compounds of formula I, wherein z is zero, may be prepared according to schemes 1, 2, and 4 wherein one less CBz-Xaa-OH group is coupled during preparation of the compound.

Scheme 5: Synthesis of Compounds of Formula I wherein W is C(O)C(O)NHSO$_2$N($R_{17}$)$_2$:

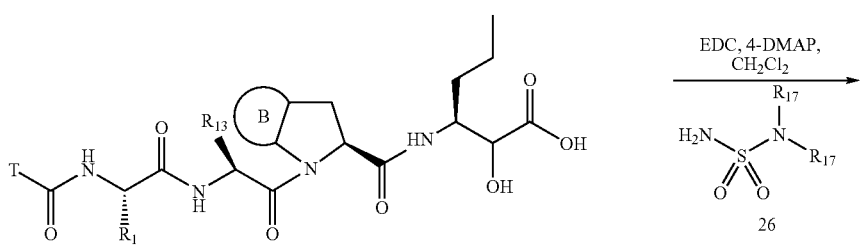

21            26

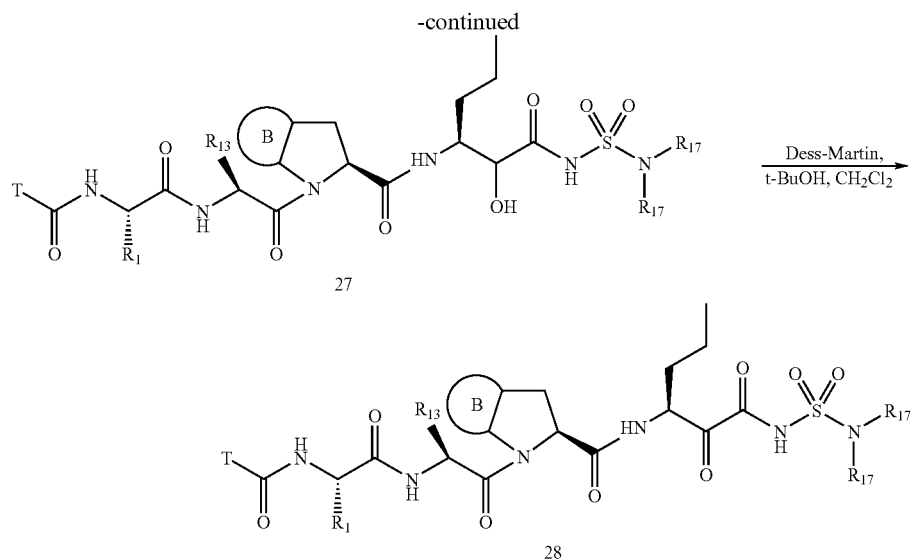

Scheme 5 above provides a general route for the preparation of compounds of formula I, from intermediate acid 21 and commercially available $R_{17}$ amino sulfonamide 26, wherein V is —C(O)—, R is a bond, the —N($R_{12}$)CH($R_{11}$)C(O)— radical is a bicyclic proline derivative, W is C(O)C(O)NHSO$_2$N($R_{17}$)$_2$ and T, $R_1$, $R_3$, $R_{17}$, and ring B are as defined in any of the embodiments herein. The coupling of intermediate 21 and amino sulfonamide 26 to prepare ketoamide 27 is accomplished according to the procedures of Rossiter, S. et al., *Biorg. Med. Chem. Lett.*, 12, p.2523 (2002) and Pelletier, J. et al. *Synlett*, 11, p. 1141 (1995). Final oxidation of intermediate 27 to compounds of formula I (as shown by compound 28) is accomplished by using Dess Martin periodinane as oxidant according to known procedures. The preparation of other compounds of formula I wherein W is C(O)C(O)NHSO$_2$N($R_{17}$)$_2$ and P2 is other than a bicyclic proline may also accomplished by the general routes provided in schemes 1, 2, and 5 starting from the appropriately protected P2 amino ester. It will also be appreciated by one of skill in the art that compounds of formula I, wherein z is zero, may be prepared according to schemes 1, 2, and 5 wherein one less CBz-Xaa-OH group is coupled during preparation of the compound.

Scheme 6: Synthesis of Compounds of Formula I wherein W is C(O)C(O)NHSO$_2$R$_{17}$:

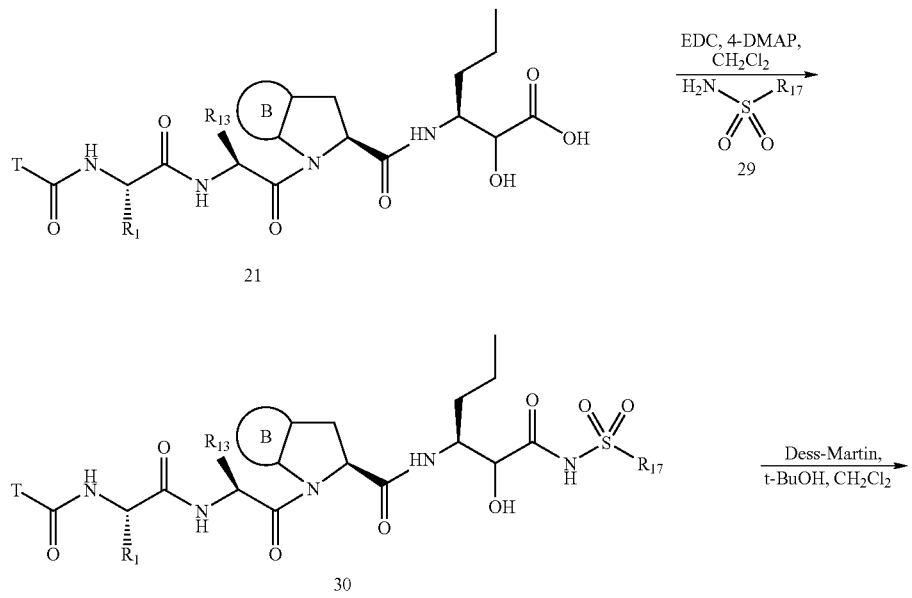

-continued

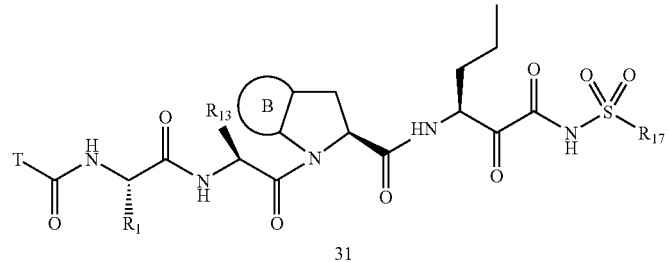

31

Scheme 6 above provides a general route for the preparation of compounds of formula I from intermediate acid 21 and commercially available $R_{17}$ sulfonamide 29, wherein V is —C(O)—, R is a bond, the —N($R_{12}$)CH($R_{11}$)C(O)— radical is a bicyclic proline derivative, W is C(O)C(O)NHSO$_2$R$_{17}$ and T, $R_1$, $R_3$, $R_{17}$, and ring B are as defined in any of the embodiments herein. The coupling of intermediate 21 and sulfonamide 29 to prepare ketoamide 30 is accomplished according to the procedures of Rossiter, S. et al., *Biorg. Med. Chem. Lett.*, 12, p.2523 (2002) and Pelletier, J. et al. *Synlett*, 11, p. 1141 (1995). Oxidation of keto alcohol 30 to give diketo amide 31 is accomplished using Dess Martin periodinane according to procedures known in the art. The preparation of other compounds of formula I wherein W is C(O)C(O)NHSO$_2$R$_{17}$ and P2 is other than a bicyclic proline may also accomplished by the general routes provided in schemes 1, 2, and 6 starting from the appropriately protected P2 amino ester. It will also be appreciated by one of skill in the art that compounds of formula I, wherein z is zero, may be prepared according to schemes 1, 2, and 6 wherein one less CBz-Xaa-OH group is coupled during preparation of the compound.

Scheme 7: Synthesis of Compounds of Formula I wherein W is C(O)C(O)NHS(O)N(R$_{17}$)$_2$:

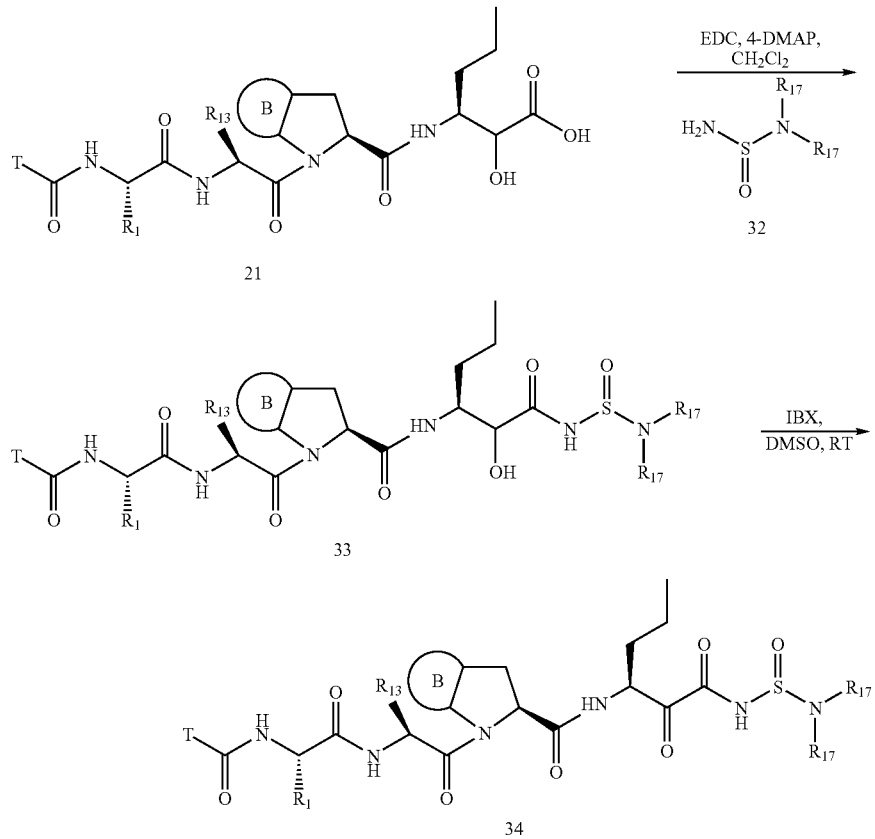

Scheme 7 above provides a general route for the preparation of compounds of formula I, from intermediate acid 21 and amino sulfinamide 32 (either commercially available or prepared according to the procedure of Schipper, E. et al., *J. Org. Chem.*, 34, p.2397 (1969)), wherein W is C(O)C(O)NHS(O)N($R_{17}$)$_2$ and wherein T, $R_1$, $R_3$, $R_{17}$, and ring B are as defined in any of the embodiments herein. Oxidation of intermediate alcohol 33 to final product 34 is accomplished with IBX (o-iodoxybenzoic acid) as oxidant according to the procedure of Wu, Y. et al., *Organic Letters*, 4, p. 2141 (2002). The preparation of other compounds of formula I wherein W is C(O)C(O)NHS(O)N($R_{17}$)$_2$ and P2 is other than a bicyclic proline may also accomplished by the general routes provided in schemes 1, 2, and 7 starting from the appropriately protected P2 amino ester. It will also be appreciated by one of skill in the art that compounds of formula I, wherein z is zero, may be prepared according to schemes 1, 2, and 7 wherein one less CBz-Xaa-OH group is coupled during preparation of the compound.

Scheme 8 above provides a general route for the preparation of compounds of formula I, from intermediate acid 21 and amino sulfinamide 35 (either commercially available or prepared according to the procedure of Schipper, E. et al., *J. Org. Chem.*, 34, p.2397 (1969)), wherein W is C(O)C(O)NHS(O)$R_{17}$ and wherein T, $R_1$, $R_3$, $R_{17}$, and ring B are as defined in any of the embodiments herein. Oxidation of intermediate alcohol 36 to final product 37 is accomplished with IBX (o-iodoxybenzoic acid) as oxidant according to the procedure of Wu, Y. et al., *Organic Letters*, 4, p. 2141 (2002). The preparation of other compounds of formula I wherein W is C(O)C(O)NHS(O)$R_{17}$ and P2 is other than a bicyclic proline may also accomplished by the general routes provided in schemes 1, 2, and 8 starting from the appropriately protected P2 amino ester. It will also be appreciated by one of skill in the art that compounds of formula I, wherein z is zero, may be prepared according to schemes 1, 2, and 8 wherein one less CBz-Xaa-OH group is coupled during preparation of the compound.

Scheme 8: Synthesis of Compounds of Formula I wherein W is C(O)C(O)NHS(O)$R_{17}$:

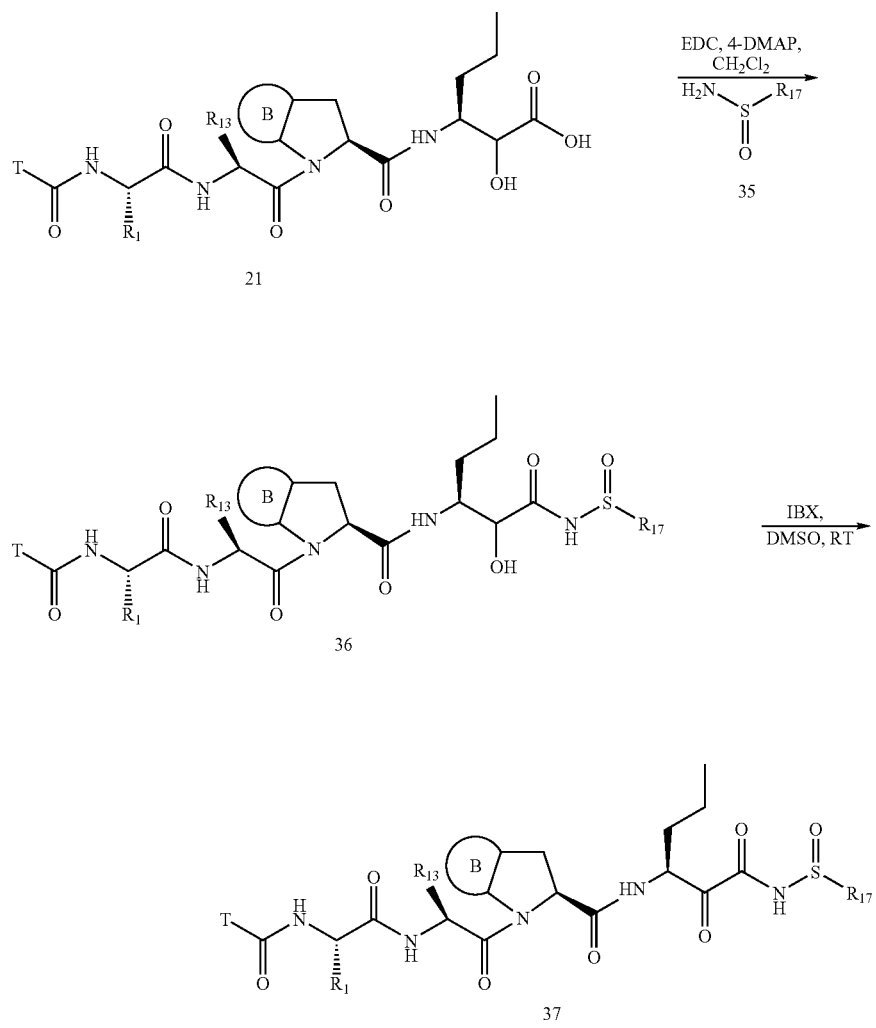

Scheme 9:

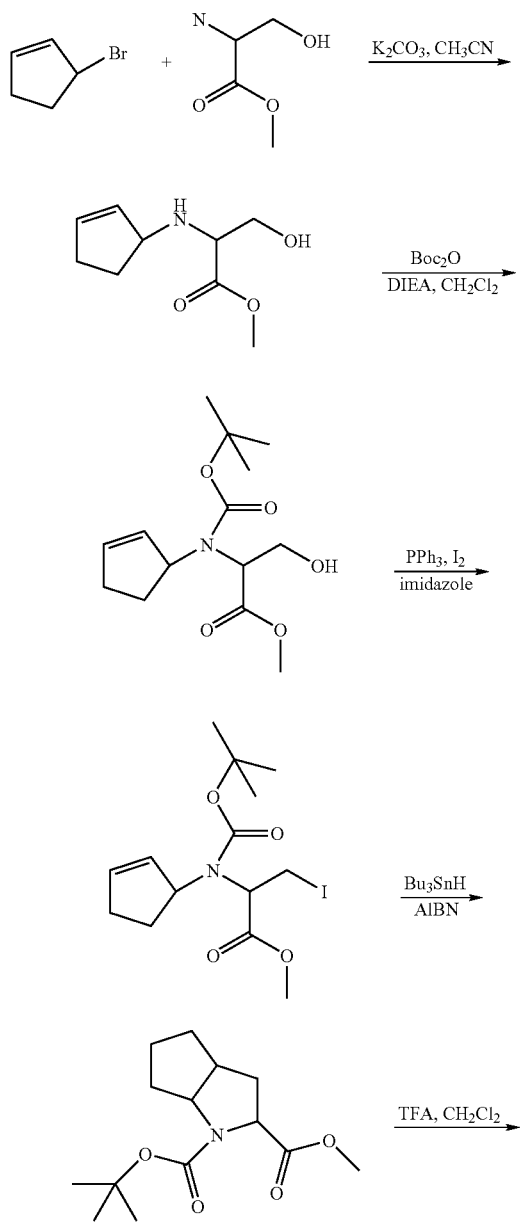

Schemes 1-8 in combination with scheme 9 above provide another general method for the preparation of compounds of formula I wherein the —N(R$_{12}$)CH(R$_{11}$)C(O)— radical is as shown above. It will also be appreciated by one of skill in the art that compounds of formula I, wherein z is zero, may be prepared according to schemes 1-9 wherein one less CBz-Xaa-OH group is coupled during preparation of the compound.

Scheme 10:

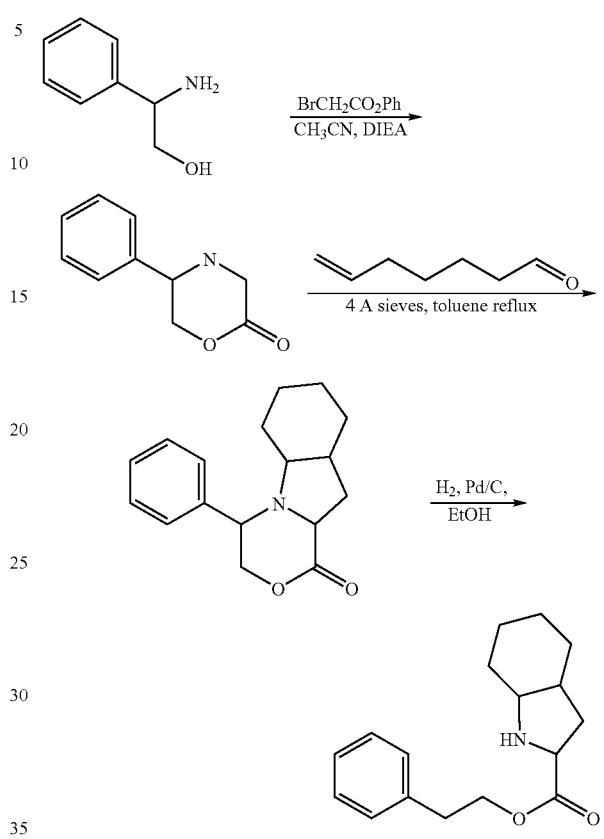

Schemes 1-8 in combination with scheme 10 above provide another general method for the preparation of compounds of formula I wherein the —N(R$_{12}$)CH(R$_{11}$)C(O)— radical is as shown above. It will also be appreciated by one of skill in the art that compounds of formula I, wherein z is zero, may be prepared according to schemes 1-8 and 10 wherein one less CBz-Xaa-OH group is coupled during preparation of the compound.

Scheme 11:

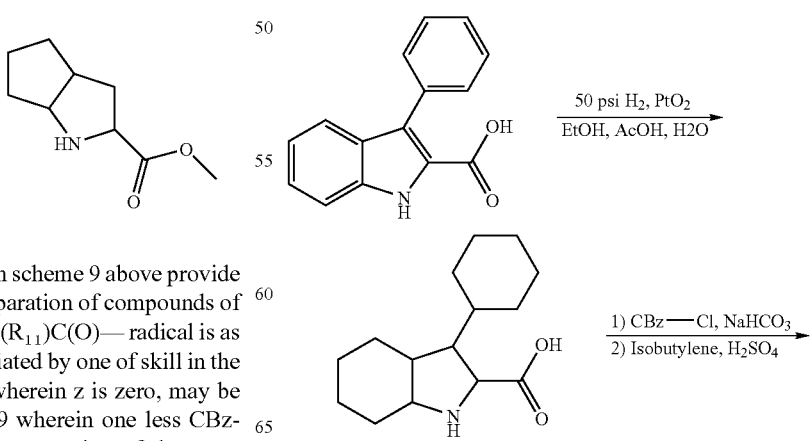

-continued

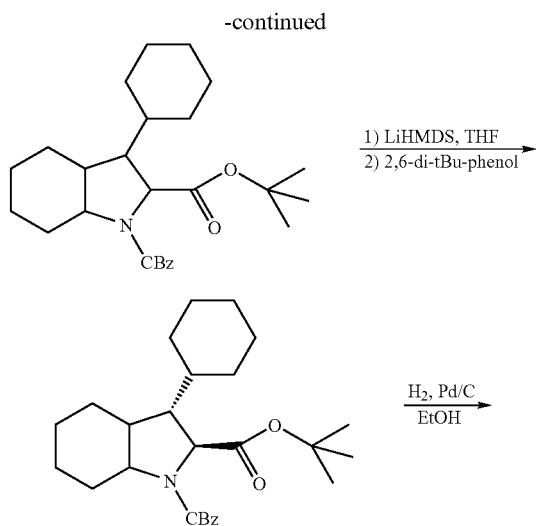

1) LiHMDS, THF
2) 2,6-di-tBu-phenol

H₂, Pd/C
EtOH

Schemes 1-8 in combination with scheme 11 above provide another general method for the preparation of compounds of formula I wherein the —N(R₁₂)CH(R₁₁)C(O)— radical is as shown above. It will also be appreciated by one of skill in the art that compounds of formula I, wherein z is zero, may be prepared according to schemes 1-8 and 11 wherein one less CBz-Xaa-OH group is coupled during preparation of the compound.

Scheme 12:

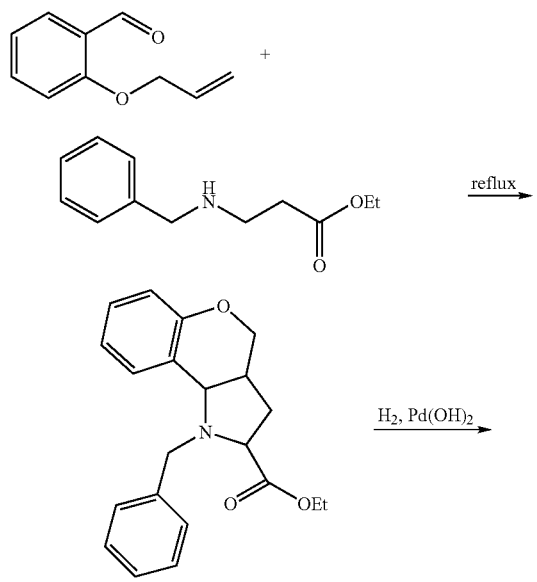

reflux

H₂, Pd(OH)₂

-continued

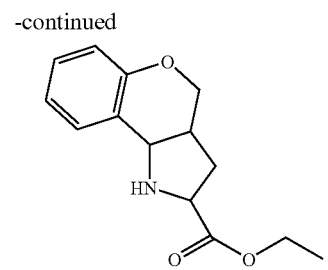

Schemes 1-8 in combination with scheme 12 above provide another general method for the preparation of compounds of formula I wherein the —N(R₁₂)CH(R₁₁)C(O)— radical is as shown above. It will also be appreciated by one of skill in the art that compounds of formula I, wherein z is zero, may be prepared according to schemes 1-8 and 12 wherein one less CBz-Xaa-OH group is coupled during preparation of the compound.

Scheme 13:

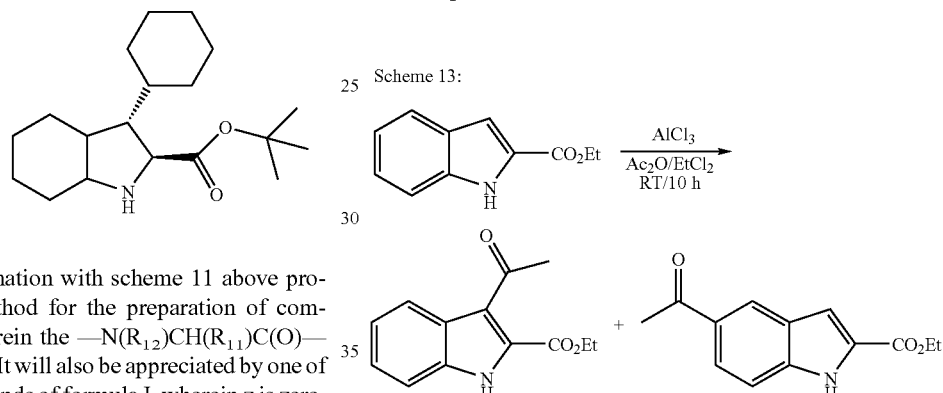

AlCl₃
Ac₂O/EtCl₂
RT/10 h

Schemes 1-8 in combination with scheme 13 above provide another general method for the preparation of compounds of formula I wherein the —N(R₁₂)CH(R₁₁)C(O)— radicals are as shown above. It will also be appreciated by one of skill in the art that compounds of formula I, wherein z is zero, may be prepared according to schemes 1-8 and 13 wherein one less CBz-Xaa-OH group is coupled during preparation of the compound.

Scheme 14:

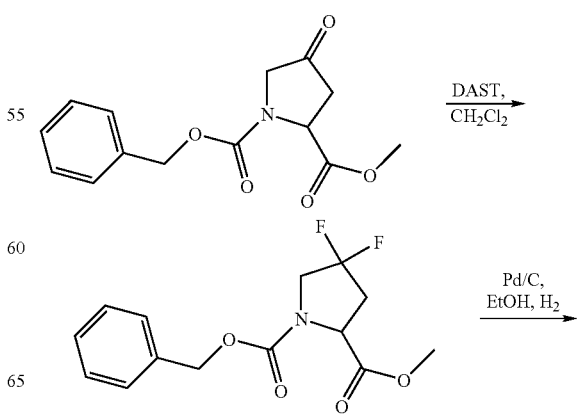

DAST,
CH₂Cl₂

Pd/C,
EtOH, H₂

-continued

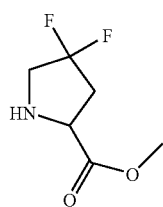

Starting with commercially available CBz 4-keto proline methyl ester and utilizing schemes 1-8 in combination with scheme 14 above provides a general method for the preparation of compounds of formula I wherein the —N($R_{12}$)CH($R_{11}$)C(O)— radical is as shown above. It will also be appreciated by one of skill in the art that compounds of formula I, wherein z is zero, may be prepared according to schemes 1-8 and 14 wherein one less CBz-Xaa-OH group is coupled during preparation of the compound.

Scheme 15:

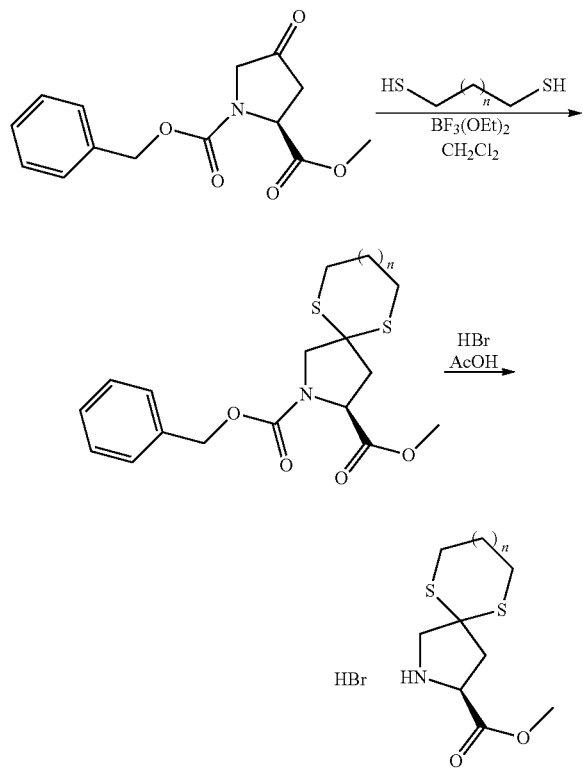

Starting with commercially available CBz 4-keto proline methyl ester and utilizing schemes 1-8 in combination with scheme 15 above provides a general method for the preparation of compounds of formula I wherein the —N($R_{12}$)CH($R_{11}$)C(O)— radical is as shown above and wherein n is 0 or 1. It will also be appreciated by one of skill in the art that compounds of formula I, wherein z is zero, may be prepared according to schemes 1-8 and 15 wherein one less CBz-Xaa-OH group is coupled during preparation of the compound.

Scheme 16:

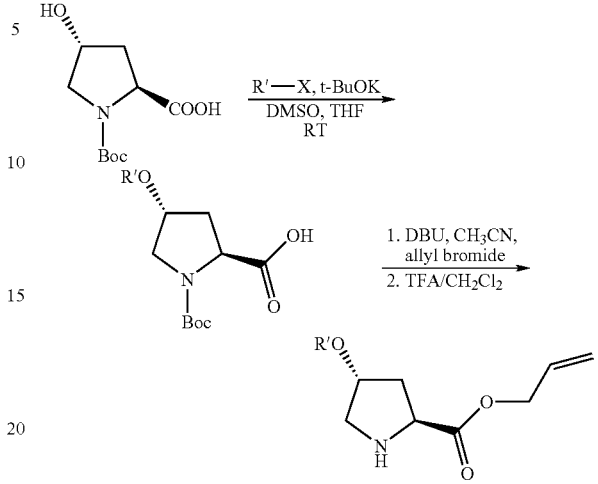

Schemes 1-8 in combination with scheme 16 above provide another general method for the preparation of compounds of formula I wherein the —N($R_{12}$)CH($R_{11}$)C(O)— radical is as shown above and wherein R' is as defined in any of the embodiments herein. The allyl ester may be cleaved according to procedures known to one skilled in the art. For instance the allyl ester may be cleaved using Pd(Ph$_3$)$_4$ with pyrrolidine in CH$_2$Cl$_2$ and CH$_3$CN to give the free acid. Coupling of the acid to intermediate 14 followed by utilization of the general procedures in schemes 1-8 affords compounds of formula I wherein the —N($R_{12}$)CH($R_{11}$)C(O)— radicals are as shown above. It will also be appreciated by one of skill in the art that compounds of formula I, wherein z is zero, may be prepared according to schemes 1-8 and 16 wherein one less CBz-Xaa-OH group is coupled during preparation of the compound.

Scheme 17:

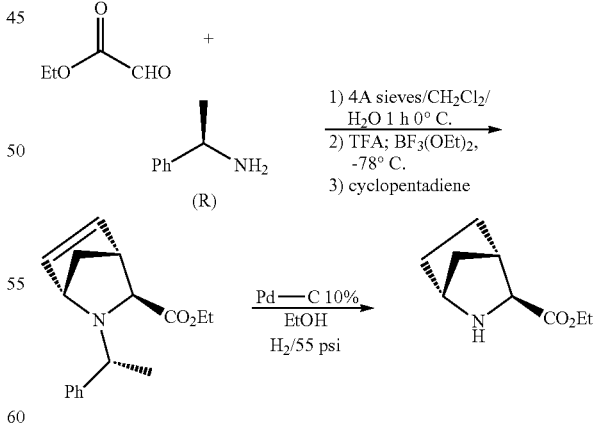

Schemes 1-8 in combination with scheme 17 above provide another general method for the preparation of compounds of formula I wherein the —N($R_{12}$)CH($R_{11}$)C(O)— radical is as shown above and wherein R' is as defined in any of the embodiments herein. It will also be appreciated by one of skill in the art that compounds of formula I, wherein z is Scheme 18:

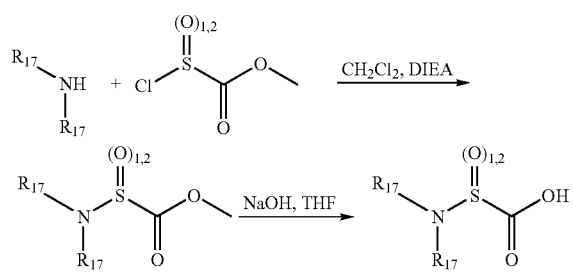

Scheme 18 above provides a general route for the preparation of compounds wherein V—R-T is as shown above and $R_{17}$ is as described in any of the embodiments herein. Therein, commercially available amine and sulfonyl chloride is condensed and then hydrolyzed under basic conditions to provide an intermediate acid. The acid is then further converted to compounds of formula I using the methods outlined in schemes 1-8. It will also be appreciated by one of skill in the art that compounds of formula I, wherein z is zero, may be prepared according to schemes 1-8 and 18 wherein one less CBz-Xaa-OH group is coupled during preparation of the compound.

Scheme 19:

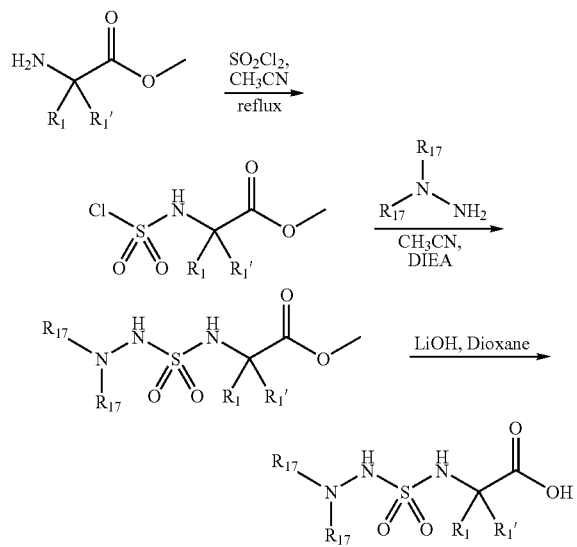

Scheme 19 above provides a general route for the preparation of compounds wherein V—R-T is as depicted above, and $R_{17}$, $R_1$, and $R_{1'}$ are as described in any of the embodiments herein. Therein, commercially available amino acid ester is converted to the corresponding N-chlorosulfonyl ester according to the procedure described by Kempf, D. J. et al., *J. Med. Chem.*, pp. 320-330 (1993). Coupling of sulfonyl chloride with a hydrazine of interest (obtained commercially or synthesized according to well known procedures in the art) followed by basic hydrolysis yields the intermediate acid. The acid intermediate is then converted to compounds of formula I using the methods outlined in schemes 1-8 above.

Scheme 19a:

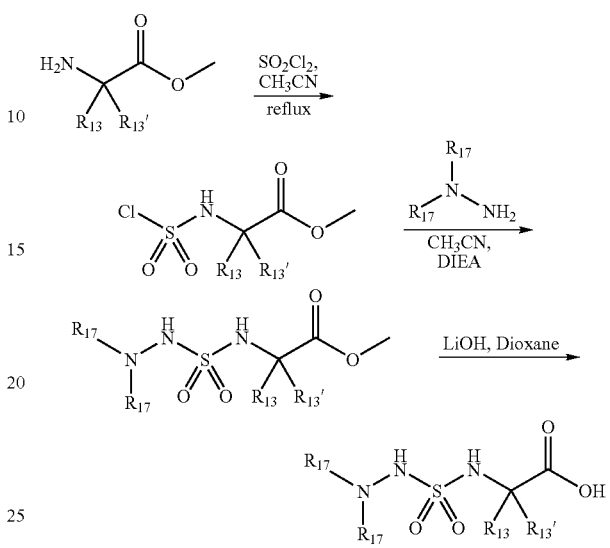

Scheme 19a above provides a general route for the preparation of compounds wherein V-R-T is as depicted above, and $R_{17}$, $R_{13}$, and $R_{13'}$ are as described in any of the embodiments herein. Therein, commercially available amino acid ester is converted to the corresponding N-chlorosulfonyl ester according to the procedure described by Kempf, D. J. et al., *J. Med. Chem.*, pp. 320-330 (1993). Coupling of sulfonyl chloride with a hydrazine of interest (obtained commercially or synthesized according to well known procedures in the art) followed by basic hydrolysis yields the intermediate acid. The acid intermediate is then converted to compounds of formula I, wherein z is zero, using the methods outlined in schemes 1-8 above.

Scheme 20:

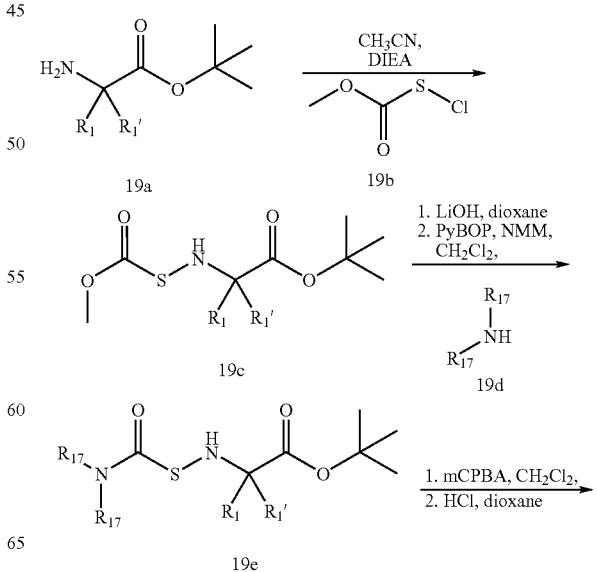

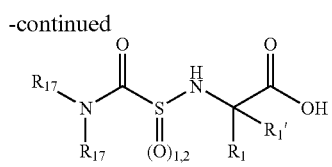

19f

Scheme 20 above provides a general route for the preparation of compounds wherein V—R-T is as depicted above, and $R_{17}$, $R_1$, and $R_{1'}$ are as described in any of the embodiments herein. Chloroester 19b is prepared according to the methods described in *J. Org. Chem., pp.* 2624-2629 (1979). Coupling of commercially available amino t-butyl ester 19a with chloride 19b gives sulfonamide 19c. Basic hydrolysis of mixed ester 19c followed by coupling with commercially available amine 19d affords intermediate ester 19e. Oxidation with one equivalent of mCBPA affords sulfoxide, wherein V is —S(O)$_1$—. Alternatively, oxidation with two equivalents of mCBPA affords sulfone, wherein V is —S(O)$_2$—. Acidic hydrolysis of t-butyl ester 19e yields acid 19f, which is then further elaborated to compounds of formula I according to the procedures outlined above in schemes 1-8.

Scheme 20a:

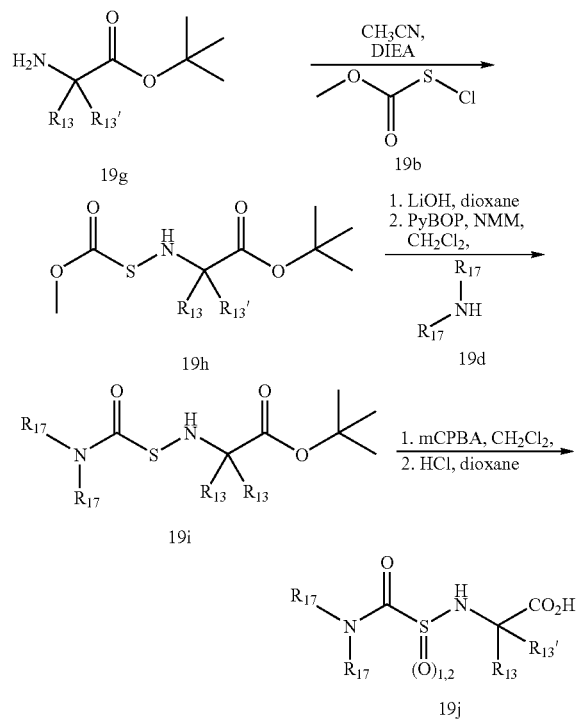

Scheme 20a above provides a general route for the preparation of compounds wherein V—R-T is as depicted above, and $R_{17}$, $R_{13}$, and $R_{13'}$ are as described in any of the embodiments herein. Chloroester 19b is prepared according to the methods described in *J. Org. Chem., pp.* 2624-2629 (1979). Coupling of commercially available amino t-butyl ester 19g with chloride 19b gives sulfonamide 19h. Basic hydrolysis of mixed ester 19h followed by coupling with commercially available amine 19d affords intermediate ester 19i. Oxidation with one equivalent of mCBPA affords sulfoxide, wherein V is —S(O)$_1$—. Alternatively, oxidation with two equivalents of mCBPA affords sulfone, wherein V is —S(O)$_2$—. Acidic hydrolysis of t-butyl ester 19i yields acid 19j, which is then further elaborated to compounds of formula I, wherein z is zero, according to the procedures outlined above in schemes 1-8.

Scheme 21:

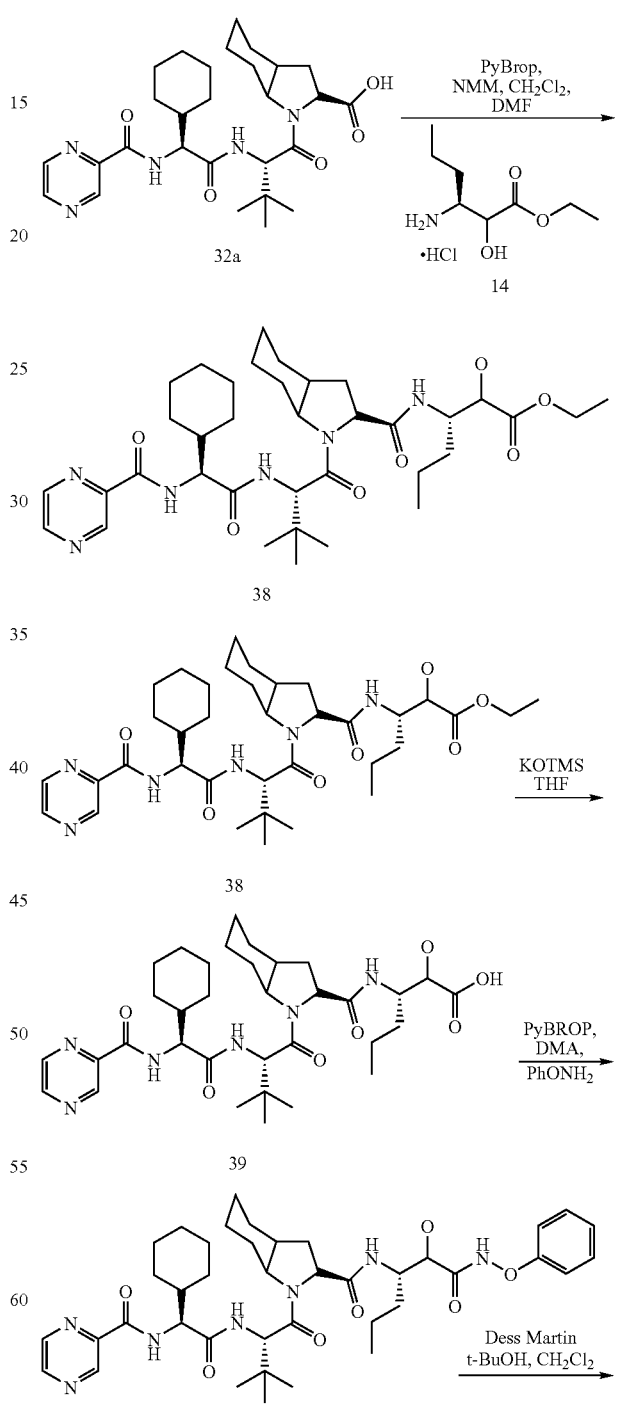

-continued

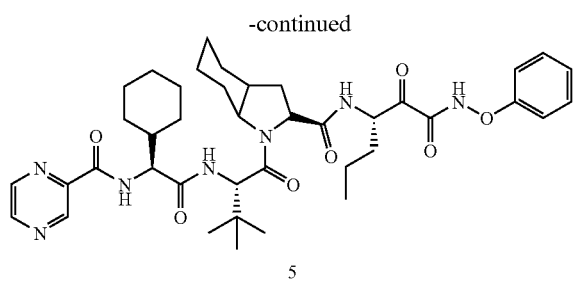

5

Scheme 21 above provides a route for the preparation of compound 5 of the present invention from intermediate 32a. Intermediate 32a is prepared according to the general procedures listed in schemes 1 and 2 from commercially available starting materials. Experimental procedures for the preparation of compound 5 from intermediate 32a and intermediate 14 are detailed in the examples section provided herein.

Scheme 22:

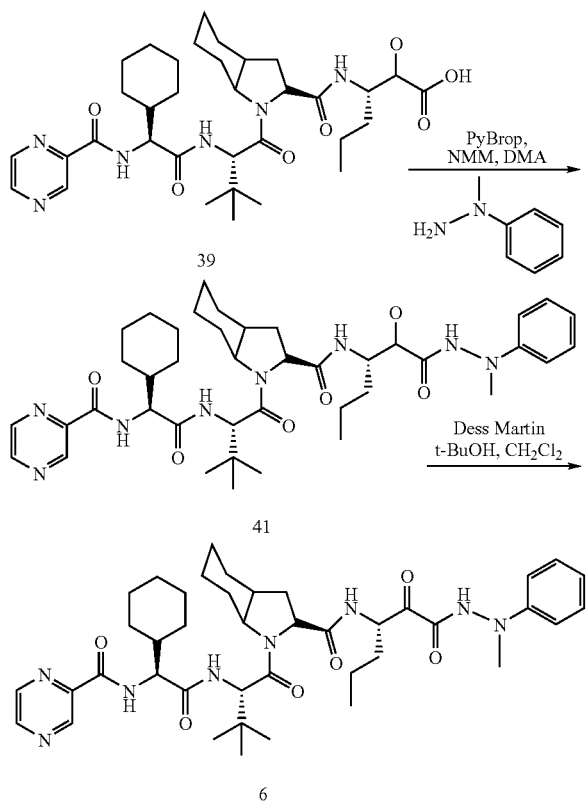

Scheme 22 above provides a route for the preparation of compound 6 of the present invention from intermediate 39. Intermediate 39 is prepared according to the general procedures listed in schemes 1, 2, and 21 from commercially available starting materials. Experimental procedures for the preparation of compound 6 from intermediate 39 are detailed in the examples section provided herein.

The preparation of various other optionally substituted multicyclic azaheterocyclyl intermediates to prepare compounds of formula I via schemes 1-8 above, may be accomplished by the methods described in PCT publication No. WO 02/18369 and references cited therein.

Various 3, 4, and 5-substituted proline analogues useful as P2 moieties may either be purchased commercially or prepared according to known literature procedures. For instance, certain 3-substituted proline analogues of interest may be prepared according to the method of Holladay, M. W. et al., *J. Med. Chem.*, 34, pp. 457-461 (1991). Additionally, various 3,4-disubstituted proline analogues may be prepared according to the method of Kanamasa, S. et al., *J. Org. Chem*, 56, pp. 2875-2883 (1991). In each of the syntheses involving 3, 4, or 5-substituted prolines or 3,4-disubstituted prolines, the intermediates may be further elaborated by the routes defined above in schemes 1-8 to prepare compounds of the present invention.

Although certain embodiments are depicted and described below, it will be appreciated that compounds of this invention can be prepared according to the methods described generally above using appropriate starting materials generally available to one of ordinary skill in the art.

In other forms of any embodiment of this invention, a pharmaceutical composition is provided comprising a compound of the present invention or a pharmaceutically acceptable salt or mixtures thereof. In other forms of any embodiment of this invention, the compound of the present invention is present in an amount effective to decrease the viral load in a sample or in a patient, wherein said virus encodes a serine protease necessary for the viral life cycle, and a pharmaceutically acceptable carrier.

If pharmaceutically acceptable salts of the compounds of this invention are utilized in these compositions, those salts may be derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentane-propionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

In other forms of any embodiment of this invention, the compositions of this invention are formulated for pharmaceutical administration to a mammal. In other forms of any embodiment of this invention, the compositions of this invention are formulated for pharmaceutical administration to a human being.

Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In other forms of any embodiment of this invention, the compositions are administered orally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Dosage levels of between about 0.01 and about 100 mg/kg body weight per day of the protease inhibitor compounds described herein are useful in a monotherapy for the prevention and treatment of antiviral, particularly anti-HCV mediated disease. In other forms of any embodiment of this invention, dosage levels of between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Another such preparation will contain from about 20% to about 80% active compound.

When the compositions of this invention comprise a combination of a compound of formula I and one or more additional therapeutic or prophylactic agents, both the compound and the additional agent should be present at dosage levels of between about 10 to 100% of the dosage normally administered in a monotherapy regimen. In other forms of any embodiment of this invention, compositions of this invention comprise a combination of a compound of formula I and one or more additional therapeutic or prophylactic agents wherein both the compound and the additional agent should be present at dosage levels of between about 10 to 80% of the dosage normally administered in a monotherapy regimen.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In other forms of any embodiment of this invention, the pharmaceutical compositions are formulated for oral administration.

In other forms of any embodiment of this invention, the compositions of this invention additionally comprise another anti-viral agent, preferably an anti-HCV agent. Such anti-viral agents include, but are not-limited to, immunomodulatory agents, such as α-, β-, and γ-interferons, pegylated derivatized interferon-α compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase and polymerase inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above. See also W. Markland et al., *Antimicrobial & Antiviral Chemotherapy,* 44, p. 859 (2000) and U.S. Pat. No. 6,541,496.

VX-497

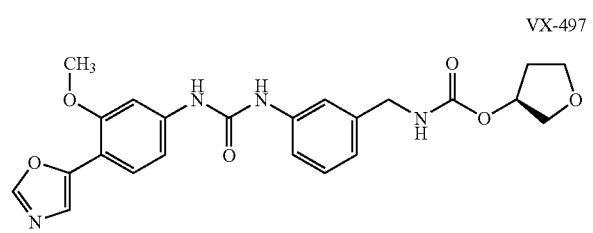

The following definitions are used herein (with trademarks referring to products available as of this application's filing date).

"Peg-Intron" means PEG-Intron®, peginterferon alfa-2b, available from Schering Corporation, Kenilworth, N.J.;

"Intron" means Intron-A®, interferon alfa-2b available from Schering Corporation, Kenilworth, N.J.;

"ribavirin" means ribavirin (1-beta-D-ribofuranosyl-1H-1, 2,4-triazole-3-carboxamide, available from ICN Pharmaceuticals, Inc., Costa Mesa, Calif.; described in the Merck Index, entry 8365, Twelfth Edition; also available as Rebetol® from Schering Corporation, Kenilworth, N.J., or as Copegus® from Hoffmann-La Roche, Nutley, N.J.;

"Pagasys" means Pegasys®, peginterferon alfa-2a available Hoffmann-La Roche, Nutley, N.J.;

"Roferon" mean Roferon®, recombinant interferon alfa-2a available from Hoffmann-La Roche, Nutley, N.J.;

"Berefor" means Berefor®, interferon alfa 2 available from Boehringer Ingelheim Pharmaceutical, Inc., Ridgefield, Conn.;

Sumiferon®, a purified blend of natural alpha interferons such as Sumiferon available from Sumitomo, Japan;

Wellferon®, interferon alpha n1 available from Glaxo_Wellcome LTd., Great Britain;

Alferon®, a mixture of natural alpha interferons made by Interferon Sciences, and available from Purdue Frederick Co., Conn.;

The term "interferon" as used herein means a member of a family of highly homologous species-specific proteins that inhibit viral replication and cellular proliferation, and modulate immune response, such as interferon alpha, interferon beta, or interferon gamma. The Merck Index, entry 5015, Twelfth Edition.

In other forms of any embodiment of this invention, the interferon is a-interferon. In other forms of any embodiment of this invention, a therapeutic combination of the present invention utilizes natural alpha interferon 2a. Or, the therapeutic combination of the present invention utilizes natural alpha interferon 2b. In other forms of any embodiment of this invention, the therapeutic combination of the present invention utilizes recombinant alpha interferon 2a or 2b. In other forms of any embodiment of this invention, the interferon is pegylated alpha interferon 2a or 2b. Interferons suitable for the present invention include:
(a) Intron (interferon-alpha 2B, Schering Plough),
(b) Peg-Intron,
(c) Pegasys,
(d) Roferon,
(e) Berofor,
(f) Sumiferon,
(g) Wellferon,
(h) consensus alpha interferon available from Amgen, Inc., Newbury Park, Calif.,
(i) Alferon;
(j) Viraferon®;
(k) Infergen®.

As is recognized by skilled practitioners, a protease inhibitor would be preferably administered orally. Interferon is not typically administered orally. Nevertheless, nothing herein limits the methods or combinations of this invention to any specific dosage forms or regime. Thus, each component of a combination according to this invention may be administered separately, together, or in any combination thereof.

In other forms of any embodiment of this invention, the protease inhibitor and interferon are administered in separate dosage forms. In other forms of any embodiment of this invention, any additional agent is administered as part of a single dosage form with the protease inhibitor or as a separate dosage form. As this invention involves a combination of compounds, the specific amounts of each compound may be dependent on the specific amounts of each other compound in the combination. As recognized by skilled practitioners, dosages of interferon are typically measured in IU (e.g., about 4 million IU to about 12 million IU).

Accordingly, agents (whether acting as an immunomodulatory agent or otherwise) that may be used in combination with a compound of this invention include, but are not limited to, interferon-alpha 2B (Intron A, Schering Plough); Rebatron (Schering Plough, Inteferon-alpha 2B+Ribavirin); pegylated interferon alpha (Reddy, K. R. et al. "Efficacy and Safety of Pegylated (40-kd) interferon alpha-2a compared with interferon alpha-2a in noncirrhotic patients with chronic hepatitis C (*Hepatology,* 33, pp. 433-438 (2001); consensus interferon (Kao, J. H., et al., "Efficacy of Consensus Interferon in the Treatement of Chronic Hepatitis" *J. Gastroenterol. Hepatol.* 15, pp. 1418-1423 (2000), interferon-alpha 2A (Roferon A; Roche), lymphoblastoid or "natural" interferon; interferon tau (Clayette, P. et al., "IFN-tau, A New Interferon Type I with Antiretroviral activity" *Pathol. Biol.*

(Paris) 47, pp. 553-559 (1999); interleukin 2 (Davis, G. L. et al., "Future Options for the Management of Hepatitis C." *Seminars in Liver Disease,* 19, pp. 103-112 (1999); Interleukin 6 (Davis et al. "Future Options for the Management of Hepatitis C." *Seminars in Liver Disease* 19, pp. 103-112 (1999); interleukin 12 (Davis, G. L. et al., "Future Options for the Management of Hepatitis C." *Seminars in Liver Disease,* 19, pp. 103-112 (1999); Ribavirin; and compounds that enhance the development of type 1 helper T cell response (Davis et al., "Future Options for the Management of Hepatitis C." *Seminars in Liver Disease,* 19, pp. 103-112 (1999). Interferons may ameliorate viral infections by exerting direct antiviral effects and/or by modifying the immune response to infection. The antiviral effects of interferons are often mediated through inhibition of viral penetration or uncoating, synthesis of viral RNA, translation of viral proteins, and/or viral assembly and release.

Compounds that stimulate the synthesis of interferon in cells (Tazulakhova, E. B. et al., "Russian Experience in Screening, analysis, and Clinical Application of Novel Interferon Inducers" *J. Interferon Cytokine Res.,* 21 pp. 65-73) include, but are not limited to, double stranded RNA, alone or in combination with tobramycin, and Imiquimod (3M Pharmaceuticals; Sauder, D. N. "Immunomodulatory and Pharmacologic Properties of Imiquimod" *J. Am. Acad. Dermatol.,* 43 pp. S6-11 (2000).

Other non-immunomodulatory or immunomodulatory compounds may be used in combination with a compound of this invention including, but not limited to, those specified in WO 02/18369, which is incorporated herein by reference (see, e.g., page 273, lines 9-22 and page 274, line 4 to page 276, line 11).

This invention may also involve administering a cytochrome P450 monooxygenase inhibitor. CYP inhibitors may be useful in increasing liver concentrations and/or increasing blood levels of compounds that are inhibited by CYP.

If an embodiment of this invention involves a CYP inhibitor, any CYP inhibitor that improves the pharmacokinetics of the relevant NS3/4A protease may be used in a method of this invention. These CYP inhibitors include, but are not limited to, ritonavir (WO 94/14436), ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. For preferred dosage forms of ritonavir, see U.S. Pat. No. 6,037, 157, and the documents cited therein: U.S. Pat. No. 5,484,801, U.S. application Ser. No. 08/402,690, and International Applications WO 95/07696 and WO 95/09614).

Methods for measuring the ability of a compound to inhibit cytochrome P50 monooxygenase activity are known (see U.S. Pat. No. 6,037,157 and Yun, et al. *Drug Metabolism & Disposition,* vol. 21, pp. 403-407 (1993).

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and the presence or absence and the nature of the additional anti-viral agent in the composition.

In other forms of any embodiment of this invention, a method is provided for treating a patient infected with a virus characterized by a virally encoded serine protease that is necessary for the life cycle of the virus by administering to said patient a pharmaceutically acceptable composition of this invention. In other forms of any embodiment of this invention, the methods are used to treat a patient suffering from an HCV infection. Such treatment may completely eradicate the viral infection or reduce the severity thereof. In other forms of any embodiment of this invention, the patient is a human being.

In other forms of any embodiment of this invention, the methods provided additionally comprise the step of administering to said patient an anti-viral agent such as an anti-HCV agent. Such anti-viral agents include, but are not limited to, immunomodulatory agents, such as $\alpha$-, $\beta$-, and $\gamma$-interferons, pegylated derivatized interferon-a compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including but not limited to helicase and polymerase inhibitors; inhibitors of internal ribosome entry; broad-spectrum viral inhibitors, such as IMPDH inhibitors (e.g., VX-497 and other IMPDH inhibitors disclosed in U.S. Pat. Nos. 5,807,876 and 6,498, 178, mycophenolic acid and derivatives thereof); inhibitors of cytochrome P-450, such as ritonavir, or combinations of any of the above.

Such additional agent may be administered to said patient as part of a single dosage form comprising both a compound of this invention and an additional anti-viral agent. Alternatively the additional agent may be administered separately from the compound of this invention, as part of a multiple dosage form, wherein said additional agent is administered prior to, together with or following a composition comprising a compound of this invention.

In other forms of any embodiment of this invention, the present invention provides a method of pre-treating a biological substance intended for administration to a patient comprising the step of contacting said biological substance with a pharmaceutically acceptable composition comprising a compound of this invention. Such biological substances include, but are not limited to, blood and components thereof such as plasma, platelets, subpopulations of blood cells and the like; organs such as kidney, liver, heart, lung, etc; sperm and ova; bone marrow and components thereof, and other fluids to be infused into a patient such as saline, dextrose, etc.

In other forms of any embodiment of this invention, a method is provided for treating materials that may potentially come into contact with a virus characterized by a virally encoded serine protease necessary for its life cycle. This method comprises the step of contacting said material with a compound according to the invention. Such materials include, but are not limited to, surgical instruments and garments (e.g. clothes, gloves, aprons, gowns, masks, eyeglasses, footwear, etc.); laboratory instruments and garments (e.g. clothes, gloves, aprons, gowns, masks, eyeglasses, footwear, etc.); blood collection apparatuses and materials; and invasive devices, such as shunts, stents, etc.

In other forms of any embodiment of this invention, the compounds of this invention may be used as laboratory tools to aid in the isolation of a virally encoded serine protease. This method comprises the steps of providing a compound of this invention attached to a solid support; contacting said solid support with a sample containing a viral serine protease under conditions that cause said protease to bind to said solid support; and eluting said serine protease from said solid support. In other forms of any embodiment of this invention, the viral serine protease isolated by this method is HCV NS3-NS4A protease.

In order that this invention be more fully understood, the following preparative and testing examples are set forth. These examples are for the purpose of illustration only and are not to be construed as limiting the scope of the invention in any way.

EXAMPLES $^1$H-NMR spectra were recorded at 500 MHz using a Bruker AMX 500 instrument. Mass spec. samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spec. analysis consisted of acetonitrile-water mixtures with 0.2% formic acid as a modifier.

As used herein, the term "$R_t$(min)" refers to the HPLC retention time, in minutes, associated with the compound. The HPLC retention times listed were either obtained from the mass spec. data or using the following method:
Instrument: Hewlett Packard HP-1050;
Column: YMC $C_{18}$ (Cat. No. 326289C46);
Gradient/Gradient Time: 10-90% $CH_3CN/H_2O$ over 9 minutes, then 100% $CH_3CN$ for 2 minutes;
Flow Rate: 0.8 ml/min;
Detector Wavelength: 215 nM and 245 nM.

Chemical naming for selected compounds herein was accomplished using the naming program provided by CambridgeSoft Corporations ChemDraw Ultra®, version 7.0.1.

Example 1

Preparation of 3-amino-2-hydroxy-hexanoic acid ethyl ester hydrochloride (14)

To a solution of the carboxylic acid 9 (4.5 g, 24.5 mmols), which was prepared according to the procedure of Harbeson, S. et al. in *J. Med. Chem.* 37, 18, pp. 2918-2929 (1994) in ethanol (50 mL) was added 6 mL of saturated hydrochloric acid in ethyl acetate, followed by a catalytic amount of concentrated sulfuric acid. The reaction was stirred at ambient temperature overnight. The solvent was removed and the residue was dried under vacuum. The amino acid was completely converted to the amino ester based on TLC analysis. The product was used as is without further purification.

Example 2

Preparation of 3-{[1-(2-{2-Cyclohexyl-2-[(pyrazine-2-carbonyl)-amino]-acetylamino}-3,3-dimethyl-butyryl)-octahydro-indole-2-carbonyl]-amino}-2-hydroxy-hexanoic acid ethyl ester (32)

In a dry flask charged with a 1:1 mixture of dichloromethane-dimethylformamide (100 ml) was placed 1-(2-{2-Cyclohexyl-2-[(pyrazine-2-carbonyl)-amino]-acetylamino}-3,3-dimethyl-butyryl)-octahydro-indole-2-carboxylic acid 32a (2.0 g, 4.28 mmols), PyBOP (2.5 g, 4.7 mmol), and N-methyl-morpholine (2.4 ml, 21.4 mmol) and the reaction placed under an atmosphere of nitrogen. In a 100 mL addition funnel was placed a solution of the amine 14 (1.0 g, 4.7 mmols) and N-methyl-morpholine (0.60 ml, 5.35 mmol) in a 1:1 mixture of dichloromethane-dimethylformamide (10 ml). The reaction was cooled to 0° C., and the amine was added while maintaining the temperature at 0° C. The reaction was allowed to warm to ambient temperature as it was stirred over night. HPLC analysis showed the reaction to be complete, and then the reaction was diluted with water to 500 mL. After stirring the precipitate was filtered and dried to give 2.4 g (82% yield) of 32 as a beige solid. This material was used as is in the next step without further purification. HPLC: RT=5.66 min, (10-90% acetonitrile-water over 7 minutes); LC/MS: retention time 3.94 min (10-90% acetonitrile-water over 5 minutes); $M+H^+$=685.5.

Example 3

Preparation of 1-(2-{2-Cyclohexyl-2-[(pyrazine-2-carbonyl)-amino]-acetylamino}-3,3-dimethyl-butyryl)-octahydro-indole-2-carboxylic acid [1-(N'-methyl-N'-phenyl-hydrazinooxalyl)-butyl]-amide (6)

To a solution of the acid 33 (100 mgs, 0.152 mmols), in DMA (1 mL) was added PyBrop (110 mgs, 0.213 mmols), N-methyl morpholine (250 uL, 0.2.27 mmols), and N-methyl-N-phenyl-hydrazine (122 mgs, 1.0 mmols), and the reaction was stirred until the starting acid was consumed by HPLC analysis. The reaction was diluted with water and the product precipitated from the solution. The solids were filtered and dried to give 70 mgs (60%) of 36, with consistent mass spec. data ($M+H^+$=761). This material was used as is without further purification.

To a solution of hydroxy-hydrazide 36 (70 mgs, 0.092 mmols) in $CH_2Cl_2$ (2 mL) was added Dess-Martin periodinane (100 mgs, 0.236 mmol) and 100 uL of tert-butyl alcohol and the reaction was stirred at RT for one hour. The solvent was removed and the material was purified by flash chromatography on silica gel (50% EtOAc -hexanes) to give product as a colorless glass. The material was dissolved in 50% acetonitrile-water and lyophilyzed to give 23 mgs of 6 as a colorless solid with consistent mass spec data (LC/MS; RT=4.30 min, 10-90% acetonitrile-water over 7 min; M+H+=759.1).

Compounds 7 and 8 were also prepared according to the procedure described above for compound 6.

Example 4

Preparation of 1-(2-{2-Cyclohexyl-2-[(pyrazine-2-carbonyl)-amino]-acetylamino}-3,3-dimethyl-butyryl)-octahydro-indole-2-carboxylic acid (1-phenoxyaminooxalyl-butyl)-amide (5)

To a solution of the acid 33 (200 mgs, 0.304 mmols), in DMA (1 mL) was added PyBrop (200 mgs, 0.43 mmols), N-methyl morpholine (400 uL, 3.62 mmols), and O-phenyl-hydroxylamine (100 mgs, 0.682 mmols), and the reaction was stirred until the starting acid was consumed by HPLC analysis. The reaction was diluted with water and the product precipitated from the solution. The solids were filtered and dried to give 78 mgs (34%) of 34, which was used in the next step without any further purification.

To a solution of hydroxy-amide 34 (78 mgs, 0.10 mmols) in $CH_2Cl_2$ (2 mL) was added Dess-Martin periodinane (68 mgs, 0.16 mmol) and 100 uL of tert-butyl alcohol and the reaction was stirred at RT for one hour. The solvent was removed and the material was purified by preparative thin layer chromatography on silica gel (5% isopropanol-EtOAc) to give 5.8 mgs (6%) of 5 as a colorless glass with consistent mass spec. data (LC/MS; RT=4.50 min, (10-90% acetonitrile-water over 7 min); M+H$^+$=746.1).

Compounds 1 to 4 were also prepared according to the procedure described above for compound 5.

Example 5

Preparation of 1-(2-{2-Cyclohexyl-2-[(pyrazine-2-carbonyl)-amino]-acetylamino}-3,3-dimethyl-butyryl)-octahydro-indole-2-carboxylic acid (1-isobutoxyaminooxalyl-butyl)-amide (1)

This compound was prepared using procedures similar to those listed in schemes 1, 2, 4, and 21. The product was isolated as a solid with consistent mass spec. data (LC/MS; retention time=4.2, M+H$^+$=726 observed.

Example 6

Preparation of 1-(2-{2-Cyclohexyl-2-[(pyrazine-2-carbonyl)-amino]-acetylamino}-3,3-dimethyl-butyryl)-octahydro-indole-2-carboxylic acid (1-tert-butoxyaminooxalyl-butyl)-amide (2)

This compound was prepared using procedures similar to those listed in schemes 1, 2, 4, and 21. The product was isolated as a solid with consistent mass spec. data (LC/MS; retention time=4.1, M+H$^+$=726.3 observed.

Example 7

Preparation of 1-(2-{2-Cyclohexyl-2-[(pyrazine-2-carbonyl)-amino]-acetylamino}-3,3-dimethyl-butyryl)-octahydro-indole-2-carboxylic acid (1-benzyloxyaminooxalyl-butyl)-amide (3)

This compound was prepared using procedures similar to those listed in schemes 1, 2, 4, and 21. The product was isolated as a solid with consistent mass spec. data (LC/MS; retention time=4.2, M+H$^+$=760 observed.

Example 8

Preparation of 1-(2-{2-Cyclohexyl-2-[(pyrazine-2-carbonyl)-amino]-acetylamino}-3,3-dimethyl-butyryl)-octahydro-indole-2-carboxylic acid (1-allyloxyaminooxalyl-butyl)-amide (4)

This compound was prepared using procedures similar to those listed in schemes 1, 2, 4, and 21. The product was isolated as a solid with consistent mass spec. data (LC/MS; retention time=3.8, M+H$^+$=710 observed.

Example 9

Preparation of 1-(2-{2-Cyclohexyl-2-[(pyrazine-2-carbonyl)-amino]-acetylamino}-3,3-dimethyl-butyryl)-octahydro-indole-2-carboxylic acid [1-(morpholin-4-ylaminooxalyl-butyl]-amide (7)

This compound was prepared using procedures similar to those listed in schemes 1, 2, 3, and 22. The product was isolated as a colorless solid with consistent mass spec. data (LC/MS; retention time=3.7, M+H$^+$=739.4 observed.

Example 10

Preparation of 1-(2-{2-Cyclohexyl-2-[(pyrazine-2-carbonyl)-amino]-acetylamino}-3,3-dimethyl-butyryl)-octahydro-indole-2-carboxylic acid[1-(N',N'-dibenzyl-hydrazinooxalyl-butyl]-amide (8)

This compound was prepared using procedures similar to those listed in schemes 1, 2, 3, and 22. The product was isolated as a colorless solid with consistent mass spec. data (LC/MS; retention time=4.94, M+H$^+$=849 observed.

Example 11

HCV Ki Assay Protocol

HPLC Microbore Method for Separation of 5AB Substrate and Products
Substrate:

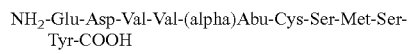
NH$_2$-Glu-Asp-Val-Val-(alpha)Abu-Cys-Ser-Met-Ser-Tyr-COOH

A stock solution of 20 mM 5AB (or concentration of your choice) was made in DMSO w/0.2M DTT. This was stored in aliquots at −20° C.

Buffer: 50 mM HEPES, pH 7.8; 20% glycerol; 100 mM NaCl

Total assay volume was 100 μL

| Reagent | X1 (μL) | conc. in assay |
|---|---|---|
| Buffer | 86.5 | see above |
| 5 mM KK4A | 0.5 | 25 μM |
| 1 M DTT | 0.5 | 5 mM |
| DMSO or inhibitor | 2.5 | 2.5% v/v |
| 50 μM tNS3 | 0.05 | 25 nM |
| 250 μM 5AB (initiate) | 20 | 25 μM |

The buffer, KK4A, DTT, and tNS3 were combined; distributed 78 μL each into wells of 96 well plate. This was incubated at 30° C. for ~5-10 min.

2.5 μL of appropriate concentration of test compound was dissolved in DMSO (DMSO only for control) and added to each well. This was incubated at room temperature for 15 min.

Initiated reaction by addition of 20 μL of 250 μM 5AB substrate (25 μM concentration is equivalent or slightly lower than the Km for 5AB).

Incubated for 20 min at 30° C.

Terminated reaction by addition of 25 μL of 10% TFA

Transferred 120 μL aliquots to HPLC vials

Separated SMSY product from substrate and KK4A by the following method:

Microbore Separation Method:
  Instrumentation: Agilent 1100
Degasser G1322A
Binary pump G1312A
Autosampler G1313A
Column thermostated chamber G1316A
Diode array detector G1315A Column:
Phenomenex Jupiter; 5 micron C18; 300 angstroms; 150×2 mm; P/O 00F-4053-B0
Column thermostat: 40 C
Injection volume: 100 μL
Solvent A=HPLC grade water+0.1% TFA
Solvent B=HPLC grade acetonitrile+0.1% TFA

| Time (min) | % B | Flow (ml/min) | Max press. |
|---|---|---|---|
| 0 | 5 | 0.2 | 400 |
| 12 | 60 | 0.2 | 400 |
| 13 | 100 | 0.2 | 400 |
| 16 | 100 | 0.2 | 400 |
| 17 | 5 | 0.2 | 400 |

Stop time: 17 min
Post-run time: 10 min.

Table 1 below depicts Ki data for certain compounds of this invention. Compounds with Ki's below 1.5 μM are designated A. Compounds with Ki's ranging from 1.5 μM to 3 μM are designated B. Compounds with Ki's above 3 μM are designated C.

TABLE 1

| Compound # | Ki (μM) |
|---|---|
| 1 | A |
| 2 | A |
| 3 | B |
| 4 | C |
| 5 | B |
| 6 | A |
| 7 | C |
| 8 | C |

We claim:
1. A compound represented by:

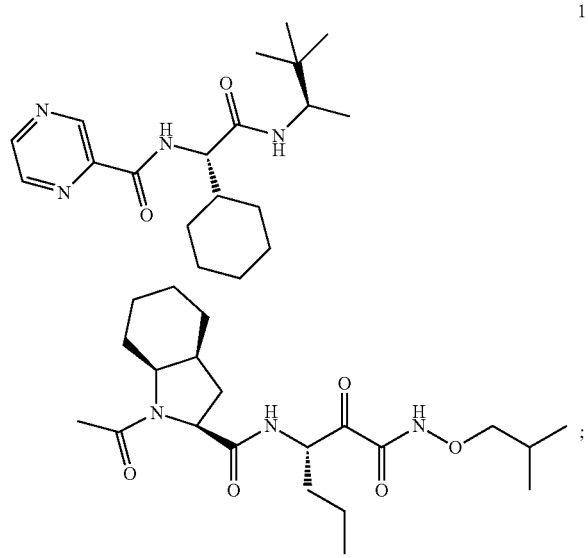

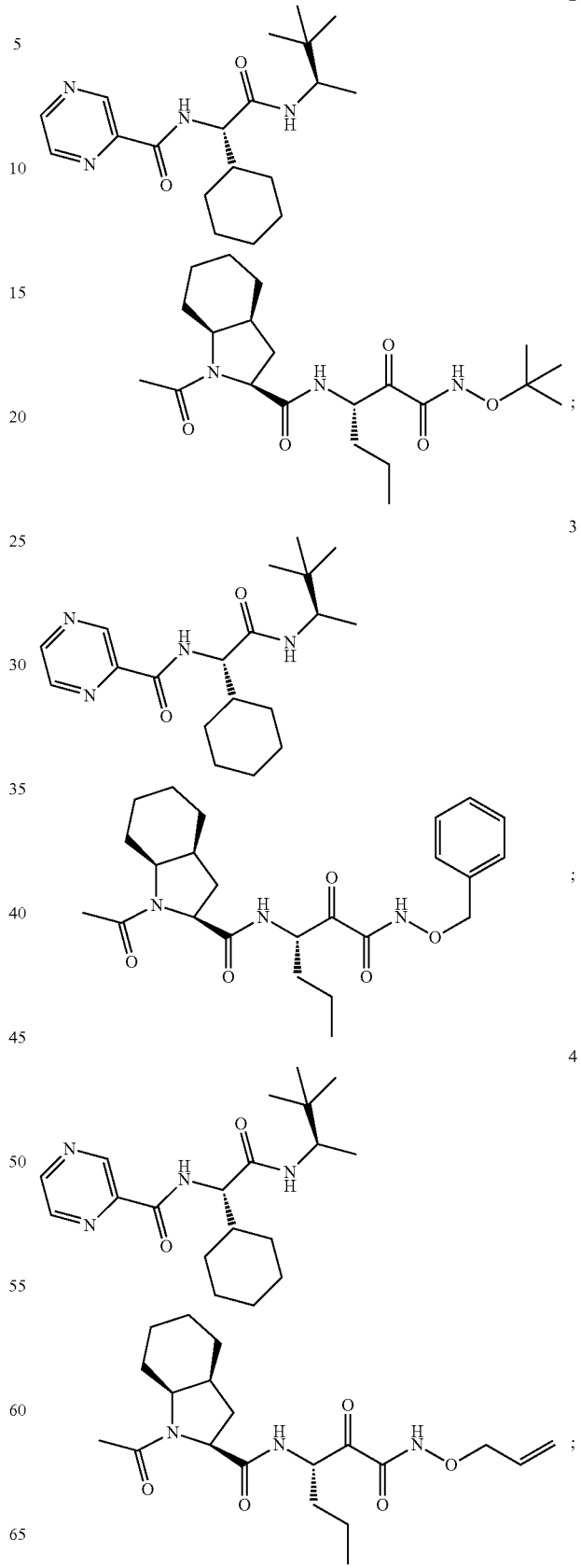

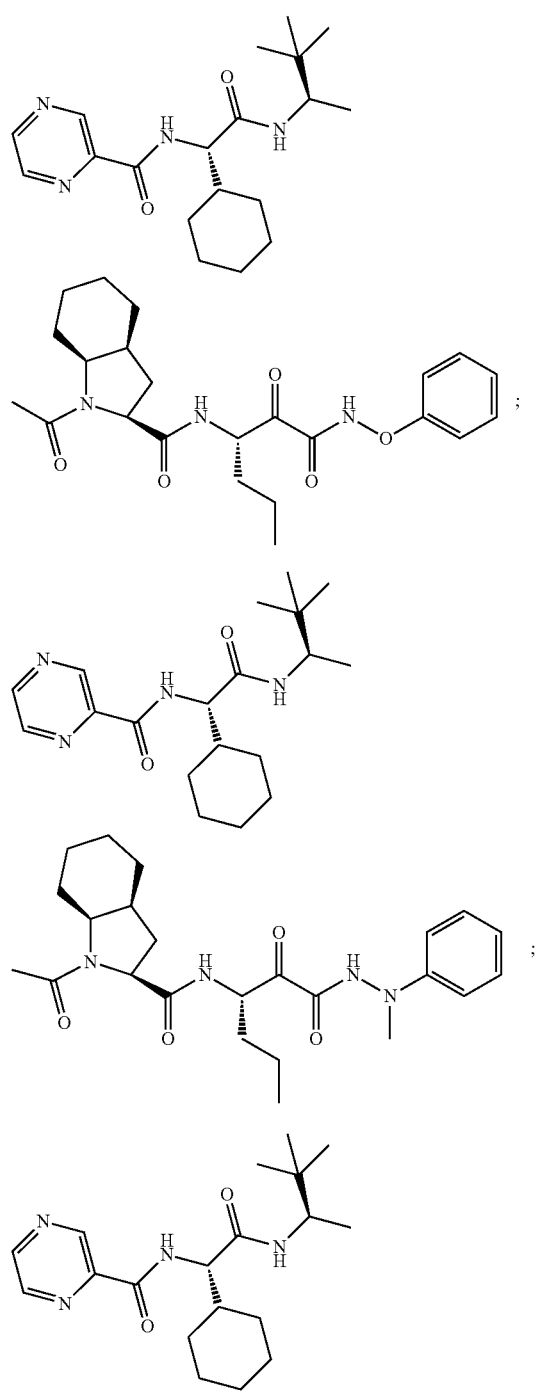

;

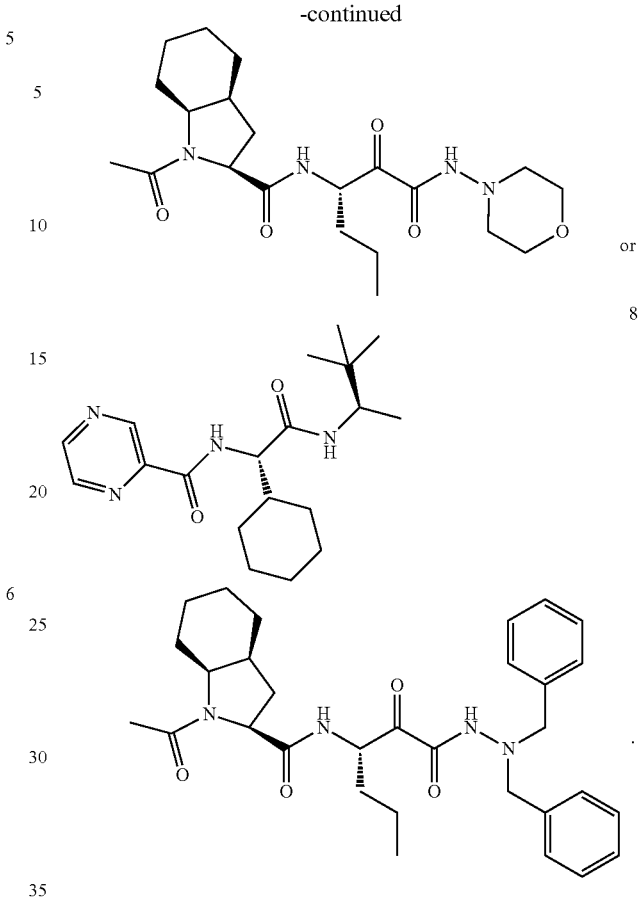

or

2. A pharmaceutical composition comprising a compound according to claim 1 or a pharmaceutically acceptable salt thereof, in an amount effective to inhibit a serine protease; and a acceptable carrier, adjuvant or vehicle.

3. The pharmaceutical composition according to claim 2, wherein said composition comprises an additional agent selected from an immunomodulatory agent; an antiviral agent; a second inhibitor of HCV protease; an inhibitor of another target in the HCV life cycle; and a cytochrome P-450 inhibitor; or combinations thereof.

4. A method of inhibiting the activity of a serine protease comprising the step of contacting said serine protease with a compound according to claim 1.

5. A method of treating an HCV infection in a patient comprising the step of administering to said patient a composition according to claim 2.

* * * * *